(12) United States Patent
Tran

(10) Patent No.: US 11,526,166 B2
(45) Date of Patent: *Dec. 13, 2022

(54) SMART VEHICLE

(71) Applicant: Ha Q Tran, Saratoga, CA (US)

(72) Inventor: Ha Q Tran, Saratoga, CA (US)

( * ) Notice: Subject to any disclaimer, the term of this patent is extended or adjusted under 35 U.S.C. 154(b) by 331 days.

This patent is subject to a terminal disclaimer.

(21) Appl. No.: 16/983,832

(22) Filed: Aug. 3, 2020

(65) Prior Publication Data

US 2021/0080950 A1 Mar. 18, 2021

Related U.S. Application Data

(63) Continuation of application No. 16/574,072, filed on Sep. 17, 2019, now Pat. No. 10,768,620.

(51) Int. Cl.
| | |
|---|---|
| G05D 1/00 | (2006.01) |
| G05D 1/02 | (2020.01) |
| B60Q 9/00 | (2006.01) |
| B60H 1/00 | (2006.01) |
| B60W 30/09 | (2012.01) |
| B60W 40/08 | (2012.01) |
| B60W 50/14 | (2020.01) |
| A61B 5/024 | (2006.01) |
| A61B 5/00 | (2006.01) |
| B60R 11/04 | (2006.01) |
| B60R 11/00 | (2006.01) |
| B60N 2/56 | (2006.01) |

(52) U.S. Cl.
CPC ....... *G05D 1/0061* (2013.01); *A61B 5/02416* (2013.01); *A61B 5/4845* (2013.01); *A61B 5/6802* (2013.01); *A61B 5/6893* (2013.01); *B60H 1/00735* (2013.01); *B60Q 9/00* (2013.01); *B60W 30/09* (2013.01); *B60W 40/08* (2013.01); *B60W 50/14* (2013.01); *G05D 1/0088* (2013.01); *G05D 1/0214* (2013.01); *B60N 2/56* (2013.01); *B60R 11/04* (2013.01); *B60R 2011/0003* (2013.01); *B60W 2040/0836* (2013.01); *B60W 2050/143* (2013.01); *B60W 2420/42* (2013.01); *B60W 2540/22* (2013.01)

(58) Field of Classification Search
CPC .. G05D 1/0061; G05D 1/0088; G05D 1/0214; A61B 5/02416; A61B 5/4845; A61B 5/6802; A61B 5/6893; A61B 5/18; A61B 5/01; A61B 5/024; A61B 5/0816; A61B 5/082; A61B 5/163; A61B 5/165; A61B 5/168; A61B 2576/00; B60H 1/00735; B60H 1/00742; B60H 1/00978; B60Q 9/00; B60Q 5/005; B60W 30/09; B60W 40/08; B60W 50/14; B60W 2040/0836; B60W 2050/143; B60W 2420/42; B60W 2540/22; B60N 2/56; B60R 11/04; B60R 2011/0003; B60R 1/00; B60R 21/015; B60R 2300/8013
See application file for complete search history.

(56) References Cited

U.S. PATENT DOCUMENTS

2019/0019068 A1* 1/2019 Zhu ........................ G06V 10/82

* cited by examiner

*Primary Examiner* — Brian P Sweeney
(74) *Attorney, Agent, or Firm* — PatentPC; Bao Tran

(57) ABSTRACT

A method of providing safety in a level 3 autonomous vehicle by mounting a plurality of cameras in a vehicular cabin to detect edges; translating the edges into motions of a human or a biological entity; and monitoring safety conditions for the human or biological entity.

20 Claims, 36 Drawing Sheets

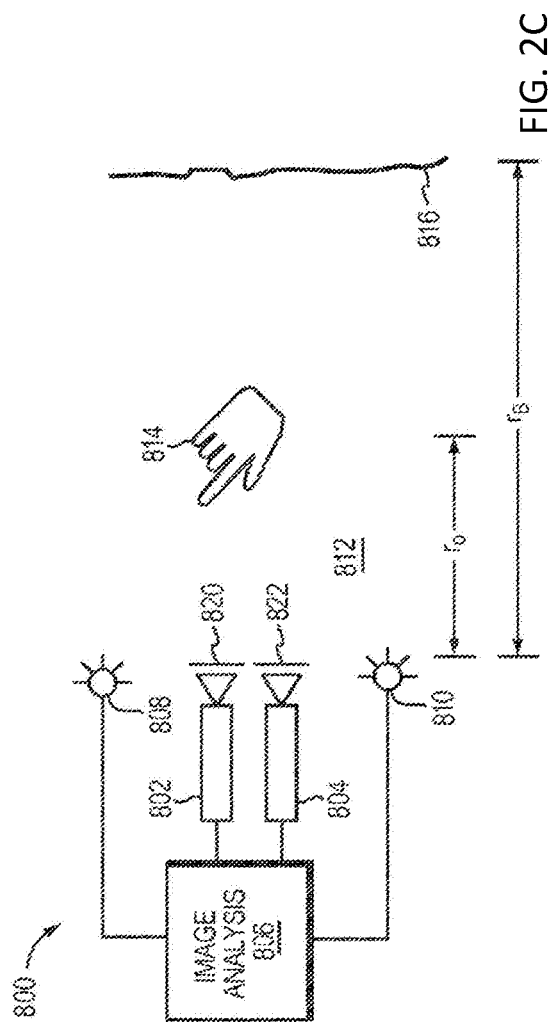

FIG. 2C

| mounting a plurality of cameras in a vehicular cabin to detect edges of an object |
| translating the edges into motions of a human or a biological entity |
| monitoring safety conditions for the human biological entity |

FIG. 3

| sensing alcohol level with a set of breath sensors or touch-sensitive contact points from a driver of the vehicle |
| determining driver impairment level |
| enforcing driving adjustments to maximize safety |

FIG. 4

| Traveler | User-1 | User-2 | User-N | Matching | Recommendation |
|---|---|---|---|---|---|
| Speed | X | | X | 2 | Yes |
| Acceleration | | X | | 1 | No |
| Drunk | X | X | X | 3 | Yes |
| Sober | | X | X | 2 | Yes |
| Location-1 | X | X | X | 3 | Yes |
| Belt used | | | | 0 | No |
| Position | | | X | 1 | No |
| Location-6 | X | X | X | 3 | Yes |
| Location-N | | X | | 1 | No |
| Indicator used | X | X | X | 3 | Yes |
| Matching | 5 | 7 | 7 | | |

SMART VEHICLE

BACKGROUND

The present invention relates to smart vehicles.

SUMMARY

Smart car operations are detailed. The smart car has a number of sensors such as IoT (internet of things) sensors that can share data with other vehicles and that can communicate with the cloud to provide intelligent handling of the car.

In another aspect, method of providing safety in a level 3 autonomous vehicle by mounting a plurality of cameras in a vehicular cabin to detect edges; translating the edges into motions of a human or a biological entity; and monitoring safety conditions for the human or biological entity.

In yet another aspect, a method for detecting attentiveness includes placing a camera near a driver, the camera having a wireless radio to communicate with a processor; sending a radio signal toward the driver and detecting a heart rate from the driver based on a reflected radio signal; capturing images of the driver; and detecting driver attentiveness based on camera images and the detected heart rate.

Implementations can include one or more of the following: determining if the driver is unable to control the car in time and detecting verbal or visual cues from the driver on action to take; detecting a driver eye gaze direction and following the direction; detecting a driver gesture direction and following the direction; if the driver gesture indicates a panic, determining an environmental cue for action—wherein the environmental cue includes paths of neighboring cars, comprising steering the car to follow one car path, or wherein the environmental cue includes an obstruction, comprising steering the car to protect the driver; if collision is imminent, the vehicle ejects the driver; the ejected driver can hover at a safe distance, or can land with a parachute; camera images are provided to a neural network to determine one or more of: heart beat monitoring, blood pressure monitoring, skin temperature and respiration rate; the camera images are provided to a neural network to determine hyperthermia or dehydration; system detects emotion, drowsiness or fatigue from combination of determining facial expression, hand gesture, and heart rate or breathing rate; based on the emotion, drowsiness or fatigue, system can increase sensitivity to Traffic Signal Recognition, Lane Departure Warning, Collision Detection, Pedestrian Detection.

In another aspect, a method for transferring control from an autonomous mode to a driver includes placing a camera near a driver, the camera having a wireless radio to communicate with a processor; sending a radio signal toward the driver and detecting a heart rate from the driver based on a reflected radio signal; capturing images of the driver; detecting driver attentiveness based on camera images and the detected heart rate; and determining if the driver is unable to control the car in time and detecting verbal or visual cues from the driver on action to take.

Implementations can include one or more of the following: detecting a driver eye gaze direction and following the direction; detecting a driver gesture direction and following the direction; if the driver gesture indicates a panic, determining an environmental cue for action; wherein the environmental cue includes paths of neighboring cars, comprising steering the car to follow one car path; wherein the environmental cue includes an obstruction, comprising steering the car to protect the driver; if collision is imminent, the vehicle ejects the driver; the ejected driver can hover at a safe distance, or can land with a parachute; the camera images are provided to a neural network to determine one or more of: heart beat monitoring, blood pressure monitoring, skin temperature and respiration rate; the camera images are provided to a neural network to determine hyperthermia or dehydration; system detects emotion, drowsiness or fatigue from combination of determining facial expression, hand gesture, and heart rate or breathing rate; based on the emotion, drowsiness or fatigue, system can increase sensitivity to Traffic Signal Recognition, Lane Departure Warning, Collision Detection, Pedestrian Detection.

In yet another aspect, a method for detecting forgotten baby or pet in a car with a cabin includes placing a camera near a driver, the camera having a wireless radio to communicate with a processor; sending a radio signal from a front of the cabin and detecting a movement in the car based on a reflected radio signal; capturing images of the cabin; detecting forgotten baby or pet based on camera images and the movement; and generating an alarm to protect the baby or pet.

Implementation can include one or more of the following. The method includes: automatically opening a window to ventilate the car; notifying an adult of the forgotten baby or pet; autonomously driving the car to a safe or comfortable area. The system detects emotion, drowsiness or fatigue of the baby from combination of determining facial expression, hand gesture, and heart rate or breathing rate In a further aspect, a method to provide information or entertainment content for a person includes detecting when a person is alone in a car, adjusting a speech recognizer in the car to focus capturing speech from the person's position in the car; playing content in the car as requested by the person; when the person exits the car and enters a building, transferring the speech recognizer from the car to a building speech recognizer along with a current play state of the content; and resuming playing the content on a device in the house on request without interruption.

Implementations can include one or more of the following. The transfer is based on data stored on a mobile device. Data on resume point is communicated over a wireless network connecting the car to the device. Data being transferred includes resume point of texting, social network communication, email, or chat. Data being transferred includes resume point of in a word processor, a software application, an augmented reality, or a virtual reality application. The person can play AR/VR content. The person can exercise in the car. The seat in the car can swivel to provide two rows of facing seats. The car can be shared, wherein the sharing can be based on a selected time of day, with peak hours more expensive than off-peak hours, and wherein the sharing can be based on a selected time period, similar to vacation timesharing to enable user to try different cars, or experience exotic vehicles one week a year. The system detects emotion, drowsiness or fatigue from combination of determining facial expression, hand gesture, and heart rate or breathing rate. Based on the emotion, drowsiness or fatigue, system can alter response of systems in the car or building to adjust to user state.

In another aspect, a method to park a car includes using a mobile application to communicate with the car; sending a parking instruction to the car through the mobile application; moving the car to an open parking spot; applying a neural network to sensor data and parking the car; and upon a summon from the mobile application, autonomously driving from the parking spot to a person based on a position of the mobile application to pick up the person.

Implementations can include one or more of the following. The sensor can be a multi-focal camera and a radar on a front of the car. The radar on the front of the car can be a long range radar. The sensor can be a multi-focal camera and a lidar on a front of the car. The sensor can be a multi-focal camera on a front of the car and side cameras and rear cameras. The multi-focal camera can be trifocal camera. One or more thermal cameras can be positioned on the car to detect objects at dusk or night. The sensor can be sonar sensors on the side or rear of the car to detect a stationary obstacle or vacant spot. The lidar can be part of the camera. The sensors can generate a 3D model of an environment. The 3D model can be a high definition map. The car can have an extendable jack with rolling wheels at the bottom to facilitate lateral parking movement into a tight parking spot as guided by side sensors including sonar and camera sensors.

In yet another aspect, a car includes a lidar or long-range radar in a front of the car; a multi-focal camera in the front; one or more thermal imager(s) in the front or rear of the car; a processor coupled to the lidar, radar, multi-focal camera and thermal imagers, the processor running a plurality of trained neural networks for navigation; side cameras, side sonars or side radars coupled to the processor for blind spot detection, rear traffic alert, and parking; and rear cameras, rear sonars or rear radars coupled to the processor for blind spot detection, rear traffic alert, and parking.

Implementations may include one or more of the following. The processor determines lane boundaries and perform automatic steering when lane changing. The processor determines lane boundaries and perform automatic parking. The processor determines lane boundaries and perform autonomous Pedestrian and Cyclist Braking. The car includes a cabin camera facing a driver to determine attentiveness. The cabin camera performs one of driver authorization, gaze detection, eye tracking and texting detection, or occupant monitoring. A wireless transceiver can also face the driver to detect heart rate or respiratory rate. The multi-focal camera includes a lens receiving liquid to change a focal length of the lens. The multi-focal camera includes three lenses each with different focal length. The car can have an extendable rolling wheels at the bottom to facilitate lateral parking movement into the parking spot as guided by side sensors including sonar and camera sensors. The system detects emotion, drowsiness or fatigue from combination of determining facial expression, hand gesture, and heart rate or breathing rate. Based on the emotion, drowsiness or fatigue, system can increase sensitivity to Traffic Signal Recognition, Lane Departure Warning, Collision Detection, Pedestrian Detection.

In yet another aspect, a method for navigation includes using a trained neural network to make driving decisions for an autonomous car; conforming to one or more traffic rules on driving speed or lane changing, and reasonably ignoring the one or more traffic rules during an imminent accident, wherein a reasonableness of the overruling is determined by featurizing a plurality of vehicle sensor parameters and traffic and weather conditions, and applying a law neural network trained on traffic case law or legal precedent to make the reasonableness decision.

The method includes assessing a driver or a manufacturer of the vehicle liable for the accident if the car was driven unreasonably. The method includes understanding the environment around vehicle. The method includes understanding behaviors of people encountered. The method includes deciding a response to the people. The method includes communicating with nearby people through audio or visual responses. The processor determines lane boundaries and perform automatic steering when lane changing. The processor determines lane boundaries and perform automatic parking. The processor determines lane boundaries and perform autonomous Pedestrian and Cyclist Braking. The car includes a cabin camera facing a driver to determine attentiveness. The cabin camera performs one of driver authorization, gaze detection, eye tracking and texting detection, or occupant monitoring. A wireless transceiver faces the driver to detect heart rate or respiratory rate. The multi-focal camera includes a lens receiving liquid to change a focal length of the lens. The multi-focal camera includes three lenses each with different focal length. System detects emotion, drowsiness or fatigue from combination of determining facial expression, hand gesture, and heart rate or breathing rate. Based on the emotion drowsiness or fatigue, system can increase sensitivity to Traffic Signal Recognition, Lane Departure Warning, Collision Detection, Pedestrian Detection. The reasonableness is determined by analyzing similar vehicle actions in similar location. The reasonableness is based on the then state of the art machine learning capability. The reasonableness is based on a reasonable person standard and based on the then state of the art machine learning standard. The system can adjust reasonableness standard to Traffic Signal Recognition, Lane Departure Warning, Collision Detection, Pedestrian Detection.

In another aspect, a method for cost-effective navigation of a vehicle in a metropolitan (metro) area, includes capturing images from a plurality of cameras in the vehicle; recognizing objects from the images using one or more neural networks; providing an accelerometer to perform position determination with dead-reckoning; providing position coordinates from a global positioning system; receiving positioning coordinates from a low latency cellular or wifi transceiver positioned at a known position; and generating a travel path for the vehicle in the metro area.

Implementations can include one or more of the following with supplemental sensors on the cellular or wifi transceiver. The sensor can be a multi-focal camera and a radar on a front of the car. The radar can be a long-range radar. The sensor can be a multi-focal camera and a lidar of the car. The sensor can be a multi-focal camera on a front of the car and side cameras and rear cameras. The multi-focal camera can be trifocal camera. One or more thermal cameras can detect objects at dusk or night. The sensor can be sonar sensors to detect a stationary obstacle or vacant spot. The lidar can be part of the camera. The sensors can generate a 3D model of an environment. The 3D model can be a high definition map. Vehicle can include in vehicle camera with Wifi that detects emotion, drowsiness or fatigue from combination of determining facial expression, hand gesture, and heart rate or breathing rate. Based on the emotion, drowsiness or fatigue, system can adjust Traffic Signal Recognition, Lane Departure Warning, Collision Detection, Pedestrian Detection. The result is a cost-effective car with expensive sensors mounted in the road infrastructure for shared access, so consumers are willing to switch to driverless. In the near term, with the technology still at tens of thousands of dollars, only a ride-hailing business will be financially sustainable. The local transceiver categorizes different features such as intersections, driveways, or fire hydrants. As more and more self-driving cars hit the road, they will constantly be encountering new objects and obstacles that they can relay to the mapping team and update other cars.

In another aspect, a method for cost-effective navigation of a vehicle in a metropolitan (metro) area includes capturing images from a plurality of cameras in the vehicle; recognizing objects from the images using one or more neural networks; providing an accelerometer to perform position determination with dead-reckoning; providing position coordinates from a global positioning system; receiving positioning coordinates from a low latency cellular or wifi transceiver positioned at a known position; and generating a travel path for the vehicle in the metro area.

Implementations can include one or more of the following with supplemental sensors on the cellular or wifi transceiver. The sensor can be a multi-focal camera and a radar on a front of the car. The radar can be a long range radar. The sensor can be a multi-focal camera and a lidar of the car. The sensor can be a multi-focal camera on a front of the car and side cameras and rear cameras. The multi-focal camera can be trifocal camera. One or more thermal cameras can detect objects at dusk or night. The sensor can be sonar sensors to detect a stationary obstacle or vacant spot. The lidar can be part of the camera The sensors can generate a 3D model of an environment. The 3D model can be a high definition map.

Vehicle can include in vehicle camera with Wifi that detects emotion, drowsiness or fatigue from combination of determining facial expression, hand gesture, and heart rate or breathing rate. Based on the emotion, drowsiness or fatigue, system can adjust Traffic Signal Recognition, Lane Departure Warning, Collision Detection, Pedestrian Detection. The system detects when car owners modify their own vehicles to improve performance and inadvertently compromise the computers' decision-making ability.

The result is a cost-effective car with expensive sensors mounted in the road infrastructure for shared access, so consumers are willing to switch to driverless. In the near term, with the technology still at tens of thousands of dollars, only a ride-hailing business will be financially sustainable. The local transceiver categorizes different features such as intersections, driveways, or fire hydrants.

BRIEF DESCRIPTION OF THE DRAWINGS

FIG. 2C illustrates an exemplary gesture control subsystem in the system of FIGS. 2A-2B;

FIG. 3 shows an exemplary child or animal safety protection process;

FIG. 4 shows an exemplary drunk driving protection process;

FIG. 16 is a diagram 600 illustrates generally, an overview of preferences matching by the server 202, according to embodiments disclosed herein;

DESCRIPTION

Figure 1:
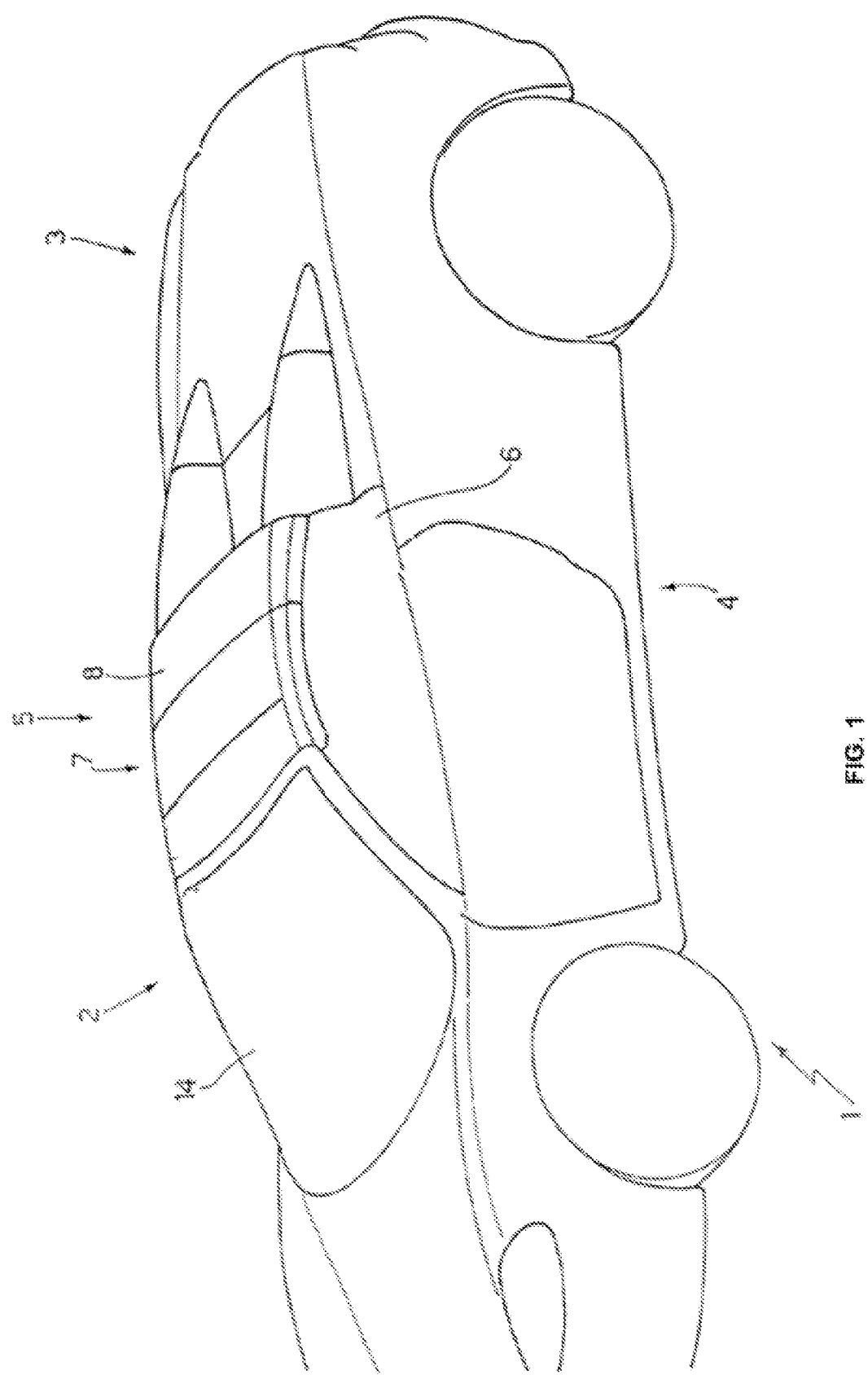
FIG. 1 shows an exemplary smart and safe vehicle.

FIG. 1 shows an exemplary environmentally friendly vehicle such as a car 1 with a passenger compartment 2 and a central engine compartment 3 behind passenger compartment 2 with a front window 14 and one or more side windows and a rear window. Although the engine compartment 3 is shown as a rear-engine, the engine compartment 3 can also be a front engine compartment. The engine can be all electric engine, hydrogen engine, hybrid engine, or an ultra low emission gas engine. A frame 4 of the car 1 supports a roof 5 which can be a sun roof that can expose the passenger compartment 2 in an open position and can cover the passenger when closed. To support the sun roof, the frame 4 provides two vertical posts 6 facing each other on opposite sides of car 1, at the boundary between passenger compartment 2 and engine compartment 3. When sun roof 5 is in the closed position, roof members 7 and 8 are substantially horizontal, substantially coplanar, and positioned seamlessly one behind the other. The car contains a cooling system that minimizes the weight and power consumption of conventional air conditioning system for the car 1.

Figure 2A:
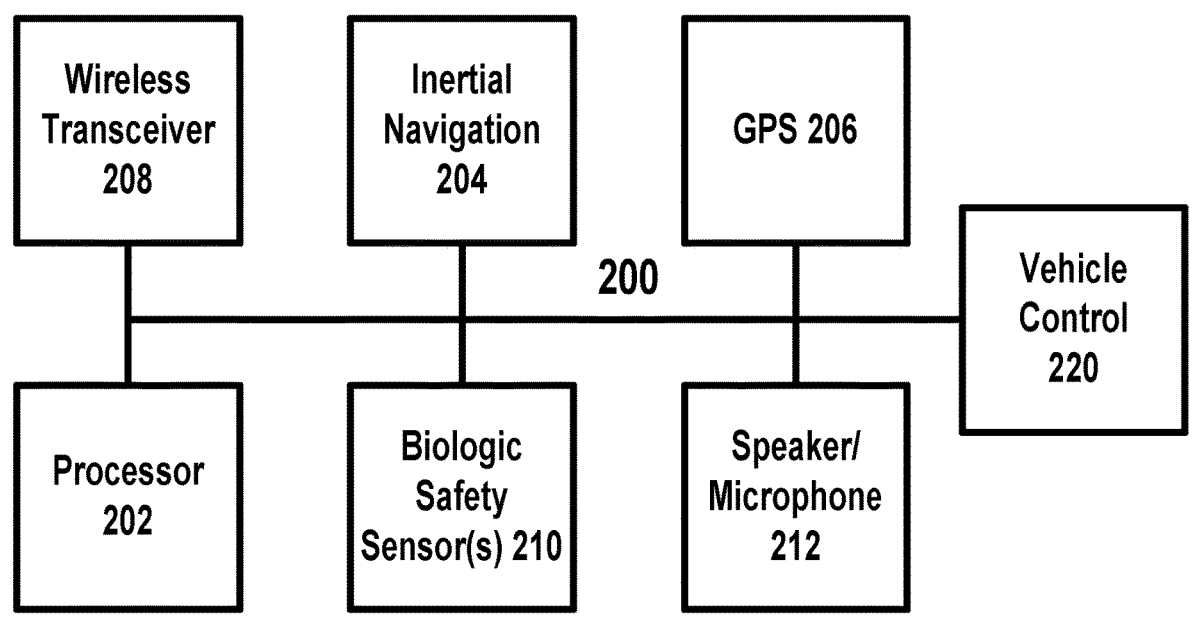
FIG. 2A shows an exemplary car electronic system.

FIG. 2A shows a block diagram of an embodiment of an electrical power and automobile control system that includes passenger protection. The system is controlled by a processor 202. The processor 202 is connected with an inertial system (INS) 204 and a global positioning system (GPS) receiver 206 that generate navigation information. The processor 202 is also connected with a wireless communication device 208 that transmits and receives digital data as well as being a Doppler radar when desired. The processor 202 drives a display 210 and a speaker 212 for alerting a driver. The processor 202 provides control inputs to the automobile's braking and steering systems 220. A power cable 200 carries power between the batteries 100-116 and an electric motor engine (not shown). The power cable 200 also carries power to recharge the batteries 100-116 serially or in parallel. The data can be provided to wireless transmitters that will wirelessly receive the signal and send the data on to computer stations. Exemplary protocols that can be used include CAN-bus, LIN-bus over power line (DC-LIN), and LonWorks power line based control. In one embodiment, the protocol is compatible with the HomePlug specifications for home networking technology that connects devices to each other through the power lines in a home. Many devices have HomePlug built in and to connect them to a network all one has to do is to plug the device into the wall in a home with other HomePlug devices. In this way, when the vehicle is recharged by plugging the home power line to the vehicle connectors, automotive data is automatically synchronized with a computer in the home or office. This embodiment includes navigation systems, the INS 204 and the GPS receiver 206. Alternate embodiments may feature an integrated GPS and INS navigation system or other navigation system. The use of only an INS 204 or only a GPS receiver 206 as the sole source of navigation information is also contemplated. Alternatively, the wireless communication device 208 can triangulate with two other fixed wireless devices to generate navigation information. A biologics sensor 210 captures user biological signals and speaker/microphone 212 provides both visual and audio situational awareness information to a driver. Alternate embodiments may feature only a display 210 or only a speaker 212 as the sole source of information for the driver. Embodiments that interact directly with the braking and steering systems that provide no audio information to the driver are also contemplated. The braking and steering systems 220 may also be commanded by the processor 202. The processor 202 may command that the brakes be applied to prevent collision with a vehicle ahead or may provide a steering input to prevent the driver from colliding with a vehicle. The processor 202 may also issue braking or steering commands to minimize the damage resulting from a collision as discussed in United States Patent Application 20080091352, the content of which is incorporated by reference.

Figure 2B:
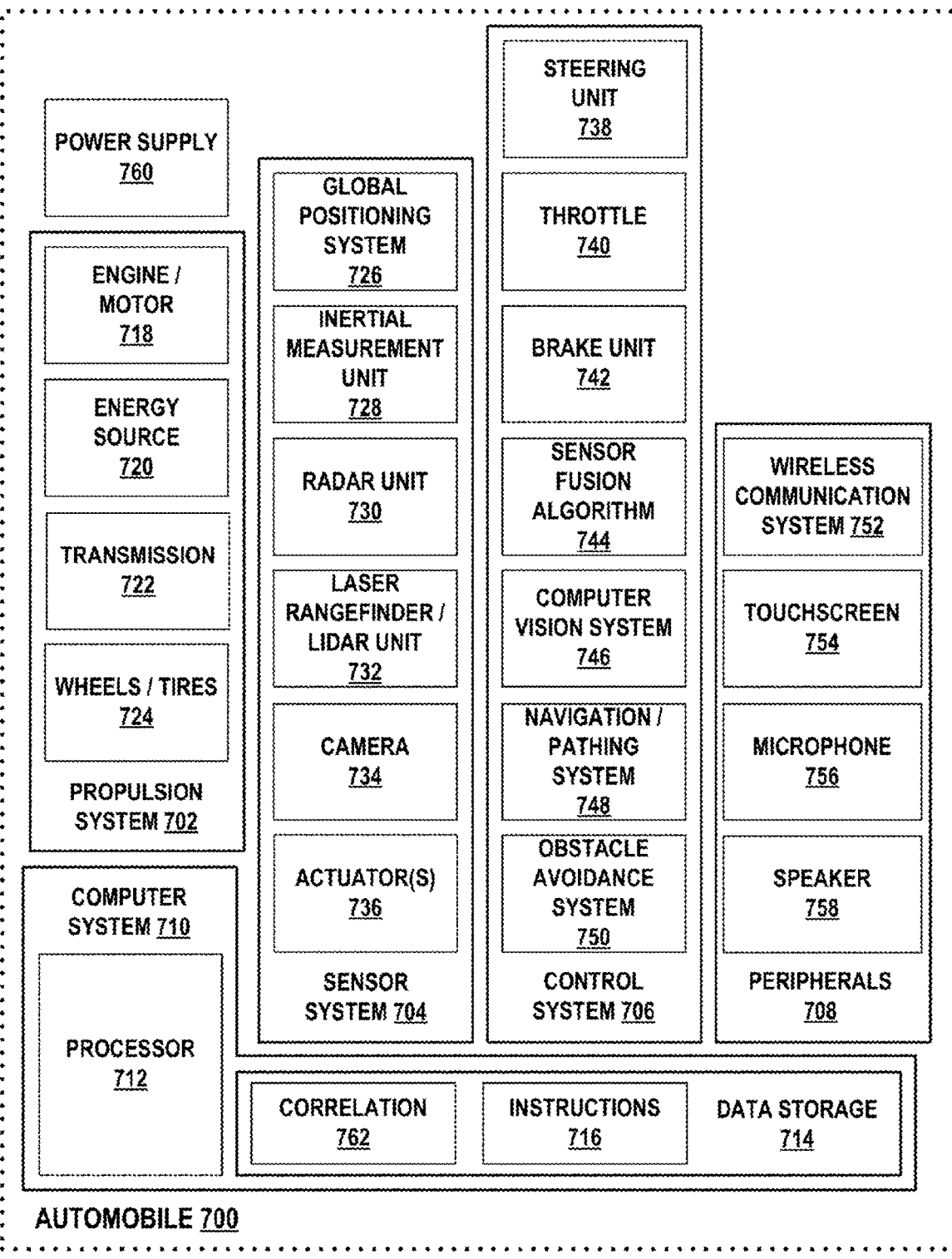
FIG. 2B illustrates another exemplary car electronic system.

FIG. 2B is a simplified block diagram of an example vehicle 700, in accordance with an embodiment. While the vehicle 700 in FIG. 7 is described as being configured to operate in an autonomous mode, in some embodiments the above methods may be implemented in a vehicle that is not configured to operate in an autonomous mode. In these embodiments, the vehicle may include fewer and/or different systems and/or components. The sensor system 704 may include a number of sensors configured to sense information about an environment in which the vehicle 700 is located, as well as one or more actuators 736 configured to modify a position and/or orientation of the sensors. As shown, the sensors of the sensor system include a Global Positioning System (GPS) 726, an inertial measurement unit (IMU) 728, a RADAR unit 730, a laser rangefinder and/or LIDAR unit 732, and a camera 734. The sensor system 704 may include additional sensors as well, including, for example, sensors that monitor internal systems of the vehicle 700 (e.g., an 02 monitor, a fuel gauge, an engine oil temperature, etc.). Other sensors are possible as well. The GPS 726 may be any sensor configured to estimate a geographic location of the vehicle 700. To this end, the GPS 726 may include a transceiver configured to estimate a position of the vehicle 700 with respect to the Earth. The GPS 726 may take other forms as well. The IMU 728 may be any combination of sensors configured to sense position and orientation changes of the vehicle 700 based on inertial acceleration. In some embodiments, the combination of sensors may include, for example, accelerometers and gyroscopes. Other combinations of sensors are possible as well. The RADAR 730 unit may be any sensor configured to sense objects in the environment in which the vehicle 700 is located using radio signals. In some embodiments, in addition to sensing the objects, the RADAR unit 730 may additionally be configured to sense the speed and/or heading of the objects. Similarly, the laser rangefinder or LIDAR unit 732 may be any sensor configured to sense objects in the environment in which the vehicle 700 is located using lasers. In particular, the laser rangefinder or LIDAR unit 732 may include a laser source and/or laser scanner configured to emit a laser and a detector configured to detect reflections of the laser. The laser rangefinder or LIDAR 732 may be configured to operate in a coherent (e.g., using heterodyne detection) or an incoherent detection mode. In one embodiment, a LIDAR-on-a-chip system steers its electronic beam using arrays of many small emitters that each put out a signal at a slightly different phase. The new phased array thus forms a synthetic beam that it can sweep from one extreme to another and back again 100,000 times a second. In one embodiment, each antenna, which consists of a silicon waveguide and five curved grooves etched in silicon, is 3 micrometers long, 2.8 µm wide, and 0.22 µm thick. An infrared laser beam is delivered to the antennas through a waveguide. The LIDAR 732 can be part of a camera 734. The camera 734 may be any camera (e.g., a still camera, a video camera, etc.) configured to record three-dimensional images of an interior portion of the vehicle 700. To this end, the camera 734 may be, for example, a depth camera. Alternatively or additionally, the camera 734 may take any of the forms described above in connection with the exterior camera 610. In some embodiments, the camera 734 may comprise multiple cameras, and the multiple cameras may be positioned in a number of positions on the interior and exterior of the vehicle 700. The control system 706 may be configured to control operation of the vehicle 700 and its components. To this end, the control system 706 may include a steering unit 738, a throttle 740, a brake unit 742, a sensor fusion algorithm 744, a computer vision system 746, a navigation or pathing system 748, and an obstacle avoidance system 750. The steering unit 738 may be any combination of mechanisms configured to adjust the heading of vehicle 700. The throttle 740 may be any combination of mechanisms configured to control the operating speed of the engine/motor 718 and, in turn, the speed of the vehicle 700. The brake unit 742 may be any combination of mechanisms configured to decelerate the vehicle 700. For example, the brake unit 742 may use friction to slow the wheels/tires 724. As another example, the brake unit 742 may convert the kinetic energy of the wheels/tires 724 to electric current. The brake unit 742 may take other forms as well. The sensor fusion algorithm 744 may be an algorithm (or a computer program product storing an algorithm) configured to accept data from the sensor system 704 as an input. The data may include, for example, data representing information sensed at the sensors of the sensor system 704. The sensor fusion algorithm 744 may include, for example, a Kalman filter, a Bayesian network, or another algorithm. The sensor fusion algorithm 744 may further be configured to provide various assessments based on the data from the sensor system 704, including, for example, evaluations of individual objects and/or features in the environment in which the vehicle 700 is located, evaluations of particular situations, and/or evaluations of possible impacts based on particular situations. Other assessments are possible as well.

The computer vision system 746 may be any system configured to process and analyze images captured by the camera 734 in order to identify objects and/or features in the environment in which the vehicle 700 is located, including, for example, traffic signals and obstacles (e.g., in embodiments where the camera 734 includes multiple cameras, including a camera mounted on the exterior of the vehicle 700). To this end, the computer vision system 746 may use an object recognition algorithm, a Structure from Motion (SFM) algorithm, video tracking, or other computer vision techniques. In some embodiments, the computer vision system 746 may additionally be configured to map the environment, track objects, estimate the speed of objects, etc. The navigation/path system 748 may be any system configured to determine a driving path for the vehicle 700. The navigation/path system 748 may additionally be configured to update the driving path dynamically while the vehicle 700 is in operation. In some embodiments, the navigation and path system 748 may be configured to incorporate data from the sensor fusion algorithm 744, the GPS 726, and one or more predetermined maps so as to determine the driving path for the vehicle 700. The obstacle avoidance system 750 may be any system configured to identify, evaluate, and avoid or otherwise negotiate obstacles in the environment in which the vehicle 700 is located. The control system 706 may additionally or alternatively include components other than those shown. Peripherals 708 may be configured to allow the vehicle 700 to interact with external sensors, other vehicles, and/or a user. To this end, the peripherals 708 may include, for example, a wireless communication system 752, a touchscreen 754, a microphone 756, and/or a speaker 758.

The wireless communication system 752 may take any of the forms described above. In one embodiment, it can be the Dedicated Short Range Communications (DSRC) which provides the communications-based active safety systems. DSRC communications take place over a dedicated 75 MHz spectrum band around 5.9 GHz, allocated by the US Federal Communications Commission (FCC) for vehicle safety applications. In contrast to WiFi, DSRC can accommodate an extremely short time in which devices must recognize each other and transmit messages to each other. A large number of these safety applications require response times measured in milliseconds. DSRC is targeted to operate in a 75 MHz licensed spectrum around 5.9 GHz, as opposed to IEEE 802.11a that is allowed to utilize only the unlicensed portions in the frequency band. DSRC is meant for outdoor high-speed vehicle (up to 120 mph) applications, as opposed to IEEE 802.11a originally designed for indoor WLAN (walking speed) applications. In IEEE 802.11a, all PHY parameters are optimized for the indoor low-mobility propagation environment. Communications-based active safety applications use vehicle-to-vehicle (V2V) and vehicle-to-infrastructure (V2I) short-range wireless communications to detect potential hazards in a vehicle's path—even those the driver does not see. The connected vehicle provides enhanced awareness at potentially reduced cost, and offers additional functionality over autonomous sensor systems available on some vehicles today. Communications-based sensor systems provide a low-cost means of enabling hazard detection capability on all vehicle classes, but requires vehicles and infrastructure to be outfitted with interoperable communications capabilities of DSRC or similar Vehicle to Vehicle networks.

The car can have a low latency 5G transceiver that communicates to a cell tower, and processing resources such as GPU and array processors near the cell tower can provide high speed shared compute power to the car through the 5G network. For example, the 5G network can have millimeter transceiver such as a low latency ultra-wide-band transceiver in communication with the processor and a remote processor can receive/send data to the transceiver to offload processing from the processor. Such extra power can be useful in AR/VR applications with surround 8k videos processed as 360 degree videos. The extra power can be used for road side recognition of objects, and for generating high definition maps as the car drives through an area with construction and changed from the last HD map, for example.

The touchscreen 754 may be used by a user to input commands to the vehicle 700. The microphone 756 may be configured to receive audio (e.g., a voice command or other audio input) from a user of the vehicle 700. Similarly, the speakers 758 may be configured to output audio to the user of the vehicle 700. Still further, while the above description focused on a vehicle 700 configured to operate in an autonomous mode, in other embodiments the vehicle may not be configured to operate in an autonomous mode. In these embodiments, for example, one or more of the following components may be omitted: the global positioning system 726, the inertial measurement unit 728, the RADAR unit 730, the laser rangefinder or LIDAR unit 732, the actuators 736, the sensor fusion algorithm 744, the computer vision system 746, the navigation or path system 748, the obstacle avoidance system 750, the wireless communication system 752, the touchscreen 754, the microphone 756, and the speaker 758.

Gesture Sensor for Vehicular Control

FIG. 2C shows an exemplary gesture recognition system. The system takes advantage of the numerous cameras onboard the vehicle for navigation and mapping purposes, and additionally includes the gesture control feature. System 800 includes a pair of cameras 802, 804 coupled to an image-analysis system 806. Cameras 802, 804 can be any type of camera, including cameras sensitive across the visible spectrum or, more typically, with enhanced sensitivity to a confined wavelength band (e.g., the infrared (IR) or ultraviolet bands); more generally, the term "camera" herein refers to any device (or combination of devices) capable of capturing an image of an object and representing that image in the form of digital data. For example, line sensors or line cameras rather than conventional devices that capture a two-dimensional (2D) image can be employed. The term "light" is used generally to connote any electromagnetic radiation, which may or may not be within the visible spectrum, and may be broadband (e.g., white light) or narrowband (e.g., a single wavelength or narrow band of wavelengths).

Cameras 802, 804 are preferably capable of capturing video images (i.e., successive image frames at a constant rate of at least 15 frames per second), although no particular frame rate is required. The capabilities of cameras 802, 804 are not critical to the invention, and the cameras can vary as to frame rate, image resolution (e.g., pixels per image), color or intensity resolution (e.g., number of bits of intensity data per pixel), focal length of lenses, depth of field, etc. In general, for a particular application, any cameras capable of focusing on objects within a spatial volume of interest can be used. For instance, to capture motion of the hand of an otherwise stationary person, the volume of interest might be defined as a cube approximately one meter on a side.

System 800 also includes a pair of light sources 808, 810, which can be disposed to either side of cameras 802, 804, and controlled by image-analysis system 806. Light sources 808, 810 can be infrared light sources of generally conventional design, e.g., infrared light-emitting diodes (LEDs), and cameras 802, 804 can be sensitive to infrared light. Filters 820, 822 can be placed in front of cameras 802, 804 to filter out visible light so that only infrared light is registered in the images captured by cameras 802, 804. In some embodiments where the object of interest is a person's hand or body, use of infrared light can allow the motion-capture system to operate under a broad range of lighting conditions and can avoid various inconveniences or distractions that may be associated with directing visible light into the region where the person is moving. However, a particular wavelength or region of the electromagnetic spectrum is required.

It should be stressed that the foregoing arrangement is representative and not limiting. For example, lasers or other light sources can be used instead of LEDs. For laser setups, additional optics (e.g., a lens or diffuser) may be employed to widen the laser beam (and make its field of view similar to that of the cameras). Useful arrangements can also include short- and wide-angle illuminators for different ranges. Light sources are typically diffuse rather than specular point sources; for example, packaged LEDs with light-spreading encapsulation are suitable.

In operation, cameras 802, 804 are oriented toward a region of interest 812 in which an object of interest 814 (in this example, a hand) and one or more background objects 816 can be present. Light sources 808, 810 are arranged to illuminate region 812. In some embodiments, one or more of the light sources 808, 810 and one or more of the cameras 802, 804 are disposed below the motion to be detected, e.g., where hand motion is to be detected, beneath the spatial region where that motion takes place. This is an optimal location because the amount of information recorded about the hand is proportional to the number of pixels it occupies in the camera images, the hand will occupy more pixels when the camera's angle with respect to the hand's "pointing direction" is as close to perpendicular as possible. Because it is uncomfortable for a user to orient his palm toward a screen, the optimal positions are either from the bottom looking up, from the top looking down (which requires a bridge) or from the screen bezel looking diagonally up or diagonally down. In scenarios looking up there is less likelihood of confusion with background objects (clutter on the user's desk, for example) and if it is directly looking up then there is little likelihood of confusion with other people out of the field of view (and also privacy is enhanced by not imaging faces). Image-analysis system 806, which can be, e.g., a computer system, can control the operation of light sources 808, 810 and cameras 802, 804 to capture images of region 812. Based on the captured images, image-analysis system 806 determines the position and/or motion of object 814.

For example, as a step in determining the position of object 814, image-analysis system 806 can determine which pixels of various images captured by cameras 802, 804 contain portions of object 814. In some embodiments, any pixel in an image can be classified as an "object" pixel or a "background" pixel depending on whether that pixel contains a portion of object 814 or not. With the use of light sources 808, 810, classification of pixels as object or background pixels can be based on the brightness of the pixel. For example, the distance (rO) between an object of interest 814 and cameras 802, 804 is expected to be smaller than the distance (rB) between background object(s) 816 and cameras 802, 804. Because the intensity of light from sources 808, 810 decreases as $1/r^2$, object 814 will be more brightly lit than background 816, and pixels containing portions of object 814 (i.e., object pixels) will be correspondingly brighter than pixels containing portions of background 816 (i.e., background pixels). For example, if rB/rO=2, then object pixels will be approximately four times brighter than background pixels, assuming object 814 and background 816 are similarly reflective of the light from sources 808, 810, and further assuming that the overall illumination of region 812 (at least within the frequency band captured by cameras 802, 804) is dominated by light sources 808, 810. These assumptions generally hold for suitable choices of cameras 802, 804, light sources 808, 810, filters 810, 812, and objects commonly encountered. For example, light sources 808, 810 can be infrared LEDs capable of strongly emitting radiation in a narrow frequency band, and filters 810, 812 can be matched to the frequency band of light sources 808, 810. Thus, although a human hand or body, or a heat source or other object in the background, may emit some infrared radiation, the response of cameras 802, 804 can still be dominated by light originating from sources 808, 180 and reflected by object 814 and/or background 816.

In this arrangement, image-analysis system 806 can quickly and accurately distinguish object pixels from background pixels by applying a brightness threshold to each pixel. For example, pixel brightness in a CMOS sensor or similar device can be measured on a scale from 0.0 (dark) to 1.0 (fully saturated), with some number of gradations in between depending on the sensor design. The brightness encoded by the camera pixels scales standardly (linearly) with the luminance of the object, typically due to the deposited charge or diode voltages. In some embodiments, light sources 808, 810 are bright enough that reflected light from an object at distance rO produces a brightness level of 1.0 while an object at distance rB=2rO produces a brightness level of 0.25. Object pixels can thus be readily distinguished from background pixels based on brightness. Further, edges of the object can also be readily detected based on differences in brightness between adjacent pixels, allowing the position of the object within each image to be determined. Correlating object positions between images from cameras 802, 804 allows image-analysis system 806 to determine the location in 3D space of object 814, and analyzing sequences of images allows image-analysis system 806 to reconstruct 3D motion of object 814 using conventional motion algorithms.

In identifying the location of an object in an image according to an embodiment of the present invention, light sources 808, 810 are turned on. One or more images are captured using cameras 802, 804. In some embodiments, one image from each camera is captured. In other embodiments, a sequence of images is captured from each camera. The images from the two cameras can be closely correlated in time (e.g., simultaneous to within a few milliseconds) so that correlated images from the two cameras can be used to determine the 3D location of the object. A threshold pixel brightness is applied to distinguish object pixels from background pixels. This can also include identifying locations of edges of the object based on transition points between background and object pixels. In some embodiments, each pixel is first classified as either object or background based on whether it exceeds the threshold brightness cutoff. Once the pixels are classified, edges can be detected by finding locations where background pixels are adjacent to object pixels. In some embodiments, to avoid noise artifacts, the regions of background and object pixels on either side of the edge may be required to have a certain minimum size (e.g., 2, 4 or 8 pixels).

In other embodiments, edges can be detected without first classifying pixels as object or background. For example, $\Delta\beta$ can be defined as the difference in brightness between adjacent pixels, and IAN above a threshold can indicate a transition from background to object or from object to background between adjacent pixels. (The sign of $\Delta\beta$ can indicate the direction of the transition.) In some instances where the object's edge is actually in the middle of a pixel, there may be a pixel with an intermediate value at the boundary. This can be detected, e.g., by computing two brightness values for a pixel i: $\beta L=(\beta i+\beta i-1)/2$ and $\beta R=(\beta i+\beta i+1)/2$, where pixel (i−1) is to the left of pixel i and pixel (i+1) is to the right of pixel i. If pixel i is not near an edge, $|\beta L-\beta R|$ will generally be close to zero; if pixel is near an edge, then $|\beta L-\beta R|$ will be closer to 1, and a threshold on $|\beta L-\beta R|$ can be used to detect edges.

In some instances, one part of an object may partially occlude another in an image; for example, in the case of a hand, a finger may partly occlude the palm or another finger Occlusion edges that occur where one part of the object partially occludes another can also be detected based on smaller but distinct changes in brightness once background pixels have been eliminated.

Detected edges can be used for numerous purposes. For example, as previously noted, the edges of the object as viewed by the two cameras can be used to determine an approximate location of the object in 3D space. The position of the object in a 2D plane transverse to the optical axis of the camera can be determined from a single image, and the offset (parallax) between the position of the object in time-correlated images from two different cameras can be used to determine the distance to the object if the spacing between the cameras is known.

Further, the position and shape of the object can be determined based on the locations of its edges in time-correlated images from two different cameras, and motion (including articulation) of the object can be determined from analysis of successive pairs of images. An object's motion and/or position is reconstructed using small amounts of information. For example, an outline of an object's shape, or silhouette, as seen from a particular vantage point can be used to define tangent lines to the object from that vantage point in various planes, referred to herein as "slices." Using as few as two different vantage points, four (or more) tangent lines from the vantage points to the object can be obtained in a given slice. From these four (or more) tangent lines, it is possible to determine the position of the object in the slice and to approximate its cross-section in the slice, e.g., using one or more ellipses or other simple closed curves. As another example, locations of points on an object's surface in a particular slice can be determined directly (e.g., using a time-of-flight camera), and the position and shape of a cross-section of the object in the slice can be approximated by fitting an ellipse or other simple closed curve to the points. Positions and cross-sections determined for different slices can be correlated to construct a 3D model of the object, including its position and shape. A succession of images can be analyzed using the same technique to model motion of the object. Motion of a complex object that has multiple separately In some embodiments, the pulsing of light sources 808, 110 can be used to further enhance contrast between an object of interest and background. In particular, the ability to discriminate between relevant and irrelevant (e.g., background) objects in a scene can be compromised if the scene contains object that themselves emit light or are highly reflective. This problem can be addressed by setting the camera exposure time to extraordinarily short periods (e.g., 800 microseconds or less) and pulsing the illumination at very high powers (i.e., 5 to 20 watts or, in some cases, to higher levels, e.g., 40 watts). This approach increases the contrast of an object of interest with respect to other objects, even those emitting in the same general band. Accordingly, discriminating by brightness under such conditions allows irrelevant objects to be ignored for purposes of image reconstruction and processing. Average power consumption is also reduced; in the case of 20 watts for 800 microseconds, the average power consumption is under 80 milliwatts. In general, the light sources 808, 110 are operated so as to be on during the entire camera exposure period, i.e., the pulse width is equal to the exposure time and is coordinated therewith. It is also possible to coordinate pulsing of lights 808, 810 for purposes of by comparing images taken with lights 808, 810 on and images taken with lights 808, 810 off.

Safety Handling

In one embodiment, the systems generally include at least one child seat sensor such as a weight sensor, a temperature sensor, an infrared sensor, a camera, or any other sensor that can sense the presence of a child in a child safety seat. For example, a weight sensor may be disposed at the base of the child safety seat, on either side of an optional seat cover, generally where the child's posterior would be disposed. Thus, the weight of the child would impinge on the sensor and indicate that the child is disposed in the car seat. A temperature sensor disposed in the same location would generally sense the temperature of the child. A threshold discriminator in the processor would then be employed to determine whether a child is disposed in the seat or not. An infrared sensor may also be employed to sense the temperature and thus the existence of the child. Other sensors may include a microphone, auditory sensors, smell sensors, or any other type of sensor that can sense the presence of a biologic in a vehicle. The trigger may sense conditions that are dangerous in the absence of a parent or caregiver as well as conditions that are dangerous even in the presence of a parent or caregiver, such as dangerous temperature (extreme heat or cold temperature) conditions, via use of temperature sensor.

The trigger can be a sensor that senses the operation of the vehicle, the temperature within the vehicle, or any other sensor that can determine if a deleterious condition exists for a child disposed therein. The trigger may include motion sensor such as accelerometer or wheel sensors to detect if the vehicle is moving without the driver. Other potential triggers include an engine noise sensor or engine heat sensor placed in the engine compartment of the vehicle. For both cases, a decrease in either may be recognized as the vehicle ceasing motion, and each would be convenient to retrofit, especially where such sensors are provided with a wireless communications capability. Many of the triggers disclosed above may also be convenient to retrofit. In some embodiments, multiple sensors are provided for redundancy. For example, if a parent or caregiver suffers an illness that makes response or other child care impossible, the other sensor can still cause an alarm. In a particular example, if the parent suffers a heart attack in the seat, a driver seat sensor would not cause an alarm. If, however, the temperature rises deleteriously, a redundant temperature sensor may still cause an alarm to occur.

The sensors can also detect driver impairment or failure, to help the driver to navigate safely. For example, the vehicle can detect that the driver has become incapacitated by a stroke and automatically come a complete stop at designated safety points. In addition to changing the way the vehicle brake, the vehicle may change the way it maneuvers in other ways as well, such as accelerating differently or changing directions. For instance, the vehicle may accelerate more slowly if the driver pulse rate is excessively high. The vehicle may also turn more or less tightly in order to reduce shock to the passengers. The vehicle may also use other systems and methods to determine the state of a vehicle driver. For example, the vehicle may monitor how far it takes the car to stop compared to expected braking distance. If the distance is longer than expected, such as taking longer than it has in the past, the computer system may determine that the brakes are worn and start braking earlier. The system and method may also estimate the state of a component based on its repair service record. In that regard, the processor may query data or an external database (e.g., a server with which the vehicle is in wireless communication) for medical records and get assistance.

Modeling of the patterns of changes in the driver's performance and conditions, as well as modeling of the patterns of changes in the driving environment, may be performed by the autonomous driving computer system. Alternatively, predetermined models may be stored in the autonomous driving system. The computer system may process the observed data, fit them into the 3D models in FIGS. 7A-7I, and issue compensation signals accordingly.

The vehicle may take the steps necessary to get medical assistance for the driver/passenger. By way of example, the vehicle may autonomously and without direct human assistance navigate to a hospital or medical clinic, notify the facility of the medical emergency, safely transferring the passenger and/or the driver to the medical facility and return to its original location when done.

Hand-Gesture Control of Vehicle

Figure 5:
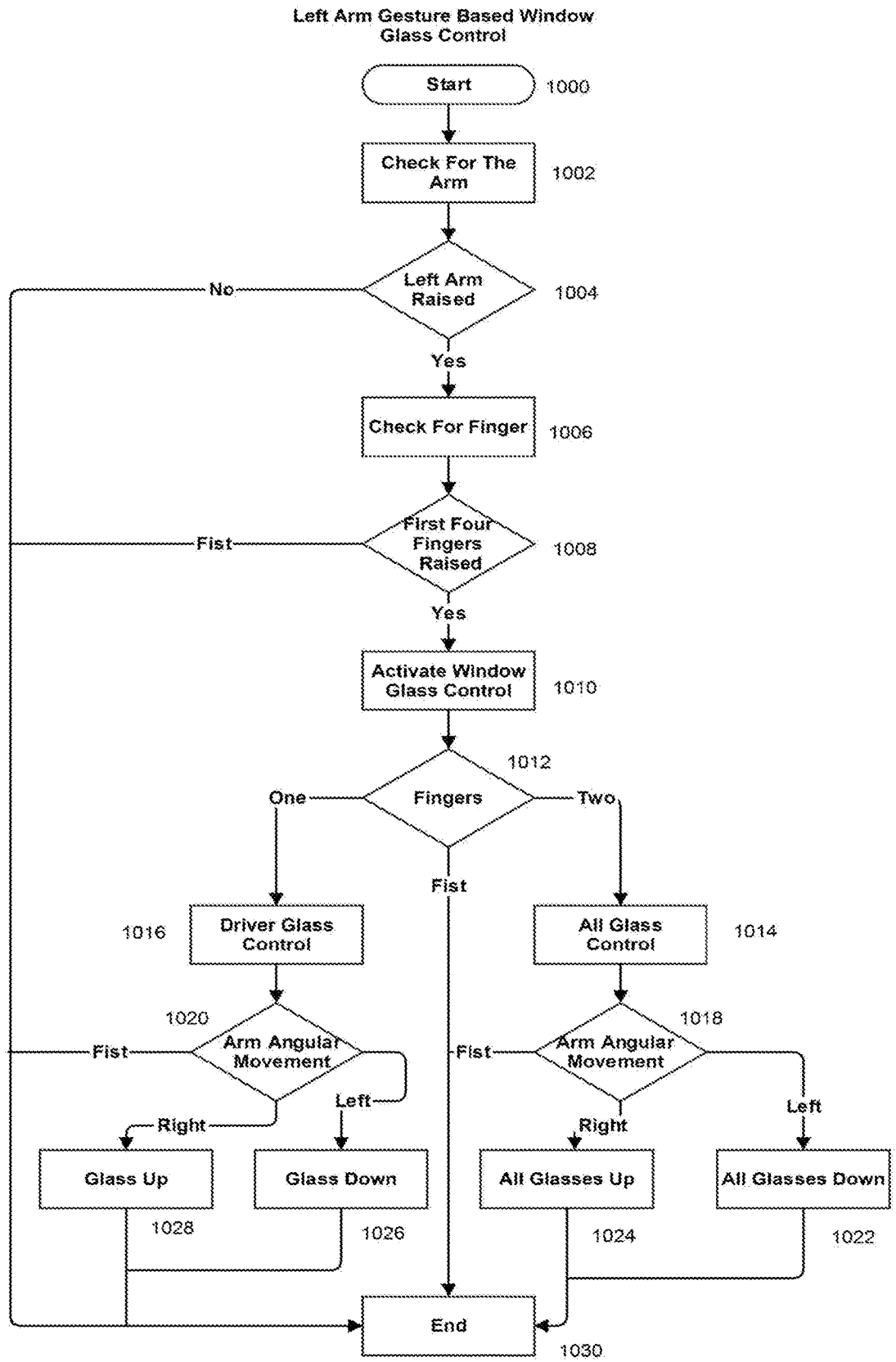
FIG. 5 shows exemplary gesture control of the car.

FIGS. 5A-5L show exemplary hand control of a smart vehicle. First, a Left Hand Gesture Based Car Control process is disclosed. FIG. 5A shows the left arm gesture based window glass control process. The process checks for the raised arm (1002). If the arm is raised (1004) it checks for the number of fingers raised (1006). The controls for windows are activated if first four fingers are raised (1008). The process allows controlling only the driver seat glass control and also all the window glass control. This decision is based on the number of fingers raised. A single finger chooses only driver glass. Movements of the glass is than controlled by the angular movement of the arm (1020), a right movement slides the glass up (1028) and a left movement slides it down (1026). The process is concluded (1030) after the windows are at the required position. At any moment the driver can choose to exit the process by forming a fist of his left arm.

FIG. 5B shows the flow for seat control process. The process is capable of controlling both the driver seat and the front passenger seat as well. The process starts with checking for which arm is raised (1036). After the arm the process scans for the fingers (1038), first 2 fingers initiate the seat actuators (1040). Now, the driver can choose to adjust his own seat or maybe the seat of the passenger. This decision is dependent whether one or two fingers are raised (1044). The seats can be moved forth or back as per the arms angular movement (1052) (1050). As per the convenience, the seats can be adjusted. After the adjustment is done, the process concludes (1062). At any point the process can be ended if the driver forms a fist on left hand.

FIG. 5C shows exemplary left hand based gesture based mechanism for unlocking the 'Hood' and the 'Trunk' of the car. As it is left arm based control, the mechanism uses a camera to check the arm raised. A raised left arm initiates the process which unlocks the hood and trunk (1068). The camera than checks for the fingers that are raised (1070), the first finger is used to activate the hood & trunk control (1072). To open the trunk the driver has to make a right angular movement (1076) and an opposite movement for unlocking the hood (1078). As soon as either of the two is unlocked the process ends (1082). If the process is started by mistake or confusion, the driver can choose to exit by forming a fist on his left arm.

FIG. 5D shows exemplary process for controlling temperature of the driver and front passenger seats. After checking for left raised arm (1088) the camera scans for the fingers raised (1090). The first three fingers are to be used by the driver to activate seat temperature controls (1092). The driver can choose to control his seat temperature or the passenger's seat temperature by raising the appropriate number of fingers (1096). The angular movements of the left arm can be used to increase or decrease the temperature of the selected seat (1104) (1102). The process can be ended after adjusting the temperature or at any other point by forming a fist (1114).

FIG. 5E is an example of a left arm gesture based navigation (GPS) control for a car. The process initializes when the driver raises his/her left arm (1120). The GPS system is activated if the all the fingers are raised i.e. an open palm (1124). Now the arm motion in the vertical and horizontal axis can be used to move the GPS pointer (1128). To select a particular destination, the pointer must be kept at the same location for a pre-defined duration of time (1144). Once the destination is set, the GPS starts routing (1146) and then exits the process (1148). The process can be ended abruptly if needed by forming a fist on left hand.

FIG. 5F shows an exemplary gesture based control of drivers mirror using left arm. The driver initiates the process by raising the left arm (1154). The thumb is used as a trigger for activating the mirror actuators (1158). To adjust the mirror angle, the driver can move his/her arm along the vertical or horizontal axis (1162). The driver can form a fist (1170) (1168) or wait for a predefined time interval to set the mirror angle (1182). This process has an option which enables the driver to exit anytime by forming a fist on left hand.

FIG. 5G shows an exemplary music control in the car using gestures of right hand. The process is activated if the camera scans a vertically standing right arm (1190). The car music system is initiated if the driver has an open right palm (1194). Depending upon the fingers raised after the music system is initiated either radio or just the MP3 player is started (1204). The angular movements of the arm can be used to switch between stations or songs (1206) (1202). Once the desired station or song is selected the driver can exit the process by forming a closed fist (1216). A closed fist formed anytime can be used to exit the process anytime.

FIG. 5H shows an exemplary car temperature control using gestures from the right arm. The driver is expected to raise the first two fingers of the right arm to activate the temperature controls (1246). The temperature controlling element is the angular motion of the right arm (1250). A left motion causes decrease in temperature and vice versa (1256) (1254). Once the desire temperature is achieved, the driver can stop the process by forming a fist. A fist basically exits the process at any given point.

FIG. 5I shows an exemplary control the car volume using arm gestures. The camera initiates the process whenever the driver raises his/her right arm (1222). The process expects the driver to raise three fingers to initiate volume control (1226). Using the right or left angular motion the volume can be increased and decreased (1230).

FIG. 5J shows an exemplary technique for sliding the sun roof by the means of hand gesture. The sun roof control process starts when the driver raises his/her right arm (1264) and first four fingers of the same (1268). The camera now scans for the angular motion of the arm (1272). A left motion pulls the roof back (1276) whereas a right motion pushes it forward so that it can be closed (1274). The process ends once the roof is entirely opened or closed and it can also be concluded by forming a fist on the right arm.

FIG. 5K shows an exemplary arm gesture based technique for controlling the car wind shield wipers. The wiper motors are activated when the right arm along with first finger is raised (1284) (1288). The speed of the wiper motors can be controlled using the right arm angular motion (1292). The left motion decreases the speed (1298), the right motion increases the wiper speed (1296) and in order to stop the wiper a still right arm with a closed fist should be scanned by the camera (1294).

FIG. 5L shows an exemplary right arm gesture based control of the rear view mirror. The camera scans for the right arm, if it is up the process is initiated (1306). The rear view mirror control is activated if the camera scans only a thumb on right arm (1310). Now, the rear view mirror can be adjusted vertically and horizontally, this is achieved by moving the arm with only raised thumb along the desired axis (1314). To lock the position of the mirror, the same position is to be maintained for a pre-defined interval of time. Once done the process locks the mirror and concludes (1332). The process can be ended anytime by the driver by forming a fist on his right arm.

In other embodiments, by cupping the hand on the an object such as a steering wheel, the user can use voice to make calls, receive and respond to texts, launch apps, get turn-by-turn directions, find the nearest Chinese restaurant and other local businesses, or say "Play me some Barry Manilow." You can also ask Siri or Google Now to search the Internet as you roll down the Interstate. The apps will be able to pull contacts directly from the phone's address book, access favorites and bookmarks, and have user location history close at hand.

A gesture is used to control an air conditioning system in an example vehicle, in accordance with an embodiment. As shown, a user 300 is driving the vehicle. The vehicle may maintain a correlation between a plurality of predetermined gestures, in combination with a plurality of predetermined regions of the vehicle, and a plurality of functions, such that each gesture in the plurality of predetermined gestures, in combination with a particular region of the plurality of predetermined regions, is associated with a particular function in the plurality of functions, as described above. For example, the correlation may include a downward swiping gesture in a region that includes an air-conditioning vent associated with the function of decreasing a fan speed of an air conditioning system. Other examples are possible as well.

As shown, a fan speed indicator on the display indicates that a fan speed of the air conditioning system in the vehicle is high. At some point, the user may wish to lower the fan speed of the air conditioning system. To this end, the user may make a downward swiping gesture in a region that includes an air-conditioning vent. The camera 304 may record three-dimensional images of the downward swiping gesture in the region that includes an air-conditioning vent. Based on the three-dimensional images, the vehicle may detect the downward swiping gesture in the region that includes the air-conditioning vent.

The vehicle may then select, based on the correlation, a function associated with the downward swiping gesture in the region that includes the air-conditioning vent. For example, the downward swiping gesture in the region that includes the air-conditioning vent may be associated with the function of decreasing a fan speed of the air conditioning system, as described above. Other examples are possible as well. Once the vehicle has selected the function from the correlation, the vehicle may initiate the function in the vehicle. That is, the vehicle may decrease the fan speed in the vehicle.

In some embodiments, the vehicle may additionally determine an extent determining an extent of the downward swiping gesture and may decrease the fan speed by an amount that is, for example, proportional to the extent.

In some embodiments, in addition to initiating the function, the vehicle may trigger a feedback to the user, such as an audible feedback, a visual feedback, and/or a haptic feedback. Such feedback may be particularly useful when the function is not immediately detectable by the user, such as a small decrease in the fan speed of the climate control system or a slight repositioning of a seat.

Further, in some embodiments, the vehicle may determine an extent of the given gesture. For example, if the given gesture is a swipe gesture, the vehicle may determine an extent of the swipe (e.g., how long the swipe is in space and/or time). The vehicle may then determine an operational parameter based on the extent. For example, for a greater extent, the vehicle may determine a greater operational parameter than for a lesser extent. The operational parameter may be, for example, proportional to, or approximately proportional to, the extent. In these embodiments, when the vehicle initiates the function the vehicle may initiate the function with the determined operational parameter.

For example, if the swipe gesture is in a region that includes a window, and the swipe gesture in the region that includes the window is associated with opening the window, the vehicle may determine an extent of the swipe and further may determine how far to open the window based on the extent of the swipe. For instance, the vehicle may open the window further for a longer swipe than for a shorter swipe.

As another example, if the swipe gesture is in a region that includes an air-conditioning vent, and the swipe gesture in the region that includes the air-conditioning vent is associated with lowering a temperature in the vehicle, the vehicle may determine an extent of the swipe and further may determine how much to lower the temperature in the vehicle based on the extent of the swipe. For instance, the vehicle may lower the temperature further for a longer swipe than for a shorter swipe.

Such an extent could be determined for gestures other than a swipe gesture as well. For example, if a tap gesture is in a region that includes a speaker, and the tap gesture in the region that includes the speaker is associated with lowering a volume of an audio system, the vehicle may determine an extent of the tap (e.g., how many taps, how long the tap is held, etc.) and further may determine how much to lower the volume of the audio system based on the extent of the tap. For instance, the vehicle may lower the volume more for more taps (or a longer tap) than for fewer taps (or a shorter tap).

In some embodiments, rather than determining the extent of the gesture and the corresponding operational parameter and then initiating the function with the determined operational parameter, the vehicle may instead continuously determine the extent of the gesture and update the corresponding operational parameter, and may continuously initiate the function with the updated operational parameter. For example, the vehicle may detect a cover gesture in a region that includes an air-conditioning vent (e.g., such that the air-conditioning vent is covered), and the cover gesture in the region that includes the air-conditioning vent may be associated with lowering a fan speed of the air conditioning system. Once the vehicle detects the cover gesture in the region that includes the air-conditioning vent, the vehicle may lower the fan speed (e.g., by a predetermined amount). As the vehicle continues to detect the cover gesture, the vehicle may continue to lower the fan speed (e.g., in increments of, for example, the predetermined amount, growing amounts, etc.). Once the vehicle detects that the cover gesture has ended, the vehicle may cease to lower the fan speed. As a result, during the cover gesture the vehicle may lower the fan speed by an amount that is based on the extent of the cover gesture.

In some embodiments, the vehicle may have difficulty detecting the given gesture and/or the given region. For example, the vehicle may determine that a confidence level of one or both of the given gesture and the given region is below a predetermined threshold. In these embodiments, the vehicle may request an occupant to repeat the given gesture in the given region. When the occupant repeats the given gesture in the given region, the vehicle may record additional three-dimensional images and may detect the given gesture and the given region based on the additional three-dimensional images (and, in some cases, the three-dimensional images previously recorded).

Obstacle Detection

In some embodiments, a vehicle identifies obstacles on the road, and the computer system may use one or more sensors to sense the obstacles. For example, the computer system may use an image-capture device to capture images of the road and may detect the obstacles by analyzing the images for predetermined colors, shapes, and/or brightness levels indicative of an obstacle. As another example, the computer system may project LIDAR to detect the obstacle. The computer system may estimate the location of the obstacle and control the vehicle to avoid the vehicle and yet maintain a predetermined distance from neighboring vehicles in both directions. Other vehicles behind the lead vehicle can then simply follow the lead vehicle as part of a flock. The computer system may then control the vehicle to maintain a distance between the vehicle and the at least one neighboring vehicle to be at least a predetermined minimum distance to avoid colliding with the at least one neighboring vehicle.

Figure 6A:
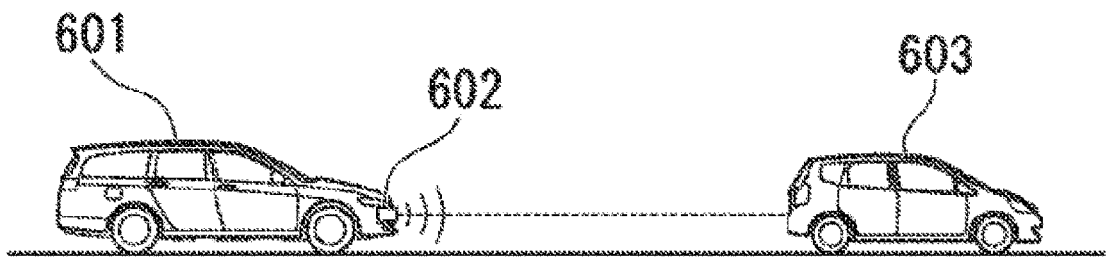
FIGS. 6A-6C show exemplary obstacles that may be encountered by vehicles.
Figure 6B:
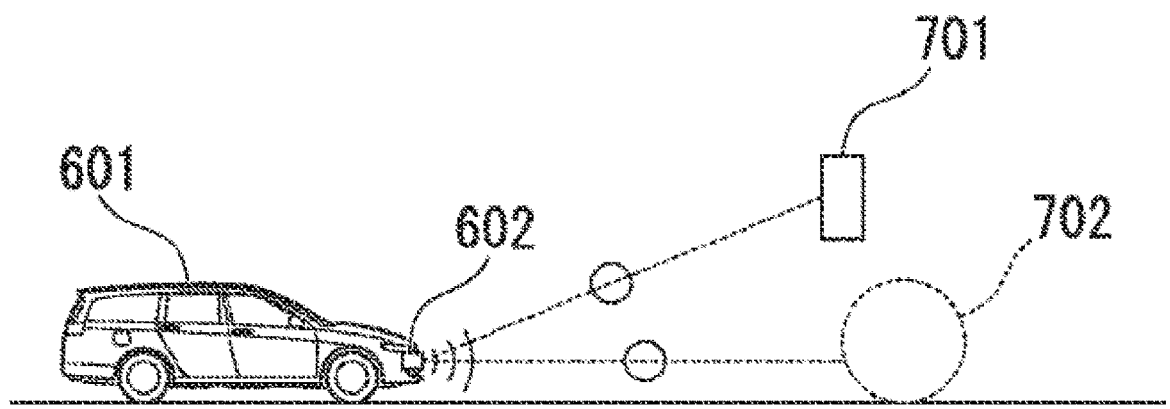
Figure 6C:
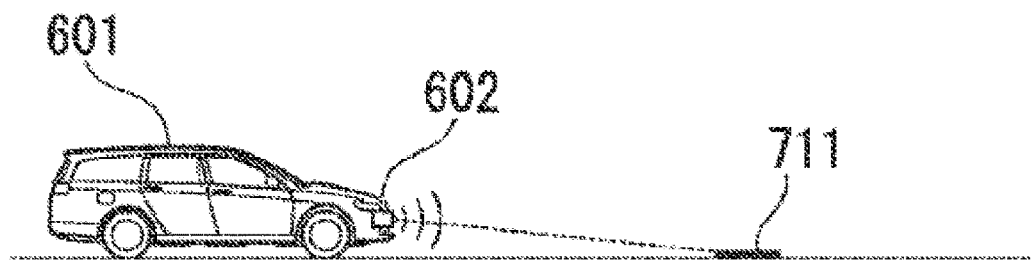
Figure 7A:
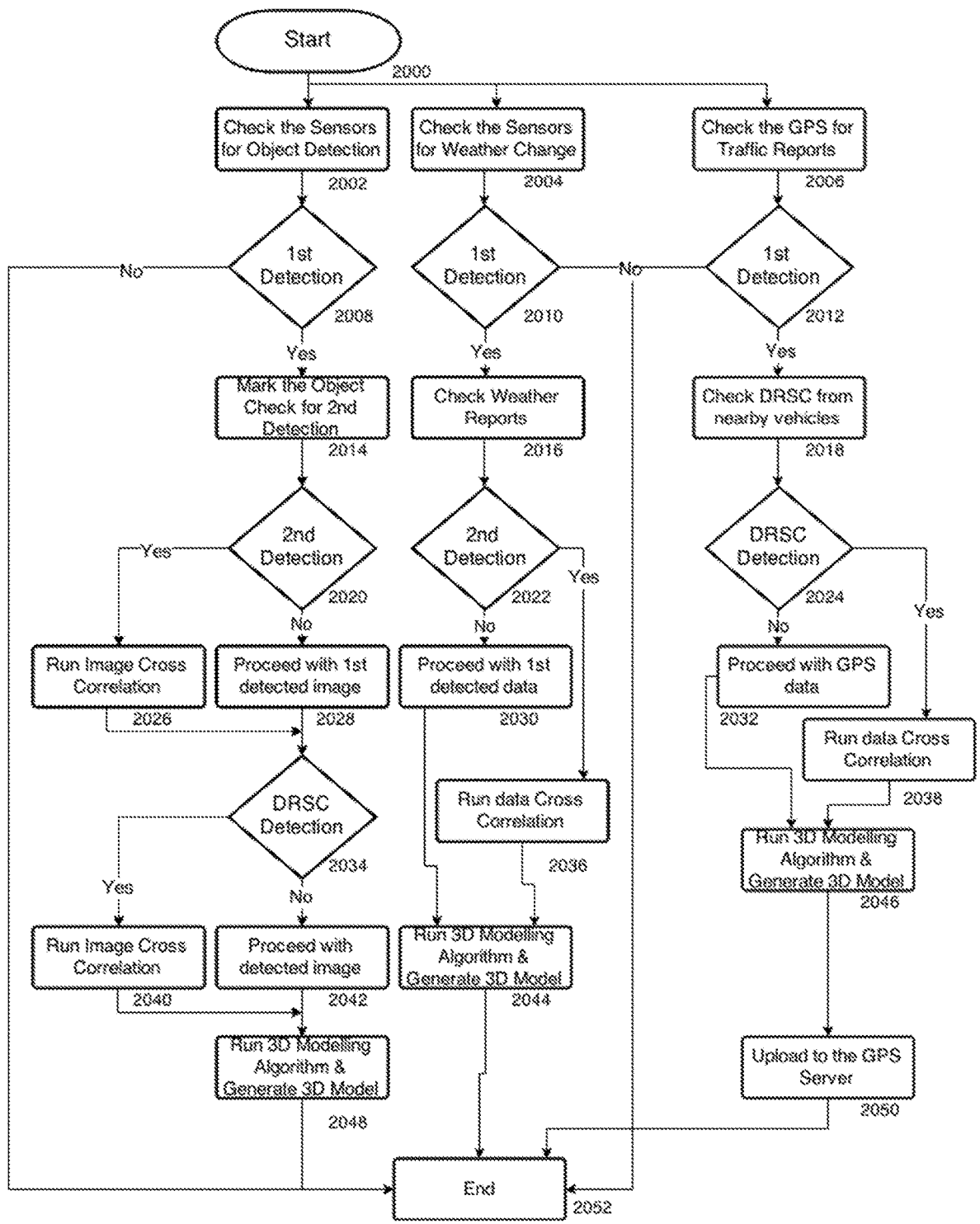
FIGS. 7A-7H illustrate an exemplary process to fuse data for 3D models used for car navigation.
Figure 7B:
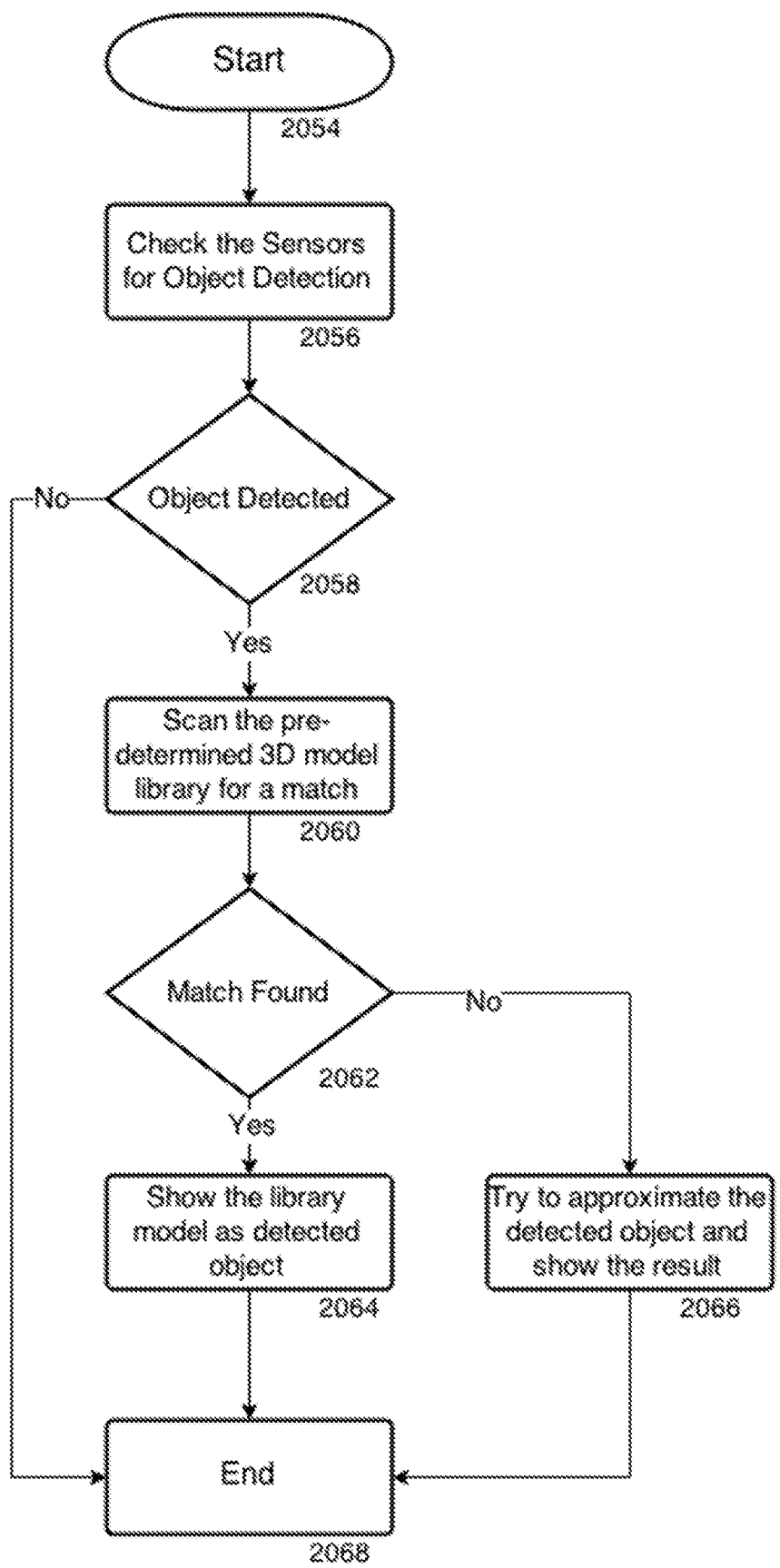
Figure 7C:
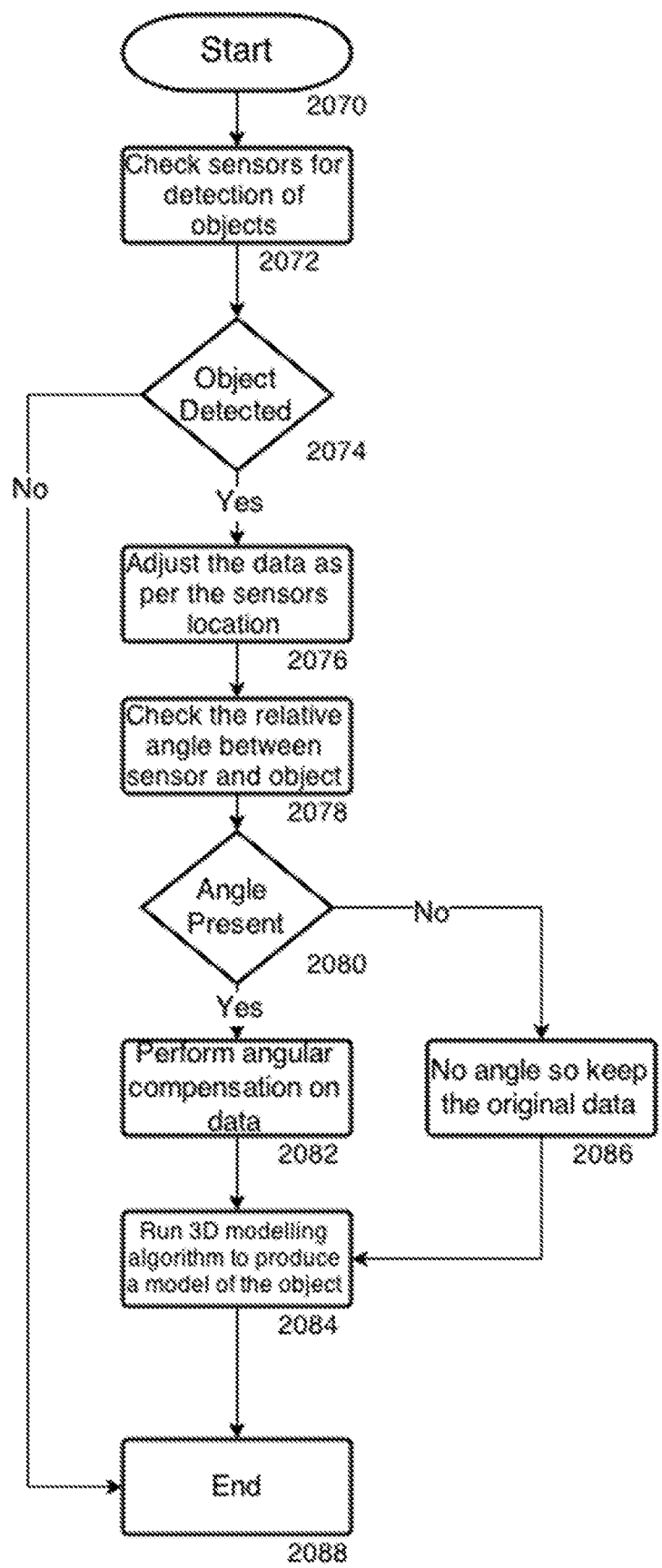
Figure 7D:
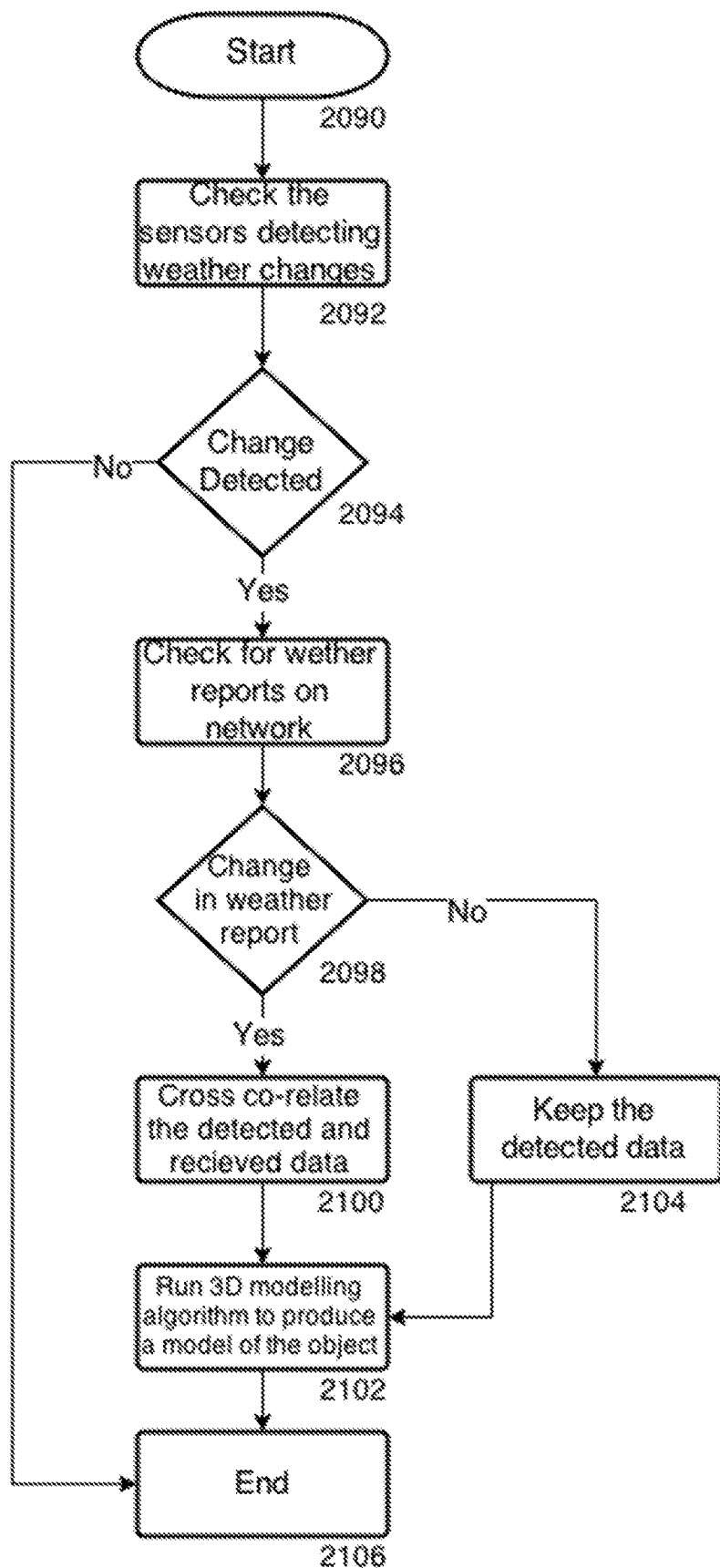
Figure 7E:
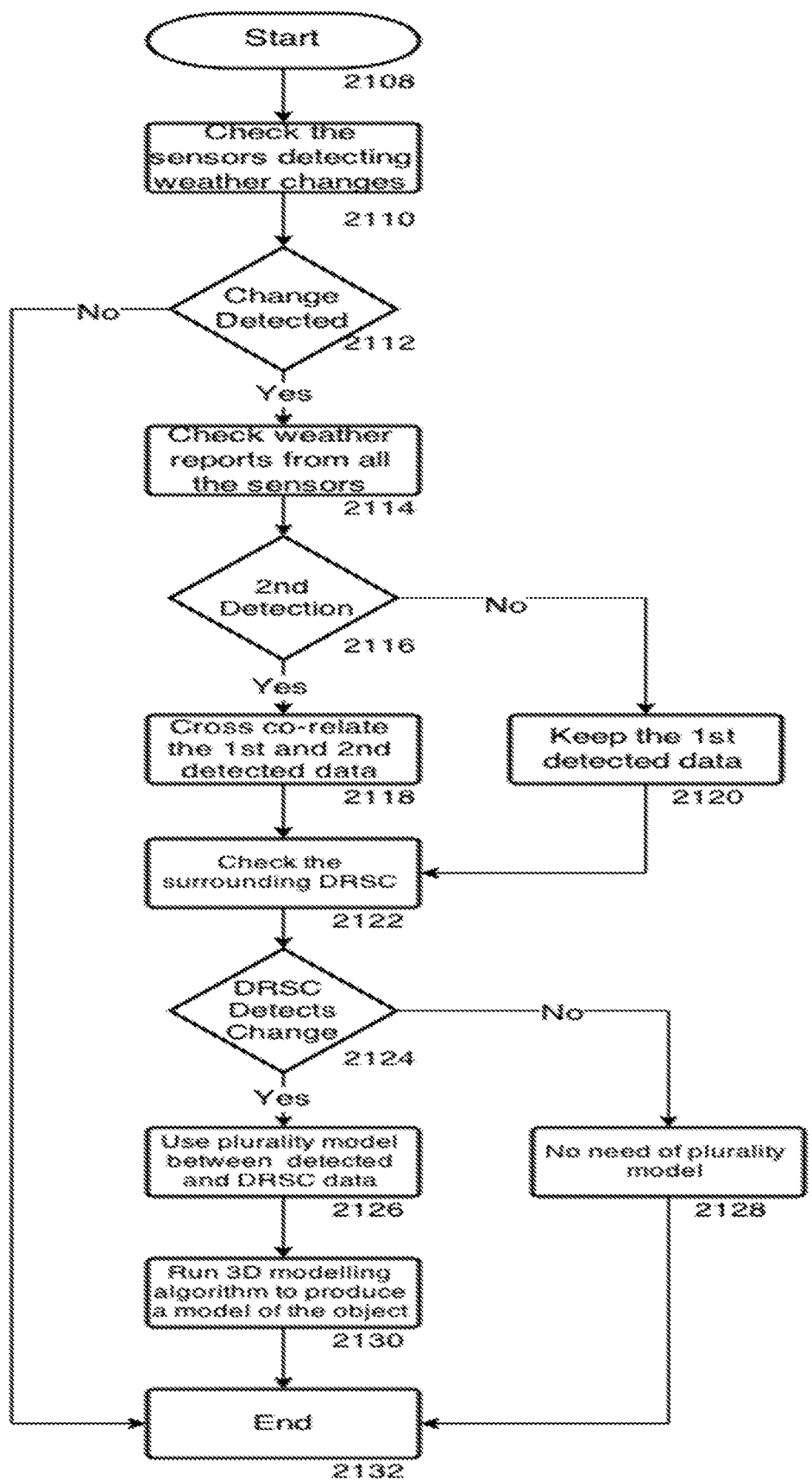
Figure 7F:
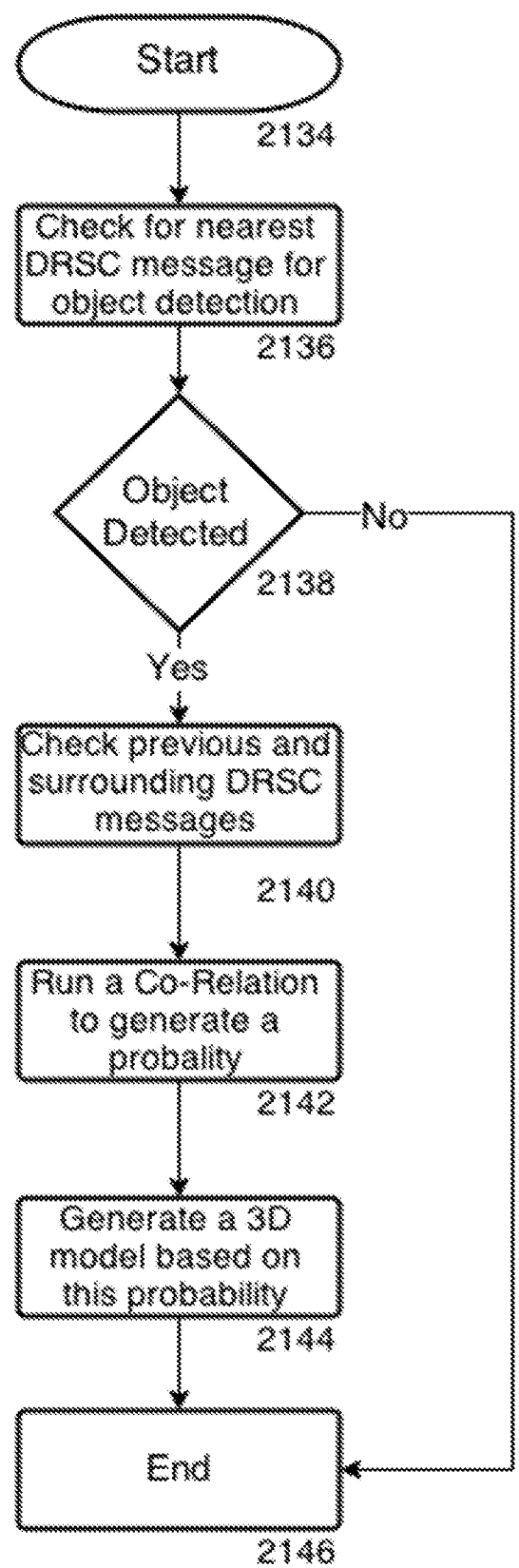
Figure 7G:
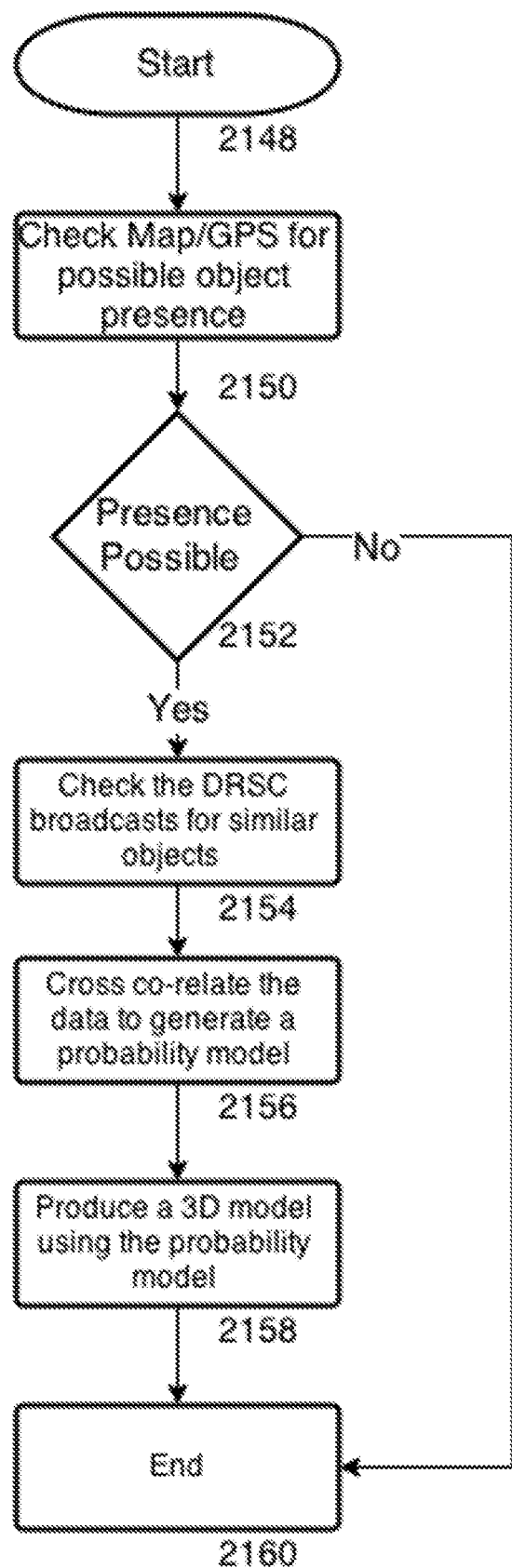
Figure 7H:
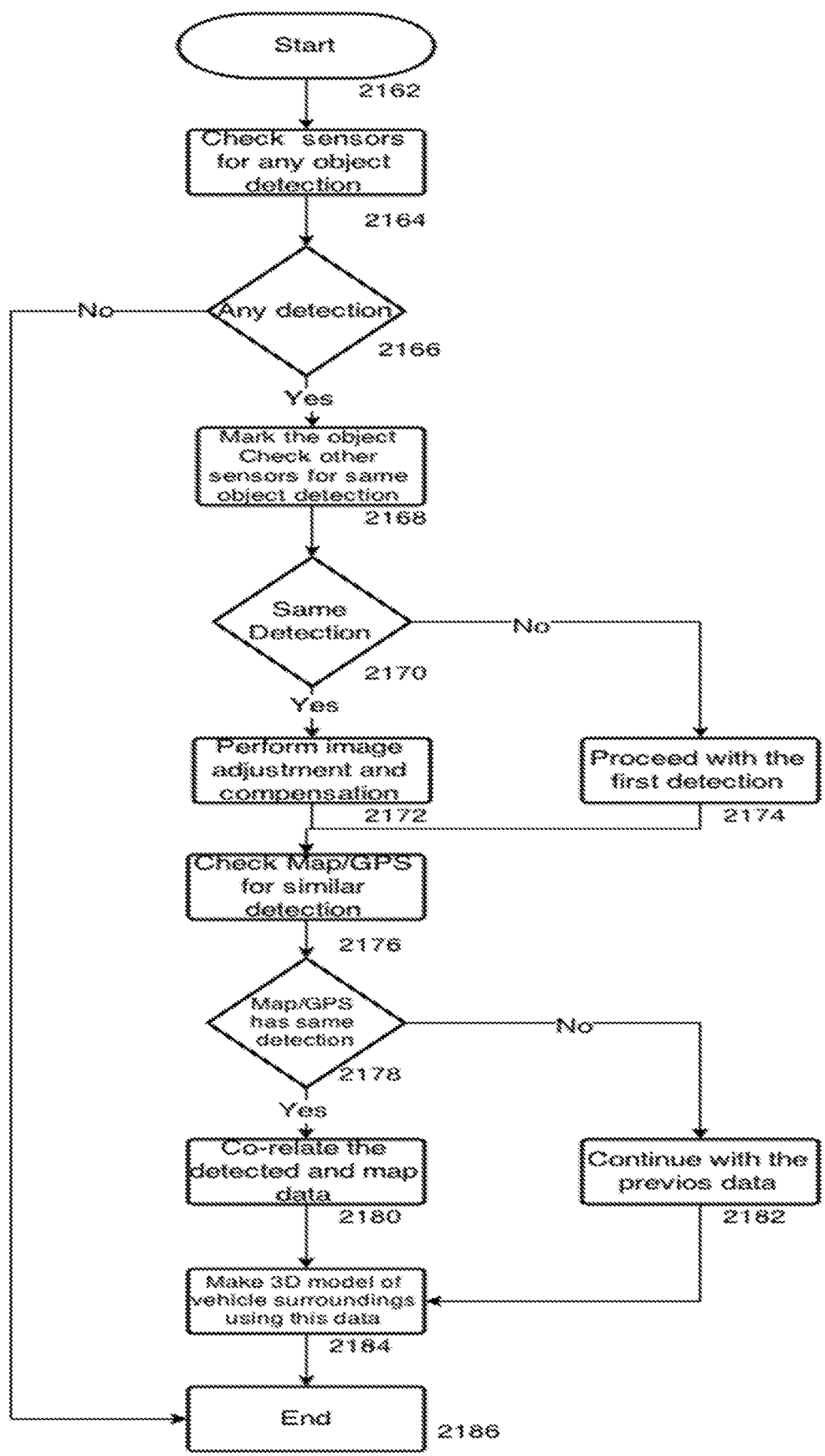

FIGS. 6A-6C show exemplary obstacles that may be encountered by vehicles. FIGS. 7A-7H illustrate an exemplary process to fuse data for 3D models used for car navigation. FIG. 7A shows an exemplary system that performs data fusion based on sensor based detection of objects, change in weather and traffic, and holiday/emergency conditions, among others. The process checks all the sensors for change in weather (2004), detection of object (2002) and the GPS for current traffic conditions (2006). For each given sensor for detecting objects in a vehicle's environment, the process generates a 3D model of the given sensor's field of view; obstacle information from front cars using vehicle-vehicle communication (DRSC); neighboring car driver preference information; traffic information including emergency information. The process can adjust one or more characteristics of the plurality of 3D models based on the received weather information to account for an impact of the actual or expected weather conditions on one or more of the plurality of sensors. After the adjusting, aggregating, by a processor, the plurality of 3D models to generate a comprehensive 3D model; combining the comprehensive 3D model with detailed map information; and using the combined comprehensive 3D model with detailed map information to maneuver the vehicle. In FIG. 7A, the process checks sensors for object detection (2008) and then checks for confirmations from other vehicles over V2V communication such as DSRC and then generates 3D model therefrom. The process can also check for weather change (2004) and correlate the weather change to generate an updated 3D model. Similarly, the process integrates traffic flow information (2006) and updates the 3D model as needed. FIG. 7B shows an exemplary process for identifying the object, while FIG. 7C-7H show in more details the object modeling process. The process checks sensors for object detection and scans the object against 3D library for matches. If a match is found, the process sets the object to the object in the library, and otherwise the process performs a best-guess of what the object is and send the object identification for subsequent 3D modeling use.

FIGS. 8A-8F show exemplary detection of objects outside of the vehicle and guidance on their handling. The detected objects can include automobile, a pedestrian, structure, or a bicycle, for example. The system assists the driver by identifying the objects as potential "threats" and recommend options for the driver. For example, the system can perform the following:

detecting an object external to a vehicle using one or more sensors;
determining a classification and a state of the detected object;
estimating the destination of the object;
predicting a likely behavior of the detected object based on prior behavior data and destination;
preparing the vehicle to respond based at least in part on the likely behavior of the detected object; and
notifying a driver of options based on the likely behavior.

Figure 8A:
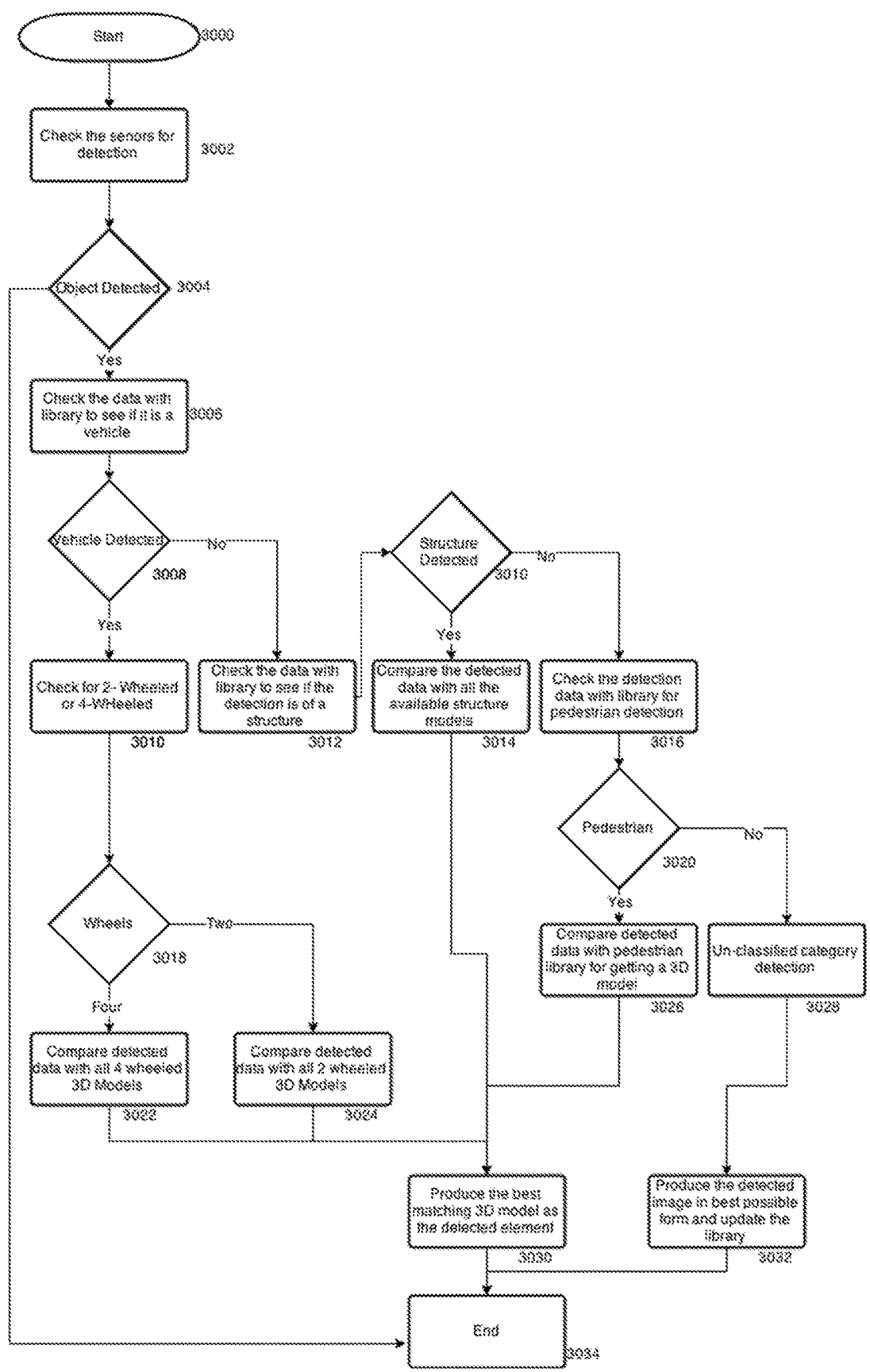
FIGS. 8A-8F show exemplary detection of objects outside of the vehicle and guidance on their handling.
Figure 8B:
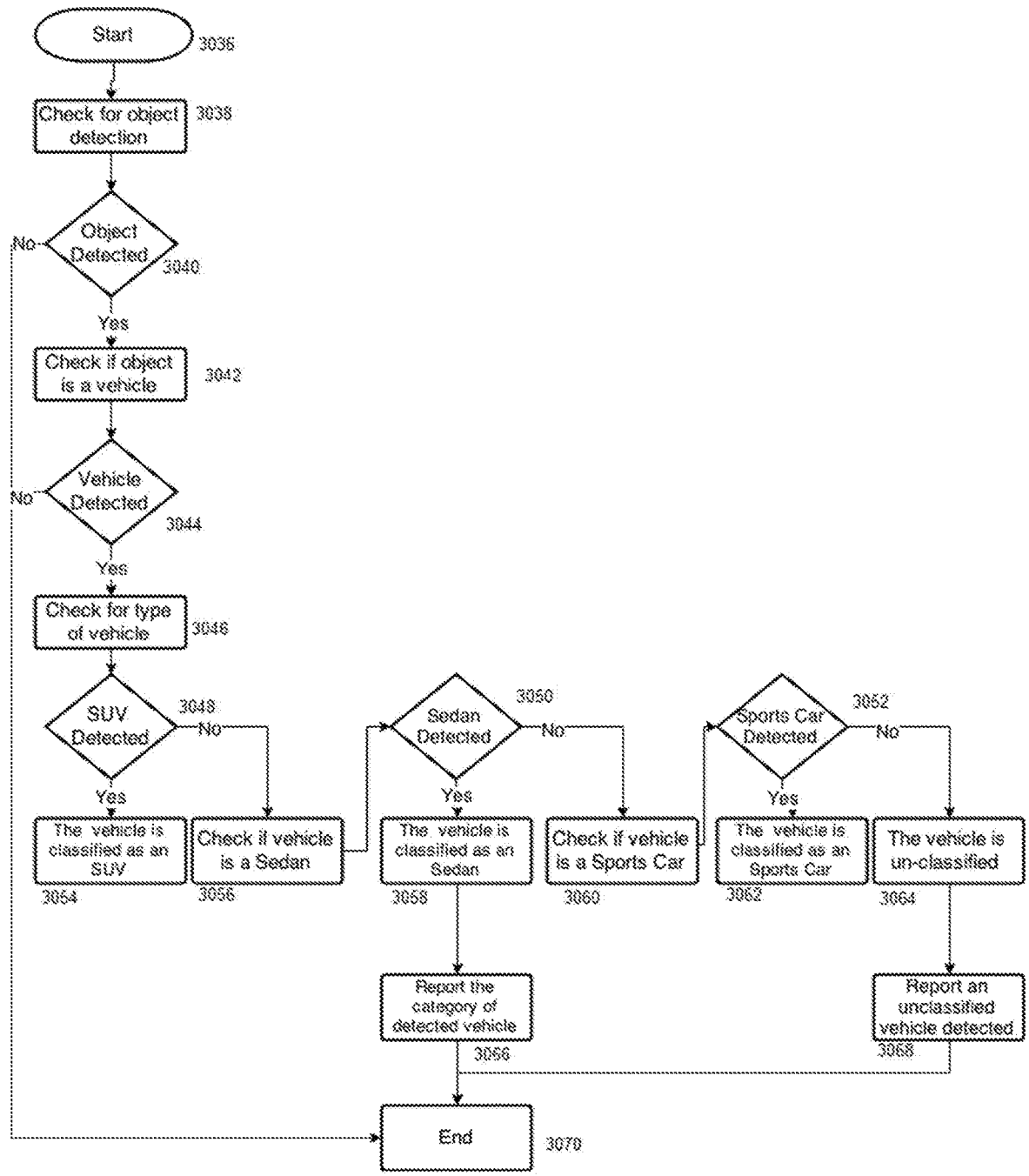
Figure 8C:
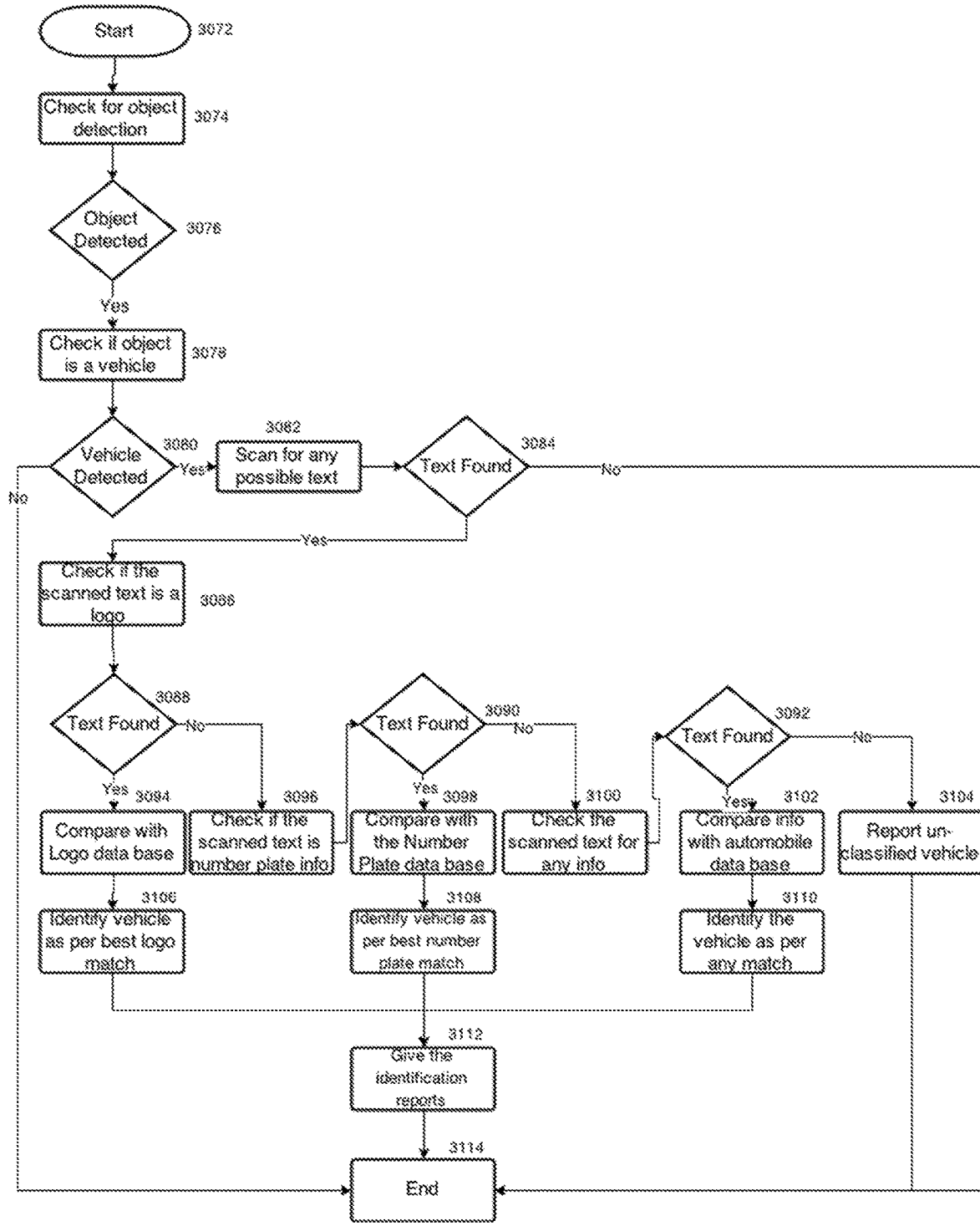
Figure 8D:
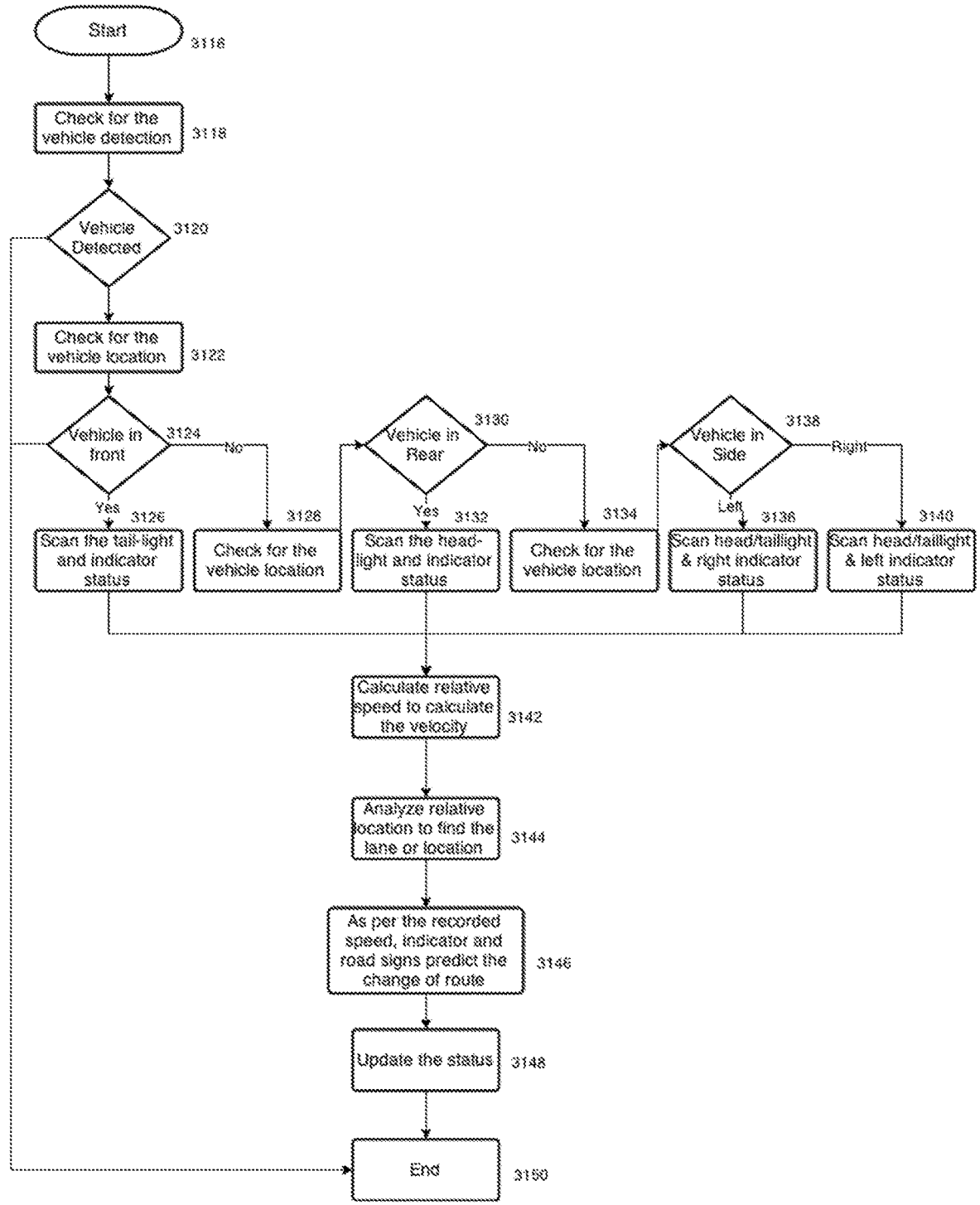
Figure 8E:
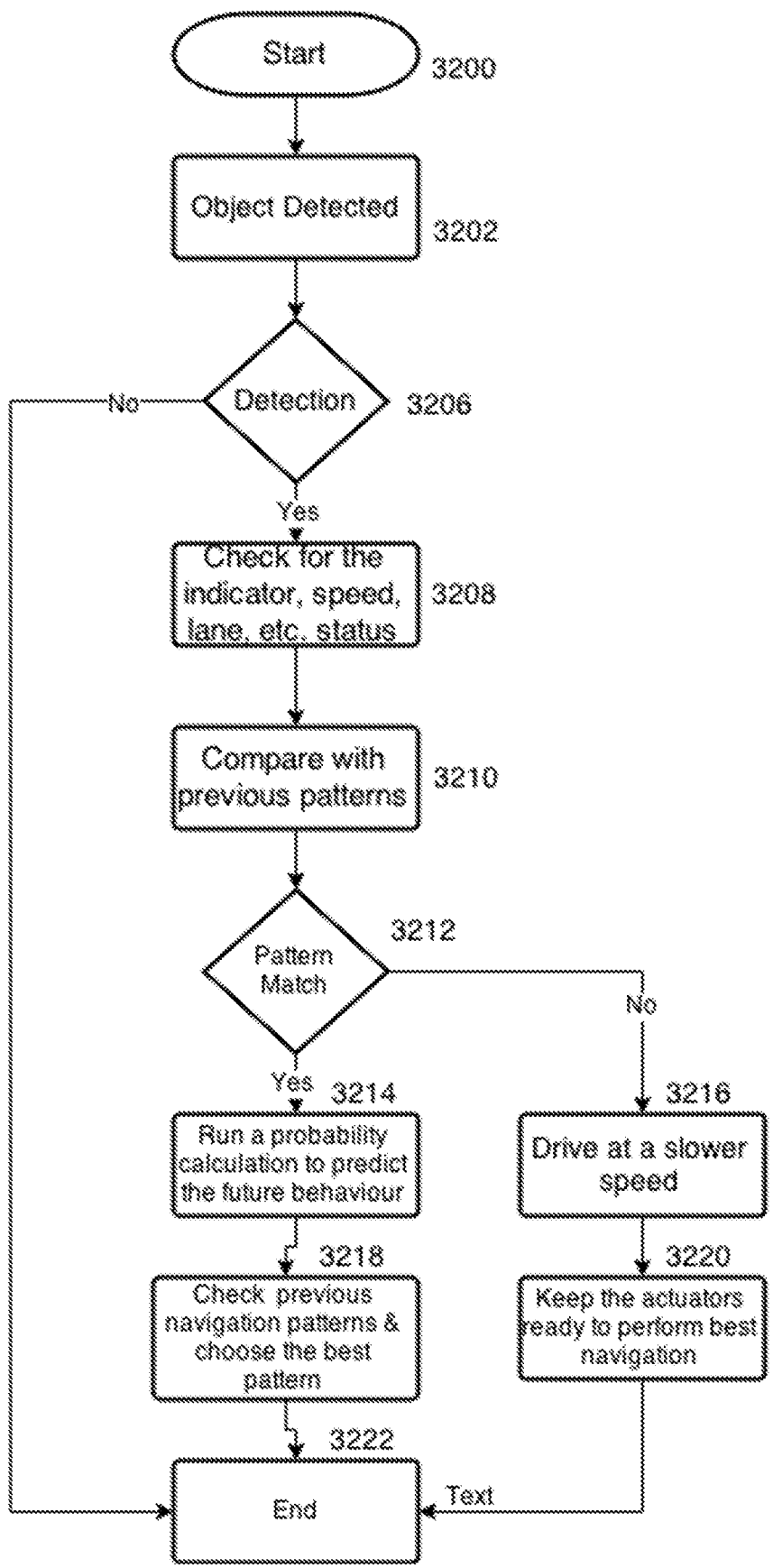
Figure 8F:
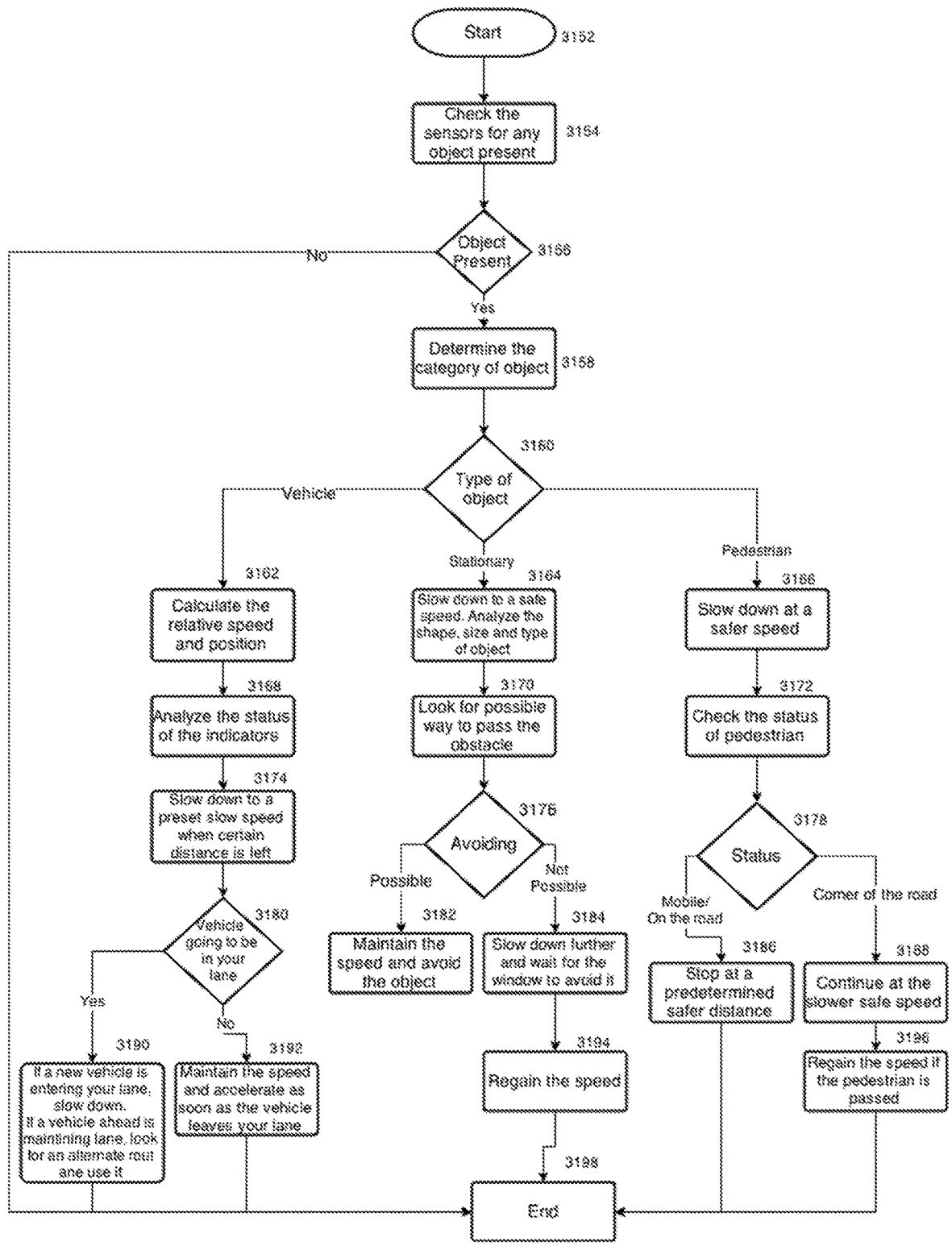

FIG. 8A shows an exemplary process to identify a vehicle based on the 3D models created in FIGS. 7A-7H. FIG. 8B shows an exemplary handling where the detected object is an automobile—the classification of the detected object includes the type of automobile. FIG. 8C shows a process to retrieve prior behavior data of the detected object by identifying at least one of a logo, a bumper sticker, or a license plate. Such information is then used to look up driver behavior. Public information such as driving ticket and Insurance information can be extracted to see if the driver has a bad driving history and if so the system can take a defensive driving posture. FIG. 8D shows an exemplary process to determine the state of the object. For example, the state of the detected object can be related to at least one of: location, traffic lane in which the detected object is traveling, speed, acceleration, entry onto a road, exit off of a road, activation of headlights, activation of taillights, or activation of blinkers. The behavior data is based on movement data for a plurality of other objects at one or more locations. The movement data are tracked using one of: satellite imagery, roadside cameras, on-board GPS data, or sensor data acquired for other nearby vehicles. FIG. 8E shows an exemplary process to identify predict other driver/rider behavior, while FIG. 8F generates proposed response to the object's expected behavior. The system can send a driver recommendation or vehicle command to orient the vehicle includes positioning the vehicle at a predetermined distance from the detected object, the predetermined distance being based, at least in part, on the classification of the detected object. The likely behavior of the detected object can be provided as a probability of the detected object entering to one or more states. The process includes receiving updated behavior data; and wherein predicting the likely behavior of the detected object is based at least in part on the updated behavior data. The driver can be informed of the options using haptic interface or a heads-up display. The process can also share the likely behavior of the object to neighboring vehicles using vehicle-to-vehicle communication.

The process may cause the vehicle to take particular actions in response to the predicted actions of the surrounding objects. For example, if other car is turning at the next intersection, the process may slow the vehicle down as it approaches the intersection. In this regard, the predicted behavior of other objects is based not only on the type of object and its current trajectory, but also based on some likelihood that the object may obey traffic rules or predetermined behaviors. In another example, the process may include a library of rules about what objects will do in various situations. For example, a car in a left-most lane that has a left-turn arrow mounted on the light will very likely turn left when the arrow turns green. The library may be built manually, or by the vehicle's observation of other vehicles (autonomous or not) on the roadway. The library may begin as a human built set of rules which may be improved by the vehicle's observations. Similarly, the library may begin as rules learned from vehicle observation and have humans examine the rules and improve them manually. This observation and learning may be accomplished by, for example, tools and techniques of machine learning. In addition to processing data provided by the various sensors, the computer may rely on environmental data that was obtained at a previous point in time and is expected to persist regardless of the vehicle's presence in the environment. For example, the system can use highly detailed maps identifying the shape and elevation of roadways, lane lines, intersections, crosswalks, speed limits, traffic signals, buildings, signs, real time traffic information, or other such objects and information. For example, the map information may include explicit speed limit information associated with various roadway segments. The speed limit data may be entered manually or scanned from previously taken images of a speed limit sign using, for example, optical-character recognition. The map information may include three-dimensional terrain maps incorporating one or more of objects listed above. For example, the vehicle may determine that another car is expected to turn based on real-time data (e.g., using its sensors to determine the current GPS position of another car) and other data (e.g., comparing the GPS position with previously-stored lane-specific map data to determine whether the other car is within a turn lane). These objects may have particular behavior patterns that depend on the nature of the object. For example, a bicycle is likely to react differently than a motorcycle in a number of ways. Specifically, a bicycle is more likely to make erratic movements when compared with a motorcycle, but is much slower and thus can be handled with ease compared to a speeding motorcycle. For each classification, the object data may also contain behavior information that indicates how an object having a particular classification is likely to behave in a given situation. Vehicle may then autonomously respond to the object based, in part, on the predicted behavior.

Figure 9A:
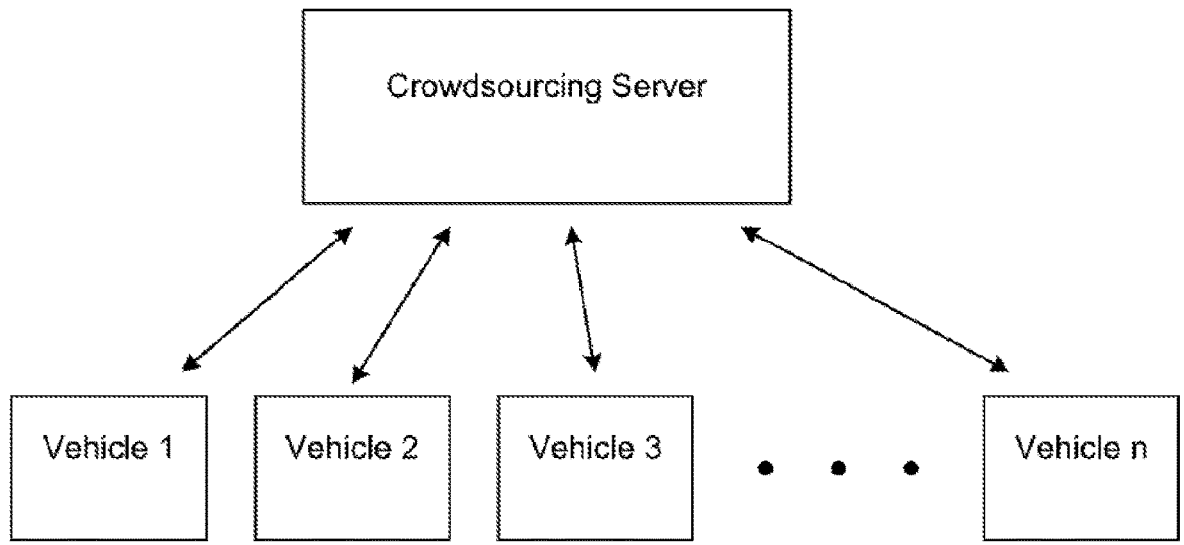
FIGS. 9A-9B show exemplary systems for capturing navigation data and using such data for smart vehicles.
Figure 9B:
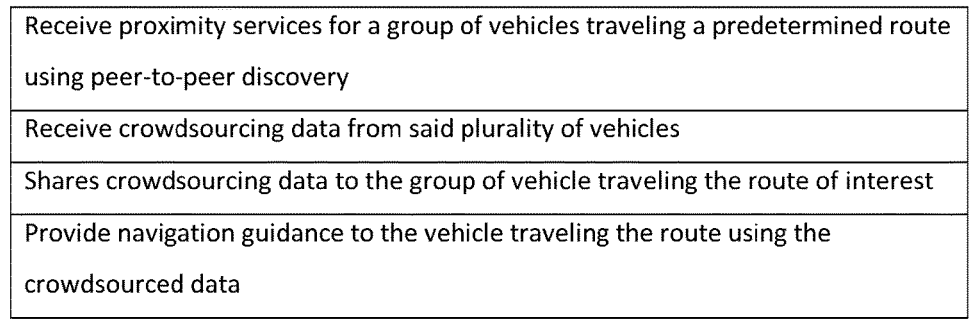
Figure 10:
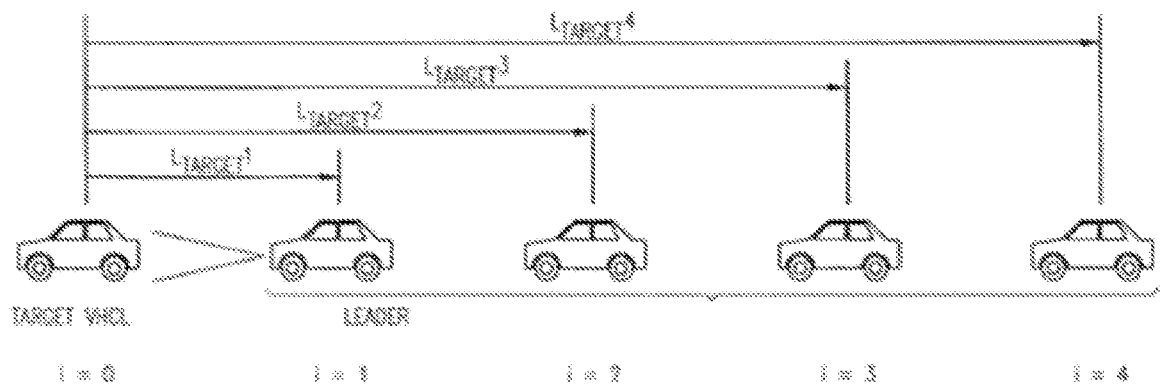
FIG. 10 shows an exemplary group of cars following flock control behavior.

FIG. 9A shows an exemplary system for crowd-sourcing navigation data. The system includes a crowdsourcing server in communication with a plurality of vehicles 1 . . . n. The vehicles in FIG. 9A performs peer-to-peer discovery and crowd-sourced navigation as shown in FIG. 9B. The system receives proximity services for a group of vehicles traveling a predetermined route using peer-to-peer discovery, receives crowdsourcing data from said plurality of vehicles, sharing crowdsourcing data to the group of vehicles (or a subsequent group of vehicles) traveling the route of interest. Such information can be used in providing navigation guidance to the vehicle traveling the route using the crowdsourced data.

Crowd-Sourced Map Updating and Obstacle Annotating

Next, a system to crowd-source the updates of precision maps with data from smart vehicles is detailed. In embodiments, crowd-sourced obstacle data can be used to update a map with precision. The obstacles can be rocks, boulders, pot-holes, manhole, utility hole, cable chamber, maintenance hole, inspection chamber, access chamber, sewer hole, confined space or can be water pool or rising tidal waves that affect the road as detected by a plurality of vehicles. Such crowd-sourced information is updated into the map and annotated by time, weather and periodicity. The detected obstacle information may include a geographic location of the vehicle and a predetermined map of the road. The computer system may determine the geographic location of the obstacle by, for example, using a laser rangefinder or light detection and ranging (LIDAR) unit to estimate a distance from the obstacle to the at least two objects near the vehicle and determining the geographic location of the obstacle using triangulation, for example. Such information is updated into the map system and marked as temporal. During use, if recent vehicles take defensive driving around the temporary obstacle, the map adds the obstacles to the map for the route guidance module to advise vehicles. If recent vehicles drive the road as though the obstacle does not exist, the system removes the obstacle from the map database, but keeps track of the history in case it is a periodic obstacle. The obstacle information is also reported to government agency for repair/maintenance.

In another embodiment, if vehicles drive through the lane with a smooth line or curve, but abruptly brakes, the system infers that the road has defects or potholes, for example, and the bad infrastructure is reported for path planning (to add more travel time, or to change the route to avoid the bad road infrastructure if it is long.

The new information is used to update a digital map that lacks the current information or that contains inaccuracies or may be incomplete. The digital map stored in the map database may be updated using the information processed by a map matching module, matched segment module, and unmatched segment module. The map matching module, once it has received obstacle location and GPS traces, processes obstacle locations and GPS traces by matching them to a road defined in the digital map. The map matching module matches the obstacles and the GPS traces with the most likely road positions corresponding to a viable route through the digital map by using the processor to execute a matching algorithm. In one example, the matching algorithm may be a Viterbi matching algorithm. Where the GPS traces do match a road defined in the digital map, the matched trace to which the GPS traces match and obstacle information are sent to the matched segment module for further processing as will be described below. Where the GPS traces do not match a road defined in the digital map, the unmatched trace to which the GPS traces are correlated with and the obstacle position information are sent to the unmatched segment module for further processing. The matched segment module and unmatched segment module both provide metadata to the map updating module. The metadata may include obstacle metadata road geometry refinement metadata, road closure and reopening metadata, missing intersection metadata, missing road data and one-way correction metadata. The map updating module updates the digital map in the map database.

The process to update maps using crowd-sourced data may begin with the unmatched segment module clustering the unmatched GPS traces received from the map matching module. Many available algorithms may be suitable for this process, but in one example, an agglomerative clustering algorithm that iteratively compares GPS traces with each other and combines those that fall within a pre-determined tolerance into a cluster may be used. One example of such and algorithm uses the Hausdorff distance as its distance measure in the clustering algorithm. Once the cluster is selected, the unmatched segment module may produce a single road geometry for a cluster of unmatched GPS traces using a centerline fitting procedure in which the single road geometry describes a new road segment with the obstacle which is not described in the current map database. In one example, a polygonal principal curve algorithm or a Trace Clustering Algorithm (TCl) algorithm can be used. The digital map can be modified to include the new road, including possibly new intersections in the base map and any associated pointers or indices updated.

Lane Marking Visibility Handling

In some embodiments, a lead vehicle identifies lane information that may include lane markings on the road, and the computer system may use one or more sensors to sense the lane markings. At some point, the lead vehicle may determine that the lane information has become unavailable or unreliable. For example, severe fog may be present and severely affect the lane markings. In other examples, the vehicle may no longer be able to detect the lane markings on the road, the vehicle may detect contradictory lane markings on the road, the vehicle may no longer be able to determine a geographic location of the vehicle, and/or the vehicle may not be able to access a predetermined map of the road. Other examples are possible as well.

In response to determining that the lane information has become unavailable or unreliable, the computer system may use at least one sensor to monitor at least one neighboring vehicle, such as a neighboring vehicle in a neighboring lane or a neighboring vehicle behind the vehicle that is part of the flock. The computer system may then control the vehicle to maintain a distance between the vehicle and the at least one neighboring vehicle to be at least a predetermined minimum distance and even if the vehicle is unable to rely on the lane information to estimate a location of the lane on the road, the vehicle may avoid colliding with the at least one neighboring vehicle.

In other embodiments, the lane information may include a geographic location of the vehicle and a predetermined map of the road. The computer system may determine the geographic location of the vehicle by, for example, querying a location server for the geographic location of the vehicle. Alternatively, if the predetermined map indicates a geographic location of at least two objects near the vehicle, the computer system may determine the geographic location of the vehicle by, for example, using a laser rangefinder or light detection and ranging (LIDAR) unit to estimate a distance from the vehicle to the at least two objects near the vehicle and determining the geographic location of the vehicle using triangulation. Other examples are possible as well. In any case, the computer system may then locate the geographic location of the vehicle on the predetermined map to determine a location of the lane relative to the geographic location of the vehicle.

In still other embodiments, the lane information may be derived from a leading vehicle that is in front of the vehicle in the lane and correlation with other information such as map data and independent lane analysis to prevent the blind-following-the blind situation. The computer system may estimate a path of the leading vehicle using, for example, a laser rangefinder and/or a LIDAR unit. Other examples are possible as well. Once the computer system has estimated the path of the leading vehicle, the computer system may estimate the location of the lane based on the estimated path. For example, the computer system may estimate the location of the lane to include the estimated path (e.g., extend by half of a predetermined lane width on either side of the estimated path). Other examples are possible as well.

In some embodiments, the computer system may maintain a predetermined threshold for the lane information, and the computer system may determine that the lane information has become unavailable or unreliable when the computer system detects that a confidence of the lane information (e.g., how confident the computer system is that the lane information is reliable) is below the predetermined threshold. In some embodiments, the computer system may additionally maintain a predetermined time period for the lane information, and the computer system may determine that the lane information has become unavailable or unreliable when the computer system detects that a confidence of the lane information is below the predetermined threshold for at least the predetermined amount of time.

Upon determining that the lane information has become unavailable or unreliable, the computer system may use at least one sensor to monitor at least one neighboring vehicle. The at least one neighboring vehicle may include, for example, a neighboring vehicle in a lane adjacent to the lane in which the vehicle is traveling. As another example, the at least one neighboring vehicle may include a neighboring vehicle behind the vehicle in the lane in which the vehicle is traveling. As still another example, the at least one neighboring vehicle may include a first neighboring vehicle and a second neighboring vehicle, each of which may be either in a lane adjacent to the lane in which the vehicle is traveling or behind the vehicle in the lane in which the vehicle is traveling. Other examples are possible as well.

When the lane information has become unavailable or unreliable, the computer system may control the vehicle to maintain a distance between the vehicle and the at least one neighboring vehicle to be at least a predetermined distance. The predetermined distance may be, for example, a distance determined to be a safe distance and/or a distance approximately equal to the difference between a predetermined lane width and a width of the vehicle. Other predetermined distances are possible as well.

In order to maintain the distance between the vehicle and the at least one neighboring vehicle to be at least the predetermined distance, the computer system may continuously or periodically use the at least one sensor on the vehicle to monitor the distance between the vehicle and the at least one neighboring vehicle. The computer system may monitor the distance between the vehicle and the at least one neighboring vehicle using, for example, a laser rangefinder and/or LIDAR unit. If the distance between the vehicle and the at least one neighboring vehicle becomes less than the predetermined distance, the computer system may move the vehicle away from the at least one neighboring vehicle in order to maintain the distance between the vehicle and the at least one neighboring vehicle to be at least the predetermined distance.

In some embodiments, in addition to maintaining the distance between the vehicle and the at least one neighboring vehicle to be at least the predetermined distance, the computer system may additionally maintain the distance between the vehicle and the at least one neighboring vehicle to be within a predetermined range of the predetermined distance. In these embodiments, if the distance between the vehicle and the at least one neighboring vehicle becomes too large (e.g., no longer within the predetermined range of the predetermined distance), the computer system may move the vehicle closer to the at least one neighboring vehicle. This may, for example, prevent the vehicle from drifting so far away from the neighboring vehicle that the vehicle drifts into a lane on the opposite side of the vehicle from the neighboring vehicle.

As noted above, in some embodiments the at least one vehicle may include a first neighboring vehicle and a second neighboring vehicle. In these embodiments, maintaining the distance between the vehicle and the at least one neighboring vehicle may involve maximizing both a first distance between the vehicle and the first neighboring vehicle and a second distance between the vehicle and the second neighboring vehicle (e.g., such that the vehicle remains approximately in the middle between the first neighboring vehicle and the second neighboring vehicle). Each of the first distance and the second distance may be at least the predetermined distance.

In some embodiments, in addition to maintaining the distance between the vehicle and the at least one neighboring vehicle to be at least the predetermined distance, the computer system may determine an updated estimated location of the lane. To this end, the computer system may use the at least one sensor to monitor at least a first distance to the at least one neighboring vehicle and a second distance to the at least one vehicle. Based on the first distance and the second distance, the computer system may determine a first relative position and a second relative position (e.g., relative to the vehicle) of the at least one neighboring vehicle. Based on the first relative position and the second relative position, the computer system may estimate a path for the at least one neighboring vehicle. The computer system may then use the estimated path to determine an updated estimated location of the lane. For example, in embodiments where the at least one neighboring vehicle is traveling in a lane adjacent to the lane in which the vehicle is traveling, the computer system may determine the estimated location of the lane to be substantially parallel to the estimated path (e.g., the lane may be centered on a path that is shifted from the estimated path by, e.g., a predetermined lane width and may extend by half of the predetermined lane width on either side of the path). As another example, in embodiments where the at least one neighboring vehicle is traveling behind the vehicle in the lane in which the vehicle is traveling, the computer system may determine the estimated location of the lane to be an extrapolation (e.g., with constant curvature) of the estimated path. Other examples are possible as well.

In some embodiments, the computer system may additionally use a speed sensor to monitor a speed of the at least one neighboring vehicle and may modify a speed of the vehicle to be less than the speed of the at least one neighboring vehicle. This may allow the vehicle to be passed by the at least one neighboring vehicle. Once the at least one neighboring vehicle has passed the vehicle, the at least one neighboring vehicle may become a leading vehicle, either in a lane adjacent to the lane in which the vehicle is traveling or a leading vehicle that is in front of the vehicle in the lane in which the vehicle is traveling, and the computer system may estimate the location of the lane of the road based on an estimated path of the leading vehicle, as described above.

In some embodiments, the computer system may begin to monitor the at least one neighboring vehicle only in response to determining that the lane information has become unavailable or unreliable. In these embodiments, prior to determining that the lane information has become unavailable or unreliable, the computer system may rely solely on the lane information to estimate the location of the lane. In other embodiments, however, the computer system may also monitor the at least one neighboring vehicle prior to determining that the lane information has become unavailable or unreliable. In these embodiments, the computer system may additionally use the distance to the at least one neighboring vehicle to estimate the location of the lane in which the vehicle is traveling. For example, if the at least one neighboring vehicle is traveling in a lane adjacent to the lane in which the vehicle is traveling, the computer system may determine that the lane does not extend to the at least one neighboring vehicle. As another example, if the at least one neighboring vehicle is traveling behind the vehicle in the lane in which the vehicle is traveling, the computer system may determine that the lane includes the at least one neighboring vehicle. Other examples are possible as well. Alternatively, in these embodiments, prior to determining that the lane information has become unavailable or unreliable, the computer system may simply use the distance to the at least one neighboring vehicle to avoid collisions with the at least one neighboring vehicle.

Further, in some embodiments, once the vehicle begins to monitor the at least one neighboring vehicle, the computer system may stop using the lane information to estimate the location of the lane in which the vehicle is traveling. In these embodiments, the computer system may rely solely on the distance to the at least one neighboring vehicle to avoid collisions with the at least one neighboring vehicle until the lane information becomes available or reliable. For example, the computer system may periodically attempt to obtain updated lane information. Once the computer system determines that the lane information has become available or reliable, the lane information has become available or reliable, the computer system may once again rely on the updated estimated location of the lane and less (or not at all) on the distance to the at least one neighboring vehicle. The computer system may determine that the updated lane information is reliable when, for example, the computer system determines that a confidence of the updated lane information is greater than a predetermined threshold. The predetermined threshold may be the same as or different than the predetermined threshold.

Figure 11:
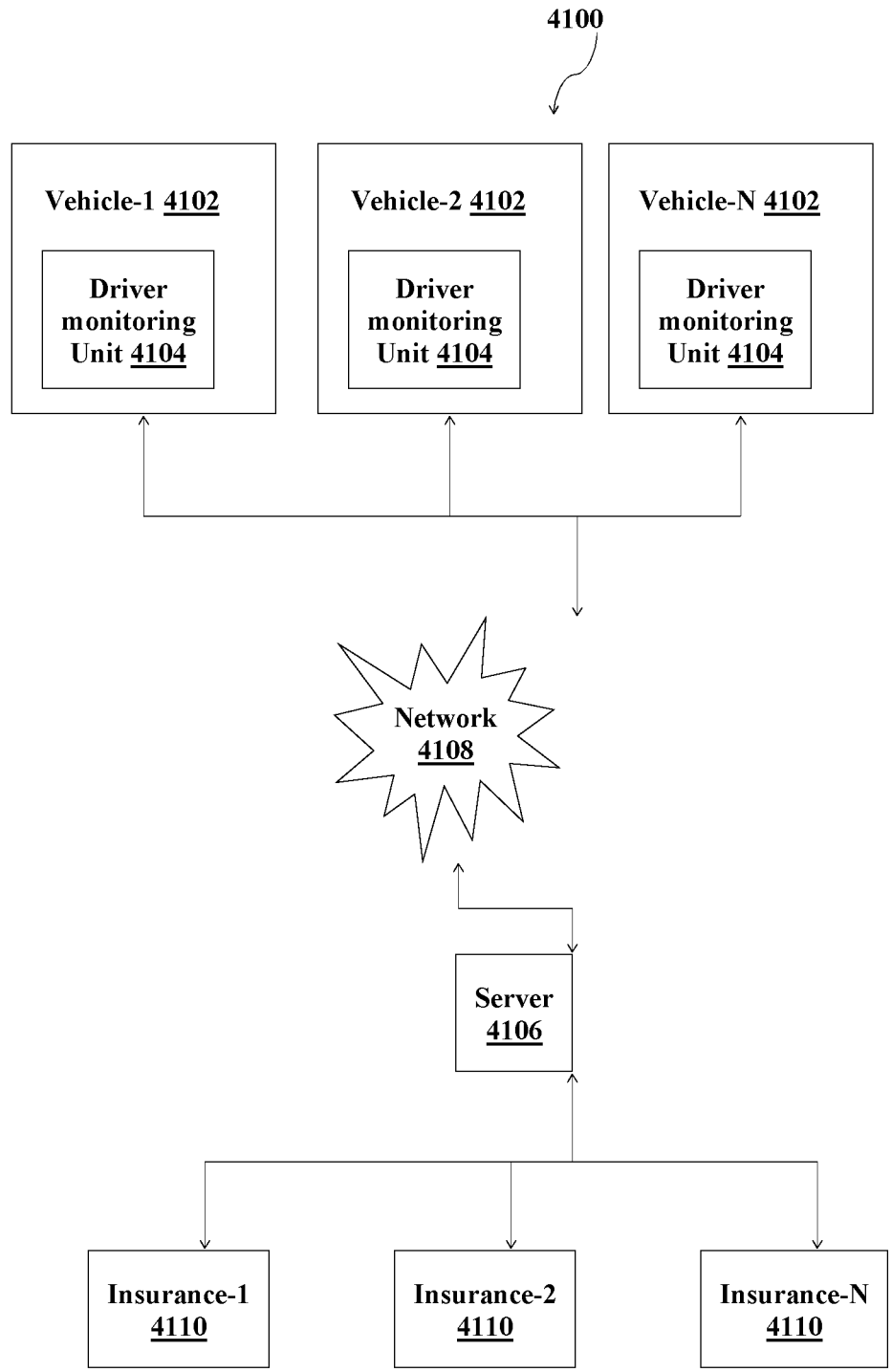
FIG. 11 illustrate a typical network environment in which the systems, methods for cloud based driver behavior capturing and monitoring.

FIG. 11 illustrate a typical network environment 4100 in which the systems, methods, and computer program products may be implemented, according to embodiments as disclosed herein. In an embodiment, the environment 4100 includes a plurality of drivers who are seeking insurance drive vehicles 4102. The vehicle 4102 described herein can be configured to include a driver monitoring unit 4104 installed thereon. The monitoring device may be self contained, such as a single unit mounted on a windshield or dashboard of the vehicle 4102. Alternatively, the monitoring device 4104 may include multiple components, such as a processor or central unit mounted under a car seat or in a trunk of the vehicle and a user interface mounted on a dashboard or windshield. Similarly, the monitoring unit 4104 may have a self-contained antenna in the unit or may be connected to remotely mounted antennas for communication with remote systems.

Further, the driver monitoring units 4104 may be connected to an on-board diagnostic system or data bus in the vehicle 4104. Information and behavior data associated with the driver may be collected from the on-board diagnostic system. The driver monitoring system may receive inputs from internal and external sources and sensors such as accelerometers, global positioning systems (GPS), vehicle on-board diagnostic systems, seatbelt sensors, wireless device, or cell phone use detectors, alcohol vapor detectors, or trans-dermal ethanol detection. Further, the details related to the driver monitoring unit 4104 are described in conjunction with the FIG. 12.

Further, the information may be exchanged between driver monitoring unit 104 and central monitoring system or server 4106 in real-time or at intervals. For example, the driver behavior parameters may be transmitted to server 4106 via a communication network 4108. In an embodiment, the communication network 4108 described herein can include for example, but not limited to, a cellular, satellite, Wi-Fi, Bluetooth, infrared, ultrasound, short wave, microwave, global system for mobile communication, or any other suitable network. The information sent to the server 4104 may then be forwarded with one or more insurance providers 4110. The server 4106 can be configured to process the driver behavior parameters and/or store the data to a local or remote database. The drivers or insurance provider can access the data on the server 4106. In some embodiments, the data captured by monitoring unit 4104 in the vehicle 4102 may be transmitted via a hardwired communication connection, such as an Ethernet connection that is attached to vehicle 4102 when the vehicle is within a service yard or at a base station or near the server 4106. Alternatively, the data may be transferred via a flash memory, diskette, or other memory device that can be directly connected to the server 4106.

In one embodiment of the invention, the data captured by driver monitoring unit 4104 can be used to monitor, provide feedback, mentor, provide recommendations, adjust insurance rates, and to analyze a driver's behavior during certain events. For example, if vehicle 4102 is operated improperly, such as speeding, taking turns too fast, colliding with another vehicle, or driving in an unapproved area, then the driver monitoring unit 4104 or server 4106 may adjust the insurance rates for the driver and provide feedback and suggestions to the driver, such as to improve the diving skills. Additionally, if the driver's behavior is inappropriate or illegal, such as not wearing a seatbelt or using a cell phone while driving then feedback and suggestions can be provided to the driver to improve the diving skills.

In an embodiment, the insurance price may be adjusted based on the driver behavior. For example, if an insurance company, supervisor, or other authority determines that the driver is uninsured, underinsured, lacking coverage required in a particular jurisdiction, that the driver's insurance premiums are delinquent, and/or if the vehicle is not properly registered and/or delinquent in registration with the state, then the driver monitoring unit 102 may be directed to disable or deactivate the vehicle. Alternatively, the driver monitoring unit 102 can provide feedback and recommendations to the driver if it is determined that the driver behavior is uninsured, underinsured, lacking coverage required in a particular jurisdiction, or that the driver's insurance premiums are delinquent. In an embodiment, the driver's behavior is typically evaluated while driving the vehicle 102 with the driver monitoring unit 104 installed thereon. After receiving the driver behavior data from the driver monitoring unit 104, the insurance rates can be adjusted accordingly.

Figure 12:
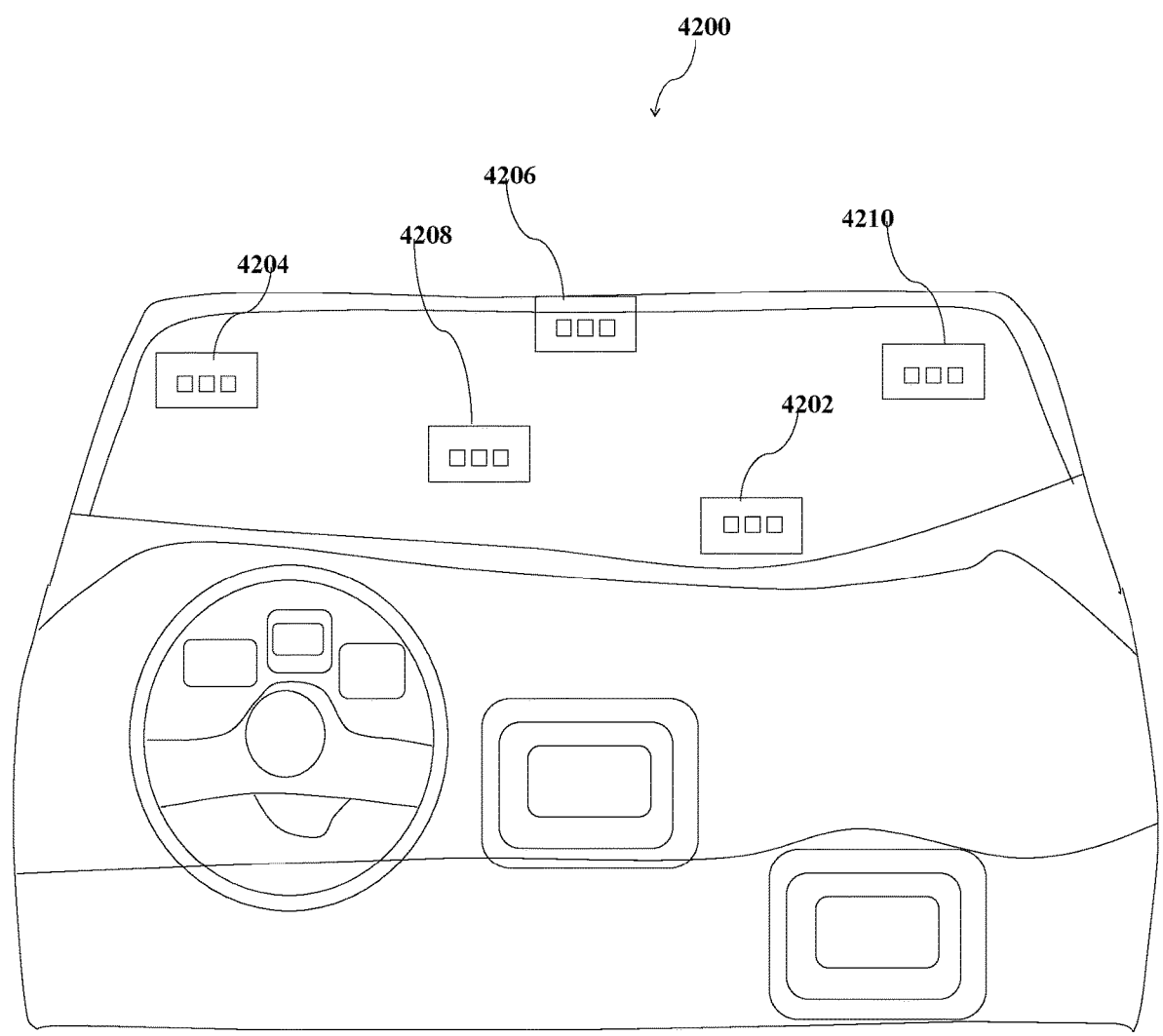
FIG. 12 is a diagram illustrating generally, a portion of vehicle alone with possible locations of sensors, cameras, among others.

FIG. 12 is a diagram illustrating generally, a portion of vehicle 4200 alone with possible locations of sensors, cameras, and/or other technologies, according to embodiments described herein. In an embodiment, exemplary mounted locations for the driver monitoring unit 4104 are illustrated, such as on a dashboard 4202, windshield 4204, headliner 4206, surface 4208, corner 4210. It will be understood that all or parts of the driver monitoring unit 4104 can be mounted in any other location that allows for audio and/or visual feedback to the driver of the vehicle 4102 while the vehicle is in operation. The driver monitoring unit 4104 is illustrated as being coupled to on-board diagnosis, from which it may receive inputs associated with the driver and vehicle operating parameters. The driver monitoring units such as 4202, 4204, 4206, 4208, and 4210 can be coupled to on-board diagnosis (not shown). Moreover, the driver monitoring system may be coupled to other sensors, such as a sensor for detecting the operation and use of a cellular or wireless device in the vehicle 4102.

In an embodiment, the driver monitoring units can be configured to include for example, but not limited to, accelerometer, cameras, gyroscope, magnetometer, and the like sensors. In an embodiment, the accelerometer can include at least one accelerometer for measuring a lateral (sideways), longitudinal (forward and aft) and vertical acceleration in order to determine whether the driver is operating the vehicle in an unsafe or aggressive manner. For example, excessive lateral acceleration may be an indication that the driver is operating the vehicle at an excessive speed around a turn along a roadway. Furthermore, it is possible that the driver may be traveling at a speed well within the posted speed limit for that area of roadway. However, excessive lateral acceleration, defined herein as "hard turns," may be indicative of aggressive driving behavior by the driver and may contribute to excessive wear on tires and steering components as well as potentially causing the load such as a trailer to shift and potentially overturn.

As such, it can be seen that monitoring such driver behavior by providing feedback and recommendations to the driver during the occurrence of aggressive driving behavior such as hard turns can improve safety and reduce accidents. In addition, providing recommendations for such aggressive driver behavior can reduce wear and tear on the vehicle and ultimately reduce fleet maintenance costs as well as reduce insurance costs and identify at risk drivers and driving behavior to fleet managers.

In one aspect, the driver monitoring system may be in data communication with an on board diagnostic (OBD) system of the vehicle such as via a port. In some vehicle models, the driver monitoring system is in data communication with a controller area network (CAN) system (bus) to allow acquisition of certain driver and vehicle operating parameters including, but not limited to, vehicle speed such as via the speedometer, engine speed or throttle position such as via the tachometer, mileage such as via the odometer reading, seat belt status, condition of various vehicle systems including anti-lock-braking (ABS), turn signal, headlight, cruise control activation and a multitude of various other diagnostic parameters such as engine temperature, brake wear, and the like. The OBD or CAN allows for acquisition of the above-mentioned vehicle parameters for processing thereby and/or for subsequent transmission to the server 4106.

In an embodiment, the driver monitoring system may also include a GPS receiver (or other similar technology designed to track location) configured to track the location and directional movement of the driver in either real-time or over-time modes. As is well known in the art, GPS signals may be used to calculate the latitude and longitude of a driver as well as allowing for tracking of driver movement by inferring speed and direction from positional changes. Signals from GPS satellites also allow for calculating the elevation and, hence, vertical movement, of the driver.

In an embodiment, the driver monitoring unit may further include a mobile data terminal (MDT) mounted for observation and manipulation by the driver, such as near the vehicle dash. The MDT can be configured to include an operator interface such as a keypad, keyboard, touch screen, display screen, or any suitable user input device and may further include audio input capability such as a microphone to allow voice communications. The driver monitoring unit receives inputs from a number of internal and external sources. The OBD/CAN bus, which provides data from the vehicle's on-board diagnostic system, including engine performance data and system status information. A GPS receiver provides location information. The CDR, XLM, or accelerometers provide information regarding the vehicle's movement and driving conditions. Any number of other sensors, such as but not limited to, a seat belt sensor, proximity sensor, driver monitoring sensors, or cellular phone use sensors, also provide inputs to the driver monitoring system.

In an embodiment, the driver monitoring system may have any type of user interface, such as a screen capable of displaying messages to the vehicle's driver or passengers, and a keyboard, buttons or switches that allow for user input. The system or the user interface may have one or more status LEDs or other indicators to provide information regarding the status of the device's operation, power, communications, GPS lock, and the like. Additionally, the LEDs or other indicators may provide feedback to the driver when a driving violation occurs. Additionally, monitoring system may have a speaker and microphone integral to the device.

In an embodiment, the monitoring system may be self-powered, such as by a battery, or powered by the vehicle's battery and/or power generating circuitry. Access to the vehicle's battery power may be by accessing the power available on the vehicle's OBD and/or CAN bus. The driver monitoring system may be self-orienting, which allows it to be mounted in any position, angle or orientation in the vehicle or on the dashboard. In an embodiment, the driver monitoring system determines a direction of gravity and a direction of driver movement and determines its orientation within the vehicle using this information. In order to provide more accurate measurements of driver behavior, the present invention filters gravitational effects out of the longitudinal, lateral and vertical acceleration measurements when the vehicle is on an incline or changes its horizontal surface orientation. Driver behavior can be monitored using the accelerometer, which preferably will be a tri-axial accelerometer. Acceleration is measured in at least one of lateral, longitudinal and/or vertical directions over a predetermined time period, which may be a period of seconds or minutes. An acceleration input signal is generated when a measured acceleration exceeds a predetermined threshold.

It will be understood that the present invention may be used for both fleets of vehicles and for individual drivers. For example, the driver monitoring system described herein may be used by insurance providers to monitor, recommend, provide feedback, and adjust insurance rates based on the driving. A private vehicle owner may also use the present invention to monitor the driver behavior and user of the vehicle. For example, a parent may use the system described herein to monitor a new driver or a teenage driver behavior.

An embodiment of the invention provides real-time recommendations, training, or other feedback to a driver while operating the vehicle. The recommendations are based upon observed operation of the vehicle and are intended to change and improve driver behavior by identifying improper or illegal operation of the vehicle. The driver monitoring system may identify aggressive driving violations. For example, based upon the inputs from an acceleration or CDR, aggressive driving behavior can be detected, such as exceeding acceleration thresholds in a lateral, longitudinal, or vertical direction, hard turns, hard acceleration or jackrabbit starts, hard braking, and/or hard vertical movement of the vehicle.

Further, in an embodiment, the sensor and camera described herein can be configured to communicate with the vehicle entertainment system. Typically, this functionality includes pre-installed software or a user-downloadable application from a network source (such as Apple's iTunes or Google's Android Market). The system functionality may include mapping functions, directions, landmark location, voice-control, and many other desirable features. When such mobile computing device is placed within the vehicle then a convenient vehicle entertainment system associated with the vehicle can be provided. In an embodiment, a remote switch can be used to initiate the vehicle entertainment software application by communicating with the cameras/sensors located in the vehicle and/or software residing on the mobile computing device. Remote switch described herein can include one of a number of well-known remote switches that uses wireless or wired technology to communicate with mobile computing device. For example, remote switch may include for example, but not limited to, a Bluetooth, RF, infrared, or other well-known wireless communication technology, or it may be connected via one or more wires to mobile computing device. The switch may be located on any vehicle interior surface, such as on a steering wheel, visor, dashboard, or any other convenient location.

Figure 13:
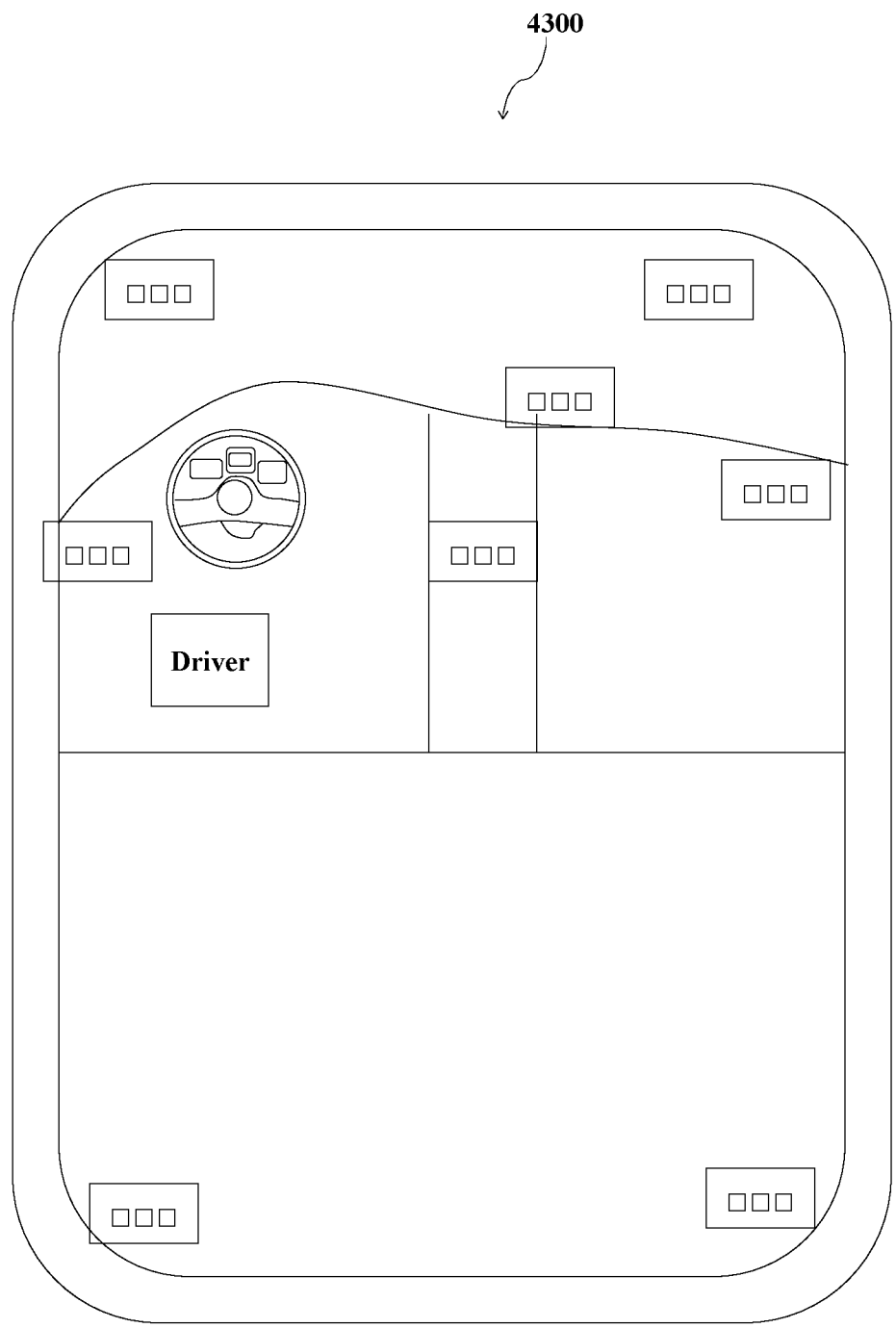
FIG. 13 is a diagram illustrating generally, possible locations of sensors, cameras, and/or other technologies.
Figure 14:
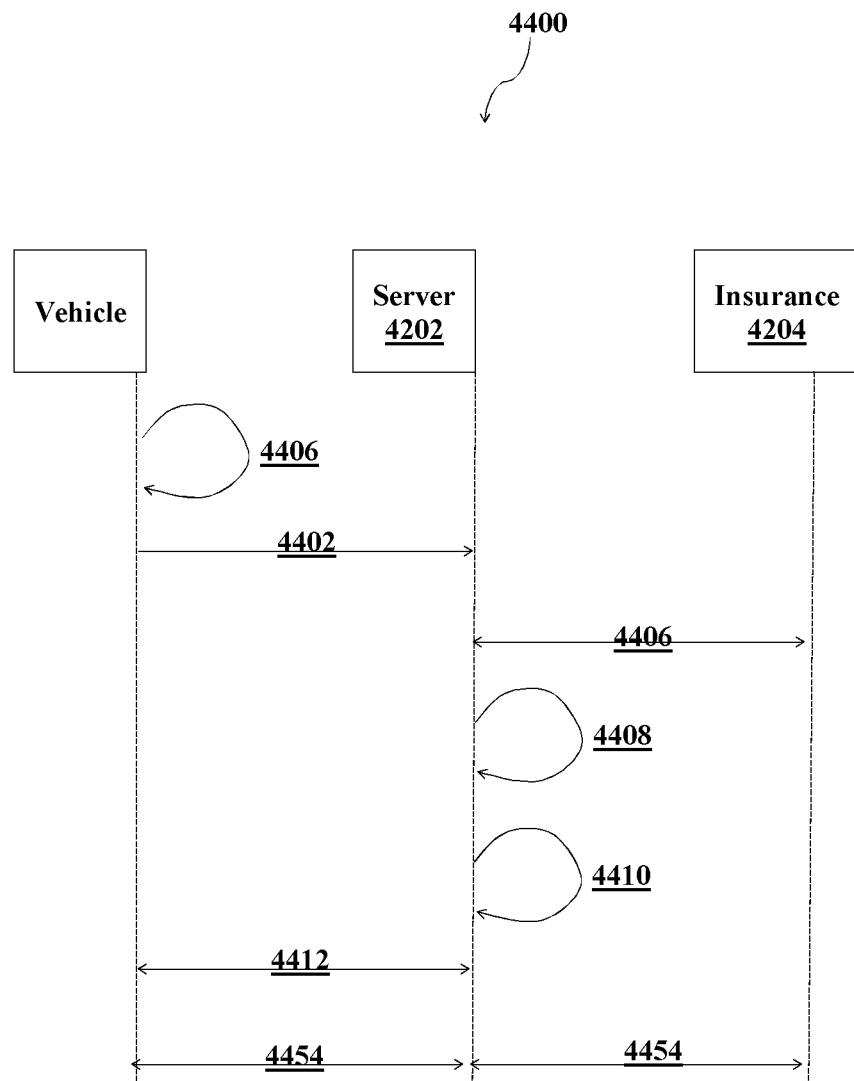
FIG. 14 is a sequence diagram illustrates generally, operations performed by the system as described in the FIG. 11.

FIG. 13 is a diagram 4300 illustrating generally, possible locations of sensors, cameras, and/or other technologies, according to embodiments described herein. FIG. 14 is a sequence diagram illustrates generally, operations 300 performed by the system as described in FIG. 11, according to embodiments described herein. In an embodiment, at 4402, the driver monitoring unit 104 can be configured to monitor the behavior of the driver. The system can be configured to include the driver monitoring unit 4104 installed in the vehicle 102 to monitor the behavior parameters of the driver while the vehicle 4102 is being driven. The vehicle 4102 can include cameras, gyroscope, magnetometer, accelerometer, and other sensors installed thereon to monitor the behavior parameter of the driver. In an embodiment, the cameras or sensors may be placed at any place in the vehicle, such as for example at four corners of the front windshield, in a way that it can directly capture the behavior parameters of the driver. For example, based on the driver gestures, the cameras can detect finger position to detect that driver is pointing at a particular object or vehicle and searches the internet for the vehicle. Further, in an embodiment, a flexible display film adhesively secured on the front windshield. The display can be used controlled by a computer to display info in a discrete way that may not take driver's eyes off the road and opposing vehicles. In an embodiment, at 4404, the driver monitoring unit 4102 can be configured to transmit the behavior parameters of the driver to the server 4106. In an embodiment, the driver behavior parameters described herein can include for example, but not limited to, vehicle speed, vehicle accelerations, driver location, seatbelt use, wireless device use, turn signal use, driver aggression, detection of CO2 vapor, detection of alcohol, driver seating position, time, and the like. In an embodiment, at 4406, the server 4106 can be configured to transmit the driver behavior parameters to one or more insurance providers. In an embodiment, at 4408, the server 4106 can be configured to analyze the driver behavior parameters and adjust the insurance rates for the driver. For example, if the driver is driving roughly by drinking alcohol then the insurance rate may get decreased. In an embodiment, at 4410, the server 4106 can be configured to match the driver behavior preferences with similar or substantially similar preferences of other drivers. The server 4104 can be configured to generate action recommendations best matching the behavior of the driver. In an embodiment at 4412, the server 4106 can be configured to provide the generated recommendations to the driver. Based on the driver behavior parameters the sever 4106 provides feedback and recommendations to the driver, such as to improve the driving skills. Further, in an embodiment, a flexible display film adhesively secured on the front windshield. The display can be used controlled by a computer to display info in a discrete way that may not take driver's eyes off the road and opposing vehicles. In an embodiment, at 4414, the server 4106 can be configured to frequently monitor the behavior parameters associated with the driver. Any changes in the behavior parameters can affect the overall system performance and the driver experience. The server 4106 can be configured to frequently monitor and dynamically update the insurance rate and action recommendations, which in turn helps the driver for effectively improving the driving skills.

Figure 15:
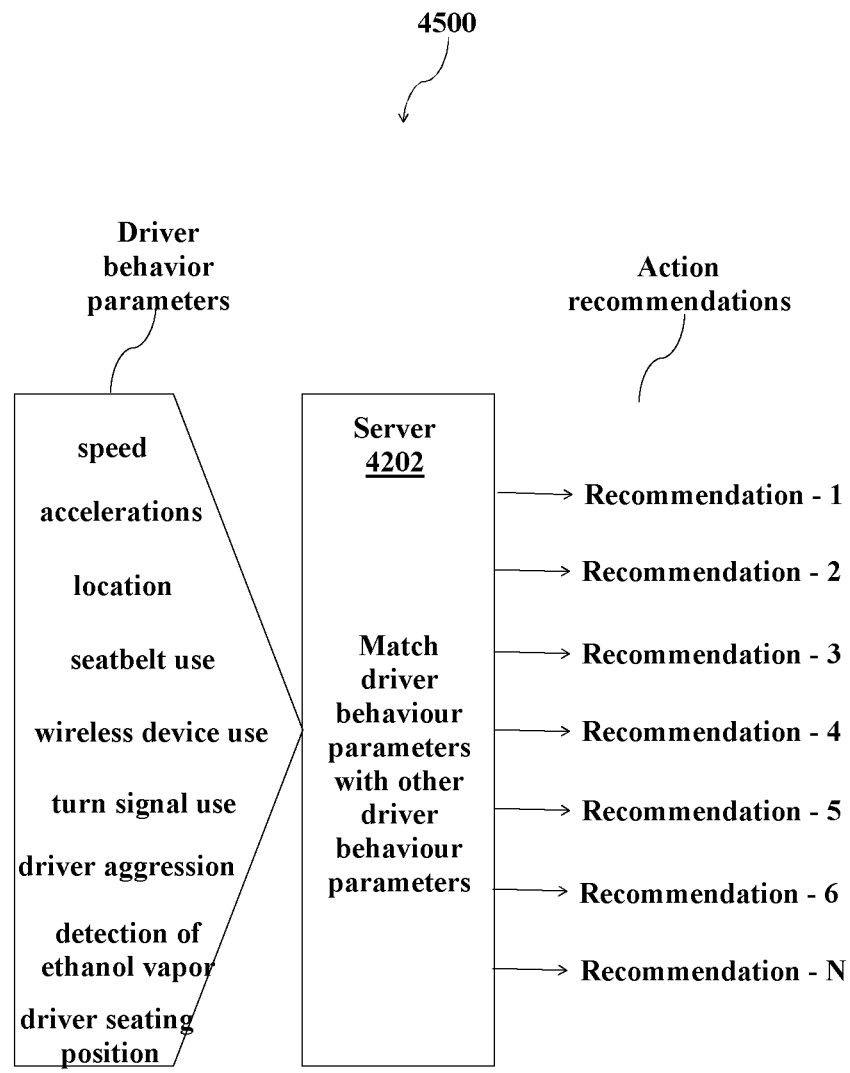
FIG. 15 is a diagram illustrates generally, an overview of a reasonableness determination system that may allow drivers to obtain action recommendations based on the driver behavior parameters, according to embodiments disclosed herein.

FIG. 15 is a diagram 4500 illustrates generally, an overview of a reasonable action determination system that may allow drivers to obtain action recommendations based on the driver behavior parameters, according to embodiments disclosed herein. In an embodiment, the driver behavior parameters can be used to provide customized recommendations to drivers by comparing the driver behavior parameters with other drivers who has similar or substantially similar behavior parameters. Unlike conventional system, the server 106 can be configured to adaptively generate action recommendations for the driver based on the behavior parameters. The server 106 can be configured to match the behavior parameters of the drivers to similar behavior parameters of the one or more drivers, such as to provide personalized action recommendations to the driver. In an embodiment, the recommendations can be filtered in advance of display. In an embodiment, filtered recommendations may be derived from the sources such as for example, but not limited to, those sources that have added the data within a specified time, from those sources that share specific similarities with the sources, those sources that have been preselected by the driver as relevant, those sources that are selected as friends or friends of friends, and the like, those sources that are determined to provide valuable reviews/ratings or are specifically declared to be experts within the system or by the driver, or those users that have entered at least a minimum amount of data into the system.

FIG. 16 is a diagram 4600 illustrates generally, an overview of preferences matching by the server 4106, according to embodiments disclosed herein. FIG. 16 outlines reasonableness determination functionality in accordance with an embodiment of the present invention. The system 4100 can monitor the driver behavior and uses the behavior data to match with the behavior data of other sources and provide reasonable recommendations to the driver. In an embodiment, the reasonableness recommendation rules may be established in the recommendation system such as described in the FIG. 16. Such rules derived from, for example, but not limited to, automatic generation machine learning, automatic generation using a generic algorithm, automatic generation using a neutral network, automatic generation using a rule inference system, data mining, generation using a preset list of recommendations, and/or a driver behavior. In an embodiment, the sever 106 can be configured to receive the recommendation rules such as unidirectional rules, bidirectional rules, generalized rules including multi-way rules, rules among items, rules among sets, rules among collections, rules with weight factors, rules with priorities, un-weighted and un-prioritized rules, and the like.

Figure 17:
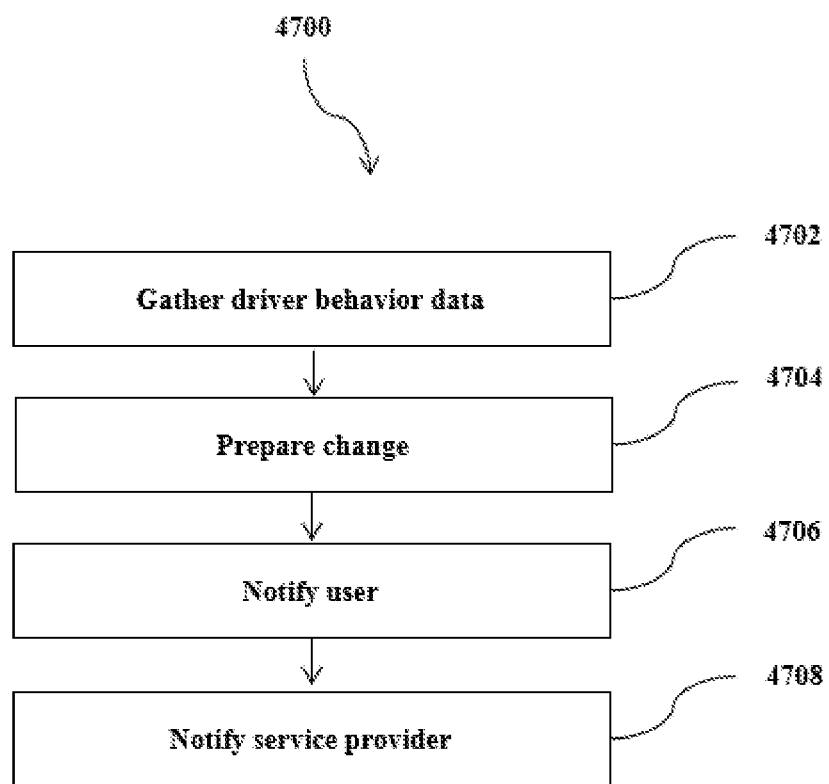
FIG. 17 is a flow chart illustrates generally, a method for selectively providing insurance information to a service provider, according to embodiments as disclosed herein.

FIG. 17 is a flow chart illustrates generally, a method 4700 for selectively providing reasonable driving information to a service provider, according to embodiments as disclosed herein. At step 4702, the autonomous behavior is monitored. The behavior data can include external parameters and/or internal parameters. In an embodiment, the autonomous behavior data/parameters described herein can include for example, but not limited to, vehicle speed, vehicle accelerations, driver location, seatbelt use, wireless device use, turn signal use, driver aggression, detection of ethanol vapor, driver seating position, time, and the like. In an embodiment, the behavior data can be over a period of hours, days, weeks, and so forth. In an embodiment, the behavior data gathering can be continuous, at predefined intervals, or at random intervals. In accordance with some aspects, data can be gathered while a vehicle is in operation and at other times (e.g., at two a.m. to determine where the vehicle is parked overnight). In an embodiment, a change to an insurance premium and/or an insurance coverage is prepared, at 4704. The change is based on one or more of the vehicle behavior data, wherein each item of driver behavior data can have a different weight assigned. For example, data gathered related to weather conditions might be given less weight than data gathered related to user distractions (e.g., passengers, use of a mobile device while vehicle is in operation, and so forth). In another example, excessive speed might be assigned a higher weight than data related to safety performance of the vehicle. As such, data with a higher weight can be given more consideration than data with a lower weight (e.g., data assigned a higher weight can have a greater impact on the cost of insurance). Thus, if the user is traveling at (or below) the speed limit and speed is assigned a greater weight, then the safe speed will tend to decrease (or remain constant) the cost of insurance.

In an embodiment, the autonomous controller is notified of the change, at 4706. The notification can be in any perceivable format. In an example, the notification is provided as a dashboard-mounted display. In another example, presenting the change can include displaying the modified cost of the insurance policy in a dashboard-mounted display and/or a heads-up display. In an embodiment, a service provider is notified of the change, at 708. At substantially the same time as notifying the service provider (or trusted third party) of the change, parameters taken into consideration (and associated weight) can also be provided. In such a manner, the service provider (or third party) can selectively further modify the cost of insurance, which can be communicated to the user though the vehicle display or through other means.

The service provider (or third party) might be provided the change information less often than the insurance cost change information is provided to the user. For example, the user can be provided the insurance cost change information dynamically and almost instantaneously with detection of one or more parameters that can influence the insurance cost. However, the insurance provider (or third party) might only be notified of the change after a specified interval (or based on other intervals). For example, insurance cost changes might be accumulated over a period of time (e.g., two weeks) and an average of the insurance cost changes might be supplied to insurance provider. In such a manner, the user has time to adjust parameters that tend to increase (or decrease) the cost of insurance, which allows the user to have more control over the cost of insurance.

In an embodiment, Vertical market specialization for insurance is provided where markets are defined based on granular aspects of coverage and presented to one or more insurance subsystems to obtain quotes for a coverage premium. Such specialization allows insurance companies to compete in more specific areas of insurance coverage, which allows for more accurate premium rates focused on the specific areas or one or more related scenarios. In addition, the granular aspects of coverage can be provided to one or more advertising systems in exchange for further lowered rates, if desired.

According to an example, an insurance market can be defined based on granular information received regarding an item, a related person, use of the item, etc. Based on the market, premium quotes can be obtained from one or more insurance subsystems related to one or more insurance brokers. In addition, rates can be decreased where the granular information can be provided to an advertising system, in one example. In this regard, targeted advertisements can additionally be presented to system related to requesting the insurance coverage. Policies can be automatically selected based on preferences, manually selected using an interface, and/or the like.

Figure 18:
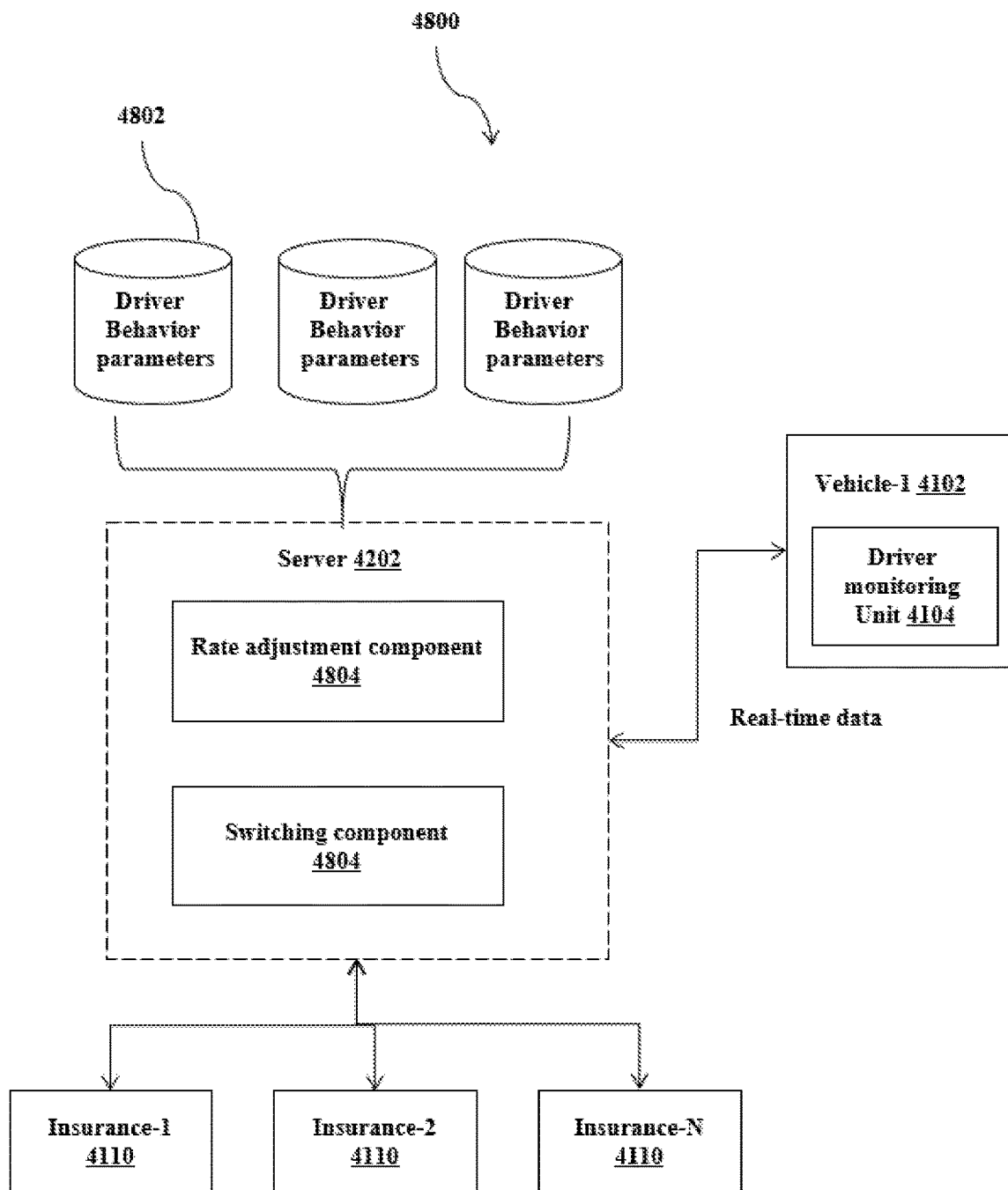
FIG. 18 is a diagram illustrates generally, an exemplary system that customizes insurance rates to correspond to behavior driver, according to embodiments as disclosed herein.

FIG. 18 is a diagram 4800 illustrates generally, an exemplary system that customizes insurance rates to correspond to behavior driver, according to embodiments as disclosed herein. In an embodiment, the server 4106 can be configured to maintain a database component 4802 including data related to different driver behaviors. Such leveraging from data banks enables insurance providers to bid in real time, and hence an owner and/or user of a vehicle can benefit from competition among various insurance providers, to obtain optimum rates. The server includes a rate adjustment component 4804 that in real time can determine the various rates from a plurality of insurance providers 4110 (1 to N, where N is an integer). In one particular aspect, a retrieval agent (not shown) associated with the rate adjustment component 4804 can pull insurance data from the insurance providers based on the contextual data supplied thereto. For example, such contextual data can be data records related to driver behavior, the vehicle 4102 (such as auto shop service records, current service status for the car, and the like), data related to the individual driver (such as health records, criminal records, shopping habits, and the like), data related to the environment (road condition, humidity, temperature, and the like) and data related to real time driving (frequency of braking, accelerating, intensity of such actions, and the like).

The retrieval agent (not shown) can pull data from the insurance providers 4110 and further publish such data to enable a rich interaction between the users on a display or a within a written communication environment. The retrieval agent can further generate an instance for a connection with the insurance providers. Accordingly, a connection instance can be employed by the rate adjustment component 4804 to store connection information such as the state of data conveyance, the data being conveyed, connection ID and the like. Such information can additionally be employed to monitor progress of data transfer to the written communication environment or display, for example.

Accordingly drivers/owners of motor vehicles can pull or receive data from the insurance providers 4110, wherein received data can be posted (e.g., displayed on a monitor) and the connection instance can be concurrently updated to reflect any successful and/or failed data retrievals. Thus, at any given moment the connection instance can include the most up-to-date version of data transferred between the motor vehicle and the insurance providers. In an embodiment, a switching component 4806 can be configured to automatically switch user/driver to an insurance provider/company that bids the best rate. Such switching component 4806 can employ interrupts both in hardware and/or software to conclude the switching from one insurance provider to another insurance provider. For example, the interrupt can convey receipt of a more optimal insurance rate or completion of a pull request to the insurance providers 4110 or that a configuration has changed. In one particular aspect, once an interrupt occurs, an operating system analyzes the state of the system and performs an action in accordance with the interrupt, such as a change of insurance provider, for example Such interrupts can be in form of asynchronous external events to the processor that can alter normal program flow. Moreover, the interrupts can usually require immediate attention from a processor(s) associated with the system. In one aspect, when an interrupt is detected, the system often interrupts all processing to attend to the interrupt, wherein the system can further save state of the processor and instruction pointers on related stacks.

According to a further aspect, the switching component 4804 can employ an interrupt dispatch table in memory, which can be accessed by the processor to identify a function that is to be called in response to a particular interrupt. For example, a function can accept a policy from an insurance provider, cancel an existing policy, and/or clear the interrupt for a variety of other reasons. The function can execute processes such as clearing the state of the interrupt, calling a driver function to check the state of an insurance policy and clearing, setting a bit, and the like.

Figure 19:
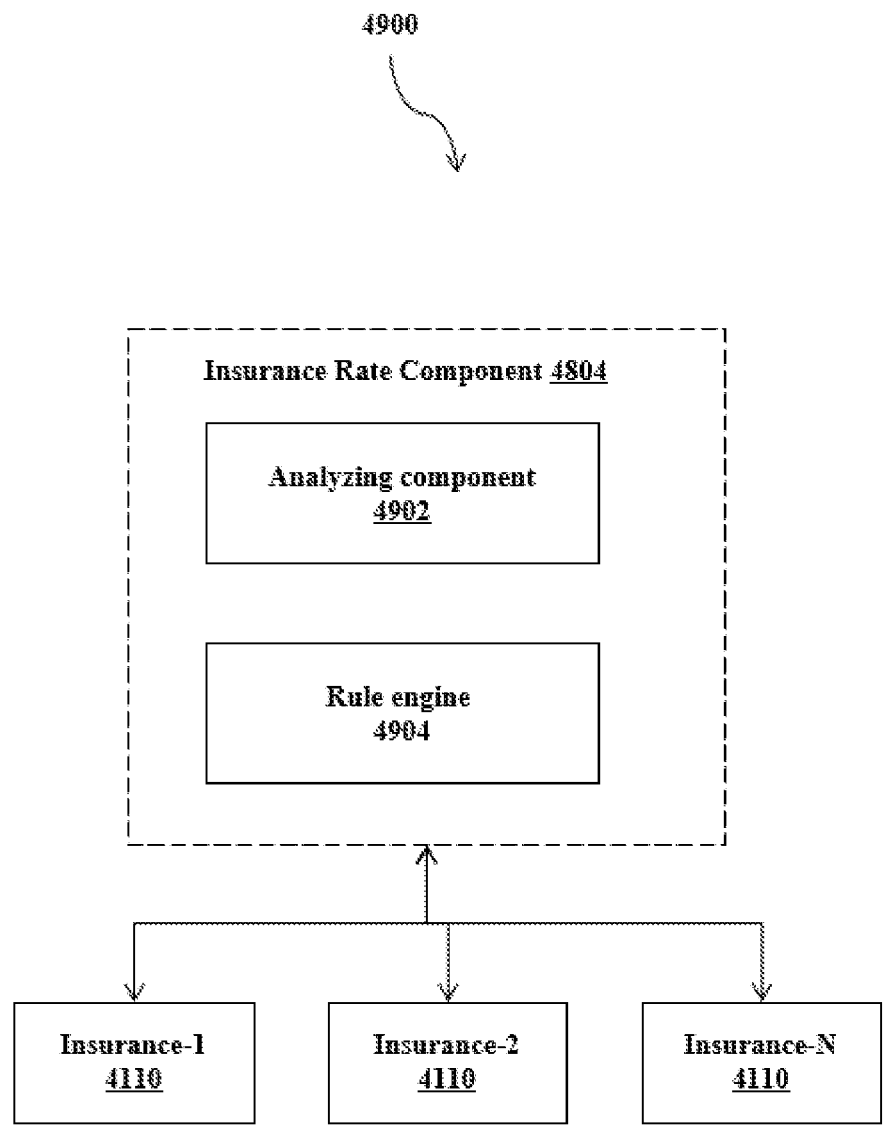
FIG. 19 is a diagram illustrates generally an insurance rate adjustment component that further includes an analyzer component, according to embodiments as disclosed herein.

FIG. 19 is a diagram 4900 illustrates generally, the switching component 806 that further includes an analyzer component 4902, which further employs threshold ranges and/or value(s) (e.g., pricing ranges for insurance policies, terms of the insurance policy, and the like) according to a further aspect of the present invention. The analyzer component 4902 can be configured to compare a received value for insurance coverage to the predetermined thresholds, which can be designated by an owner/driver. Accordingly, the analyzer component 902 can determine if the received insurance coverage policies are within the desired range as specified by a user an "accept" or "reject", and/or further create a hierarchy from "low" to "high" based on criteria designated by the user (e.g., price of the insurance policy, terms of the insurance policy, and the like).

According to a further aspect, the analyzer component 4902 can further interact with a rule engine component 4904. For example, a rule can be applied to define and/or implement a desired evaluation method for an insurance policy. It is to be appreciated that the rule-based implementation can automatically and/or dynamically define and implement an evaluation scheme of the insurance policies provided. Accordingly, the rule-based implementation can evaluate an insurance policy by employing a predefined and/or programmed rule(s) based upon any desired criteria (e.g., criteria affecting an insurance policy such as duration of the policy, number of drivers covered, type of risks covered, and the like).

In a related example, a user can establish a rule that can implement an evaluation based upon a preferred hierarchy (e.g., weight) of criteria that affects the insurance policy. For example, the rule can be constructed to evaluate the criteria based upon predetermined thresholds, wherein if such criteria does not comply with set thresholds, the system can further evaluate another criteria or attribute(s) to validate the status (e.g., "accept" or "reject" the insurance bid and operate the switching component based thereon). It is to be appreciated that any of the attributes utilized in accordance with the subject invention can be programmed into a rule-based implementation scheme.

Figure 20:
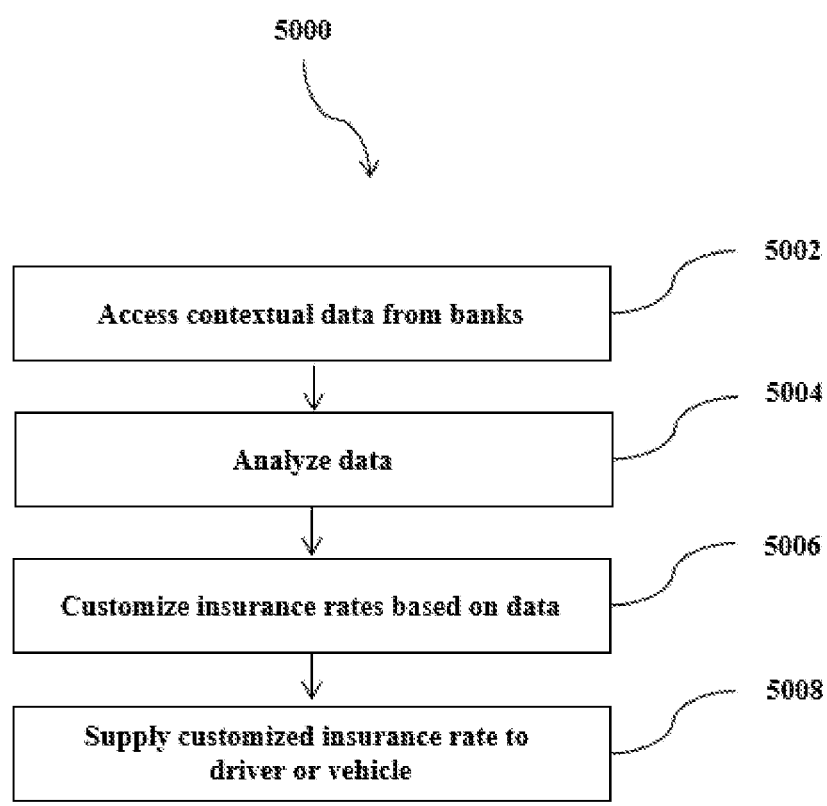
FIG. 20 illustrates generally, a method for customizing insurance rates of a driver, according to embodiments as described herein.

FIG. 20 illustrates generally, a method 5000 for customizing insurance rates of a driver, according to embodiments as described herein. The methodology 5000 of customizing insurance rates according to a further aspect of the subject innovation. While the exemplary method is illustrated and described herein as a series of blocks representative of various events and/or acts, the subject innovation is not limited by the illustrated ordering of such blocks. For instance, some acts or events may occur in different orders and/or concurrently with other acts or events, apart from the ordering illustrated herein, in accordance with the innovation. In addition, not all illustrated blocks, events or acts, may be required to implement a methodology in accordance with the subject innovation. Moreover, it will be appreciated that the exemplary method and other methods according to the innovation may be implemented in association with the method illustrated and described herein, as well as in association with other systems and apparatus not illustrated or described. Initially and at 5002 contextual data from various data banks can be accessed by the insurance providers or supplied thereto. As explained earlier, the data banks can include data pertaining to the motor vehicle (e.g., maintenance history, current vehicle conditions, and the like), data related to the driver (e.g., via health insurance records, police records, internet records, and the like), and data related to operating environment (e.g., weather, geographical location, and the like.) Moreover, the real-time contextual driving data can include both an intensity portion and a frequency portion, which represent severity and regularity of driving episodes (e.g., slamming the brakes, gradual/sudden deceleration, velocity variances, and the like). Subsequently and at 5004, such data can be analyzed by the insurance providers as to customize an insurance rate based thereon at 5006. In an embodiment, insurance rate can be calculated in real-time and as such can more accurately reflect appropriate coverage for a situation of a driver. A plurality of different factors can influence a likelihood of the driver being involved in an accident, having a vehicle stolen, and the like. For example, if the driver is travelling through bad weather, then risk can be higher and a rate can be increased in real-time as weather conditions change-conversely, if there is relatively little traffic surrounding the driver's vehicle, then the rate can be lowered. An algorithm or complex model can be used to calculate the insurance rates and can be disclosed to the driver through the display. In an embodiment, the rate adjustment component 804 can be configured to evaluate the insurance rate information against current vehicle operation by the driver. Specifically, the evaluation can compare the current operation against insurance rate information to determine if an appropriate rate is being used, if the rate should be changed, what the change should be, etc. For instance, different aspects of vehicle operation can be taken into account such as for example, but not limited to, weather and how a driver reacts, speed (of a vehicle), traffic and how the driver reacts, and noise {e.g., radio level), and the like.

Subsequently, the customized insurance rate can then be sent from an insurance provider to an owner/driver of the vehicle (e.g., in form of an insurance bid) at 5008. For example, the insurance rate can be determined and represented upon the driver via the display or controller in the vehicle. A processor that executes the computer executable components stored on a storage medium can be employed. In an embodiment, the monitoring unit can communicate with an insurance company {e.g., continuous communication) and obtain an insurance rate directly. The system can be configured to customize the insurance based on the obtained insurance rates and present to the dirver and make appropriate modification to the display automatically.

Figure 21:
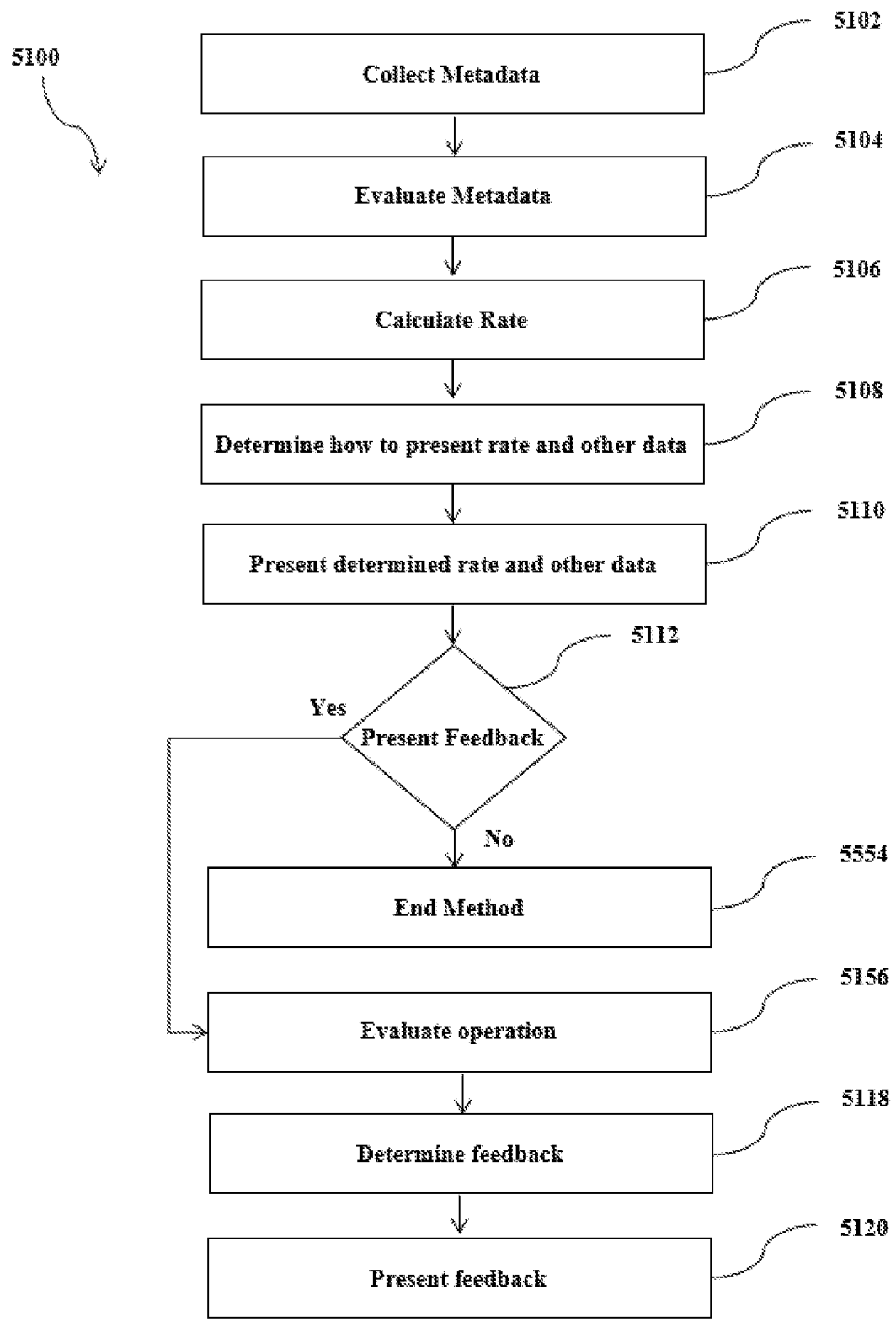
FIG. 21 illustrates generally, a method for presenting information related to a real-time insurance rate, according to embodiments as described herein.

FIG. 21 illustrates generally, a method 1100 for presenting information related to a real-time insurance rate, according to embodiments as described herein. In an embodiment, at 5102, Metadata can be collected pertaining to real-time operation of a vehicle and at least a portion of the metadata can be evaluated, as shown at 5104. The metadata described herein can include driver behavior data, contextual information, driver history, and real-time driving information that relates to operation of a driver and vehicle, and the like. Based upon a result of the evaluation, there can be calculation a real-time insurance rate, such as shown at 5106. In an embodiment, at 5108, determination can be made on how to present the calculated rate. For example, the determination can be if the rate should be shown on a center console or a heads-up display. A determination can also be made on how to display data (e.g., if a numerical rate should be disclosed or a color element should be lit). Additionally, a determination can be made on other data to disclose, such as safety, environment impact, cost of operating vehicle, a target speed, group rank, and the like. The determined rate and other determined data can be presented through a display, such as shown at 5110. Thus, the determined rate is presented upon a display viewable to the driver of the vehicle.

In an embodiment, at 5112, the method 5100 includes determining if feedback should be presented to the user. The feedback can be supplied in real-time as well as be a collective summary presented after a driving session is complete. If no feedback should be presented, then the method 5100 can end at 5114. In one instance, if there is a new driver attempting to obtain a full drivers license (e.g., teenage driver) or newer driver, then the check 5112 can determine feedback should be automatically provided. In another embodiment, an operator can be solicited on if feedback should be presented depending on a response the method 5100 can end or continue.

Operation of the vehicle and driver can be evaluated at 5116, which can occur though different embodiments. As a user operates a vehicle, metadata can be collected and evaluated in real-time. In an alternative embodiment, data can be collected, but evaluation does not occur until the check 5112 determines feedback should be presented. At 5118, there can be determining feedback for suggesting future driving actions for the operator to perform in future driving to lower the insurance rate. The method 5100 can include presenting the feedback (e.g., through the display, through a printout, transferring feedback as part of e-mail or a text message, etc.) at 5120. The feedback can be directly related to a driving session as well as is an aggregate analysis of overall driving performance (e.g., over multiple driving sessions).

Figure 22:
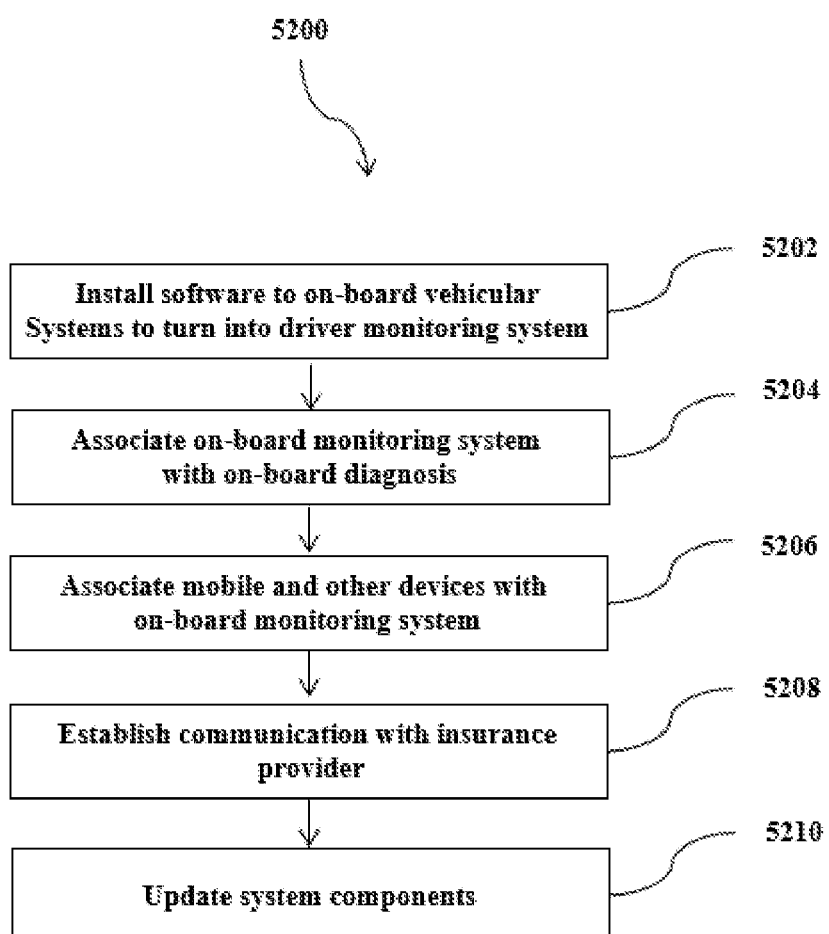
FIG. 22 is diagram illustrates generally, a method for installation of a real-time insurance system, according to embodiments disclosed herein.

FIG. 22 is diagram illustrates generally, a method 5200 for installation of a real-time insurance system, according to embodiments disclosed herein. In an embodiment, at 5202, an on-board monitoring system (such as driver monitoring unit) 4102 is installed in a vehicle to facilitate the collection of real-time data from the vehicle and forwarding of the real-time data to an insurance provider. At 5204, the on-board monitoring system can be associated with the on-board data/diagnostic control units and system(s) incorporated into the vehicle. The on-board data/diagnostic control units and system(s) can include the vehicles engine control unit/module (ECU/ECM), transmission control unit (TCU), power train control unit (PCU), on-board diagnostics (OBD), sensors and processors associated with the transmission system, and other aspects of the vehicle allowing the on-board monitoring system to gather sufficient data from the vehicle for a determination of how the vehicle is being driven to be made. The on-board monitoring system can be communicatively coupled by hard wiring to the on-board diagnostic system(s) or the systems can be communicatively associated using wireless technologies.

In an embodiment, at 5206, a mobile device (e.g., a cell phone) can be associated with the onboard monitoring system where the mobile device can facilitate communication between the on-board monitoring systems with a remote insurance provider system. The mobile device provides identification information to the on-board monitoring system to be processed by the on-board monitoring system or forwarded an insurance provider system to enable identification of the driver.

In an embodiment, at 5208, communications are established between the on-board monitoring system and the mobile device with the remote insurance provider system. In one embodiment it is envisaged that the on-board monitoring system and the insurance provider system are owned and operated by the same insurance company. However, the system could be less restricted whereby the insurance provider system is accessible by a plurality of insurance companies with the operator of the on-board monitoring system, e.g., the driver of the vehicle to which the on-board monitoring system is attached, choosing from the plurality of insurance providers available for their particular base coverage. In such an embodiment, upon startup of the system the insurance provider system can default to the insurance company providing the base coverage and the operator can select from other insurance companies as they require. Over time, as usage of the on-board monitoring system continues, at 5210, there is a likelihood that various aspects of the system might need to be updated or replaced, e.g., software update, hardware updates, etc., where the updates might be required for an individual insurance company system or to allow the on-board monitoring system to function with one or more other insurance company systems. Hardware updates may involve replacement of a piece of hardware with another, while software updates can be conducted by connecting the mobile device and/or the on-board monitoring system to the internet and downloading the software from a company website hosted thereon. Alternatively, the software upgrade can be transmitted to the mobile device or the on-board monitoring system by wireless means. As a further alternative the updates can be conferred to the mobile device or the on-board monitoring system by means of a plug-in module or the like, which can be left attached to the respective device or the software can be downloaded there from.

Figure 23:
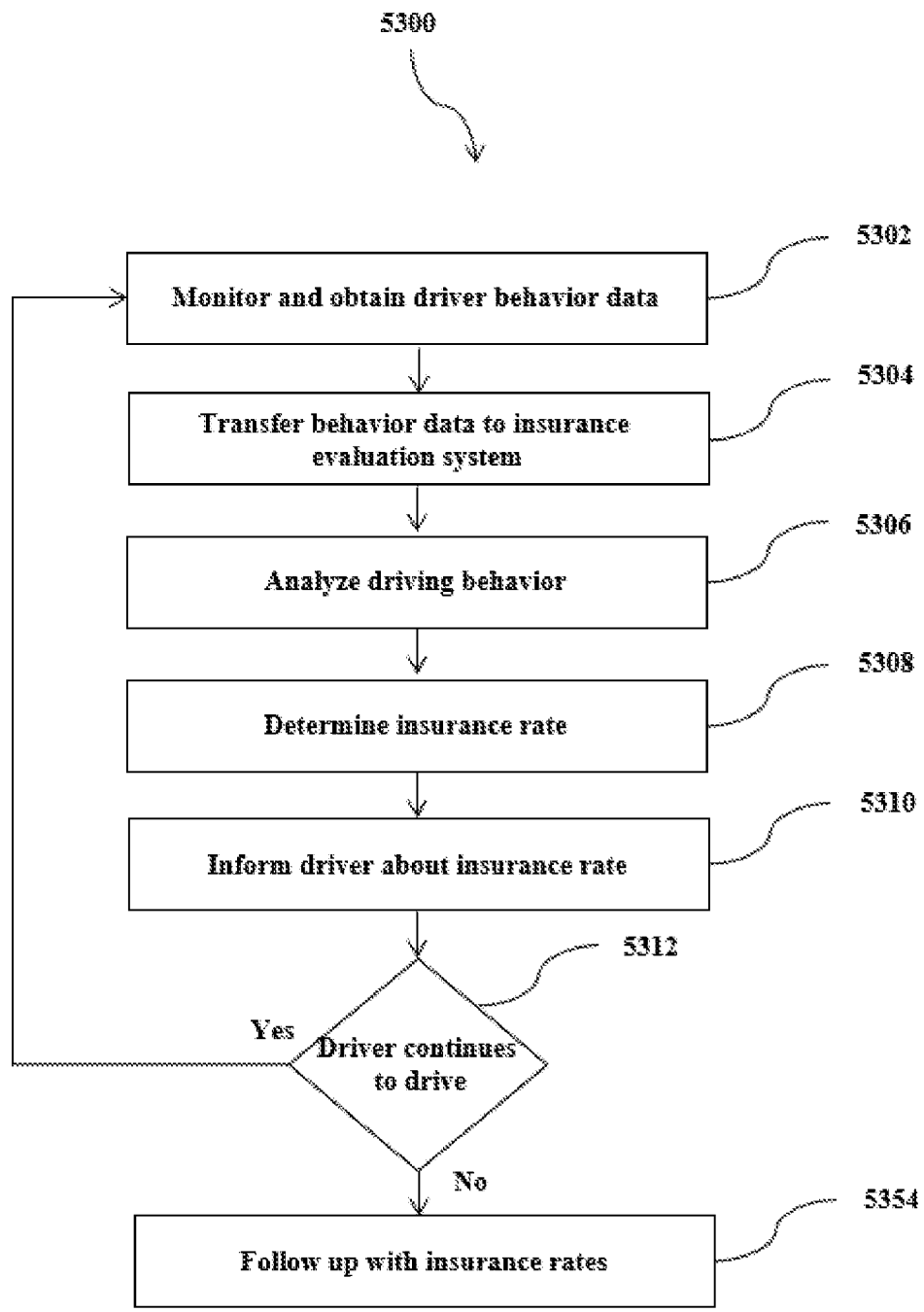
FIG. 23 is a diagram illustrates generally, a method for gathering information from an on-board monitoring system employed in a real-time insurance system, according to embodiments as disclosed herein.

FIG. 23 is a diagram illustrates generally, a method for gathering information from an on-board monitoring system employed in a real-time insurance system, according to embodiments as disclosed herein. In an embodiment, at 5302, monitoring of the driver and the vehicle they are operating is commenced. Monitoring can employ components of an on-board monitoring system, mobile device components, e.g., cell phone system, or any other system components associated with monitoring the vehicle as it is being driven. Such components can include a global positioning system (GPS) to determine the location of the vehicle at any given time, such a GPS can be located in a cell phone, as part of the on-board monitoring system, or an external system coupled to the monitoring system/cell phone—such an external system being an OEM or after sales GPS associated with the vehicle to be/being driven. A video data stream can be gathered from a video camera coupled to the on-board monitoring system recording the road conditions, etc. throughout the journey. Information can also be gathered from monitoring/control system(s) that are integral to the vehicle, e.g., the vehicle's engine control unit/module (ECU/ECM) that monitors various sensors located throughout the engine, fuel and exhaust systems, etc.

In an embodiment, at 5304, the dynamically gathered data (or driver behavior data) is transmitted to an insurance evaluation system. In an embodiment, at 5306, the gathered data is analyzed. Such analysis can involve identifying the route taken by the driver, the speed driven, time of day the journey was undertaken, weather conditions during the journey, other road traffic, did the user use their cell phone during the journey?, and the like. In an embodiment, at 5308, the gathered data is assessed from which an insurance rate(s) can be determined. For example, if the driver drove above the speed limit then an appropriate determination could be to increase the insurance premium. In an embodiment, at 5310, the driver can be informed of the newly determined insurance rate. Any suitable device can be employed such as informing the user by cell phone, a display device associated with the on-board monitoring system, or another device associated with the vehicle. The information can be conveyed in a variety of ways, including a text message, a verbal message, graphical presentation, change of light emitting diodes (LED's) on a display unit, a HUD, etc. At 5312, the driver can continue to drive the vehicle whereby the method can return to 5302 where the data gathering is commenced once more.

Alternatively, in an embodiment, at 5312, the driver may complete their journey and data gathering and analysis is completed. In an embodiment, at 5314 the driver can be presented with new insurance rates based upon the data gathered while they were driving the vehicle. The new insurance rates can be delivered and presented to the driver by any suitable means, for example the new insurance rates and any pertinent information can be forwarded and presented to the driver via a HUD employed as part of the real time data gathering system. By employing a HUD instantaneous notifications regarding a change in the driver's insurance policy can be presented while mitigating driver distractions {e.g., line of sight remains substantially unchanged). Alternatively, the on-board monitoring system can be used, or a remote computer/presentation device coupled to the real time data gathering system where the information is forwarded to the driver via, e.g., email. In another embodiment, the driver can access a website, hosted by a respective insurance company, where the driver can view their respective rates/gathered information/analysis system, etc. Further, traditional means of communication such as a letter can be used to forward the insurance information to the driver.

Figure 24:
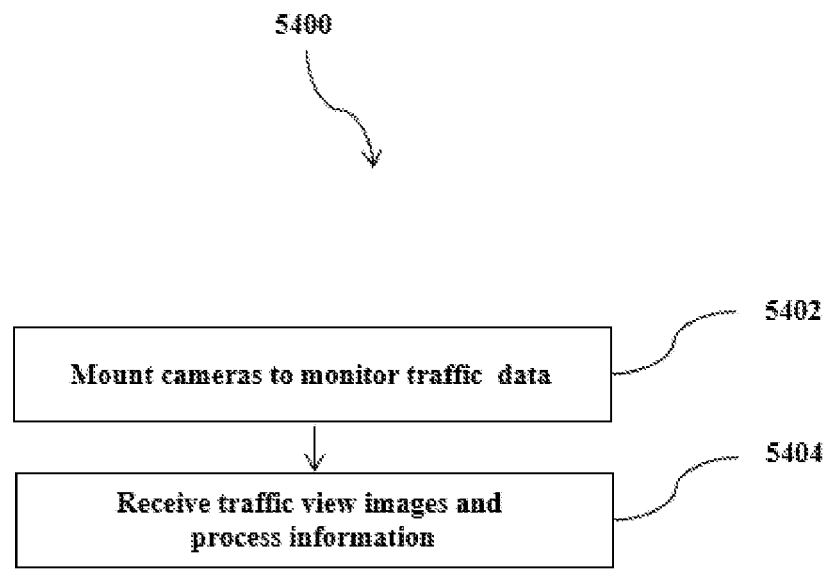
FIG. 24 is a diagram illustrates generally, a method mounting cameras to capture traffic information, according to embodiments as disclosed herein.

FIG. 24 is a diagram illustrates generally, a method 5400 mounting cameras to capture traffic information, according to embodiments as disclosed herein. In an embodiment, at 5402, the method 5400 includes mounting cameras on the car to monitor the traffic information. For example, the car may include cameras mounted to capture views in the rearward, downward, and the like directions, on the upper surface at the leading end of the front portion thereof. The position for mounting the cameras is not limited to the left side, right side, upper surface, front side, back side, and the like. For example, if the car has a left side steering wheel, the camera may be mounted on a right upper surface at a leading end of the front portion of the car. The cameras may have an angle of view of about 60, 90, 180, and 360 degree. With the construction, since the camera is mounted for a view in the rearward and downward directions on the front portion of the car, it can capture a wide area of the surface of the road in the vicinity of the driver's car, and an area in the vicinity of the left front wheel. Furthermore, the camera can also capture a part of the body of the car in the vicinity of the front wheel. Thereby, the relation between the car and the surface of the road can be recorded. In an example, the cameras can be configured to capture images of the road views including potential collision events such as how close car is following car in front, how often brake is used in period of time, hard brakes count more to reduce driver rating, how frequently does car come close to objects and obstructions (such as trees, cars on the other direction and cars in same direction) while moving.

In an embodiment, at 5404, the method 5400 includes receiving the recorded information from the camera and use image processing techniques to process the information. For example, the system uses image processing techniques to determine potential collision events such as how close car is following car in front, how often brake is used in period of time, hard brakes count more to reduce driver rating, how frequently does car come close to objects and obstructions (such as trees, cars on the other direction and cars in same direction) while moving.

Figure 25:
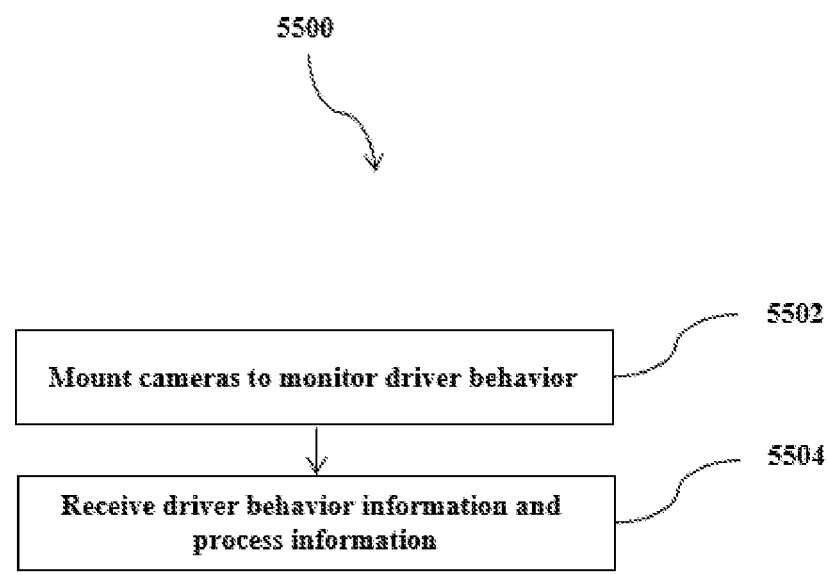
FIG. 25 is a diagram illustrates generally, a method mounting cameras to capture driver behavior, according to embodiments as disclosed herein.

FIG. 25 is a diagram illustrates generally, a method 5500 mounting cameras to capture driver behavior, according to embodiments as disclosed herein. In an embodiment, at 5502, the method 5500 includes mounting cameras on the car to monitor the driver behavior. The position for mounting the cameras is not limited to the left side, right side, upper surface, front side, back side, and the like. The cameras may have an angle of view of about 60, 90, 180, and 360 degree. For example, the camera can capture driver behavior such as for example, but not limited to, images of texting and use of phone while driving, speech of driver shouting or cursing at other drivers or other occupants, indications of intoxication, sleepiness, alcohol level, mood, aggressiveness, and the like. In an embodiment, at 5504, the method 5500 includes receiving the recorded information from the camera and use image processing techniques and voice reorganization techniques to process the information. For example, the system uses image processing techniques to determine the driver activity such as whether the driver is using mobile phone while driving. In another example, the system uses voice recognition techniques to determine the use voice, text, aggressiveness, and the like.

In an embodiment, the item-centric approach determines that many drivers having similar behavior and the driver who performs activity-A will also perform activity-B. This has proven to be fairly effective. On the other hand, many insurance providers interact with drivers online/offline. Such interaction can produce a stream of contextual information that recommendation engines can use. Early systems were batch oriented and computed recommendations in advance for each driver. Thus, they could not always react to a driver's most recent behavior. Recommendation engines work by trying to establish a statistical relationship between drivers and activities associated with there behavior. The system establishes these relationships via information about driver's behavior from vehicle owner, monitoring devices, sensors, and the like.

In an embodiment, the reasonableness determination systems collect data via APIs, insurance application, insurance databases, and the like sources. The insurance sources can be available through social networks, ad hoc and marketing networks, and other external sources. For example, data can be obtained from insurance sites, insurance providers, driver insurance history, and search engines. All this enables recommendation engines to take a more holistic view of the driver. The recommendation engine can recommend different insurance products that save money for the driver, or alternatively can even recommend different insurance companies to save money. Using greater amounts of data lets the engines find connections that might otherwise go unnoticed, which yields better suggestions. This also sometimes requires recommendation systems to use complex big-data analysis techniques. Online public profiles and preference listings on social networking sites such as Facebook add useful data.

Most recommendation engines use complex algorithms to analyze driver behavior and suggest recommended activities that employ personalized collaborative filtering, which use multiple agents or data sources to identify behavior patterns and draw conclusions. This approach helps determine that numerous drivers who have same or similar type of behavior in the past may have to perform one or more similar activities in the future. Many systems use expert adaptive approaches. These techniques create new sets of suggestions, analyze their performance, and adjust the recommendation pattern for similar behavior of drivers. This lets systems adapt quickly to new trends and behaviors. Rules-based systems enable businesses to establish rules that optimize recommendation performance.

Figure 26:
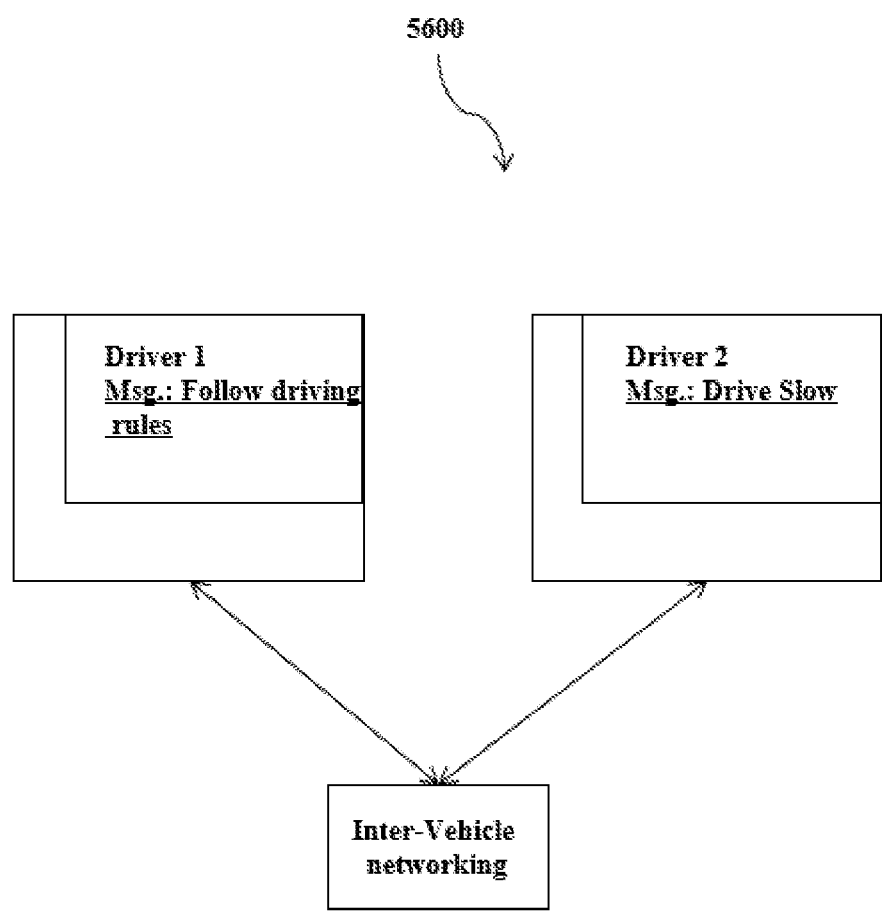
FIG. 26 is a diagram illustrates generally, a first vehicle program communicating with a second vehicle program through an Inter-Vehicle Communication, according to embodiments as disclosed herein.

FIG. 26 is a diagram 5600 illustrates generally, a first vehicle program communicating with a second vehicle program through an Inter-Vehicle networking, according to embodiments as disclosed herein. In an embodiment, the system develops inter-vehicular networking, computing, transceivers, and sensing technologies in the vehicles. Such vehicles have embedded computers, GPS receivers, short-range wireless network interfaces, and potentially access to in-car sensors and the Internet. Furthermore, they can interact with road-side wireless sensor networks and sensors embedded in other vehicles. These capabilities can be leveraged into distributed computing and sensing applications over vehicular networks for safer driving, dynamic route planning, mobile sensing, or in-vehicle entertainment. The system can include vehicular-specific network protocols, middleware platforms, and security mechanisms to process the data. As shown in FIG. 26, a first driver operating a vehicle observes a second driver operating a vehicle within his visual range and wants to send a message to the second driver. The vehicle can include identifying information that is visually ascertainable such as the model, vehicle color, number of doors, license plate number and state. The vehicle may include additional information that is only ascertainable from up close or at certain angles, or via certain technologies, such as a roof top identification number, vehicle identification number, taxi badge number, Bluetooth, or RFID code, and the like. In an embodiment, a sender having access to the vehicle monitoring device and viewing a second vehicle desires to contact the driver of the second vehicle. In one embodiment, in case of an accident as detected by an accelerometer or airbag deployment, both vehicles automatically exchange insurance information and the drivers simply confirm and signs to accept. In another embodiment, in case of a hit-and-run, the vehicle computer would automatically capture insurance information from the other vehicle and store all parameters arising from the accident for accident investigator's review. In another embodiment, if one vehicle detects that the other vehicle has a low insurance rating, the vehicle automatically enters a defensive driving mode around that vehicle. As best shown in FIG. 16, the sender initiates communication via a telephone or handheld computer or vehicle monitoring device and accesses the interface to the inter-vehicle networking service and database. The sender can select "send message" from the graphical or audio menu to send message or directly communicate with the driver of the second vehicle.

For example, the sender can directly communicate with the driver using the inter-vehicle networking or the sender can choose from a table of messages that can be sent to the driver using the inter-vehicle networking. For example, the message can take the form of voice, audio, video, or other data which can be converted to a digital signal and sent to any communications terminal. The inter-vehicle networking database receives the message or encrypted message and reconstructs the message, including the address information. The inter-vehicle networking then separates out the address information including such as for example, but not limited to, license plate number, vehicle identification number, and the like.

In an embodiment, the message may include a return address for the sender, so that a reply can be returned merely by hitting the "reply to" or "call back" button on the message. One skilled in the art would also recognize that the message could be sent anonymously or by a non-returnable address. Alternatively, the message could be a general broadcast sent by a police officer or other official sending a warning message to speeders or an informational message such as "road closed ahead" or other message.

In this case, the transceiver can be a WiMAX system. In another embodiment, the transceiver can be a meshed 802 protocol network configuration with a constantly morphing mobile mesh network that helps drivers avoid accidents, identify traffic jams miles before they encounter them, and act as a relay point for Internet access. In one embodiment, the mesh network can be the ZigBee mesh network. In another embodiment, the mesh network can be a modified Wi-Fi protocol called 802.11p standard for allowing data exchange between moving vehicles in the 5.9 GHz band. 802.11p operates in the 5.835-5.925 GHz range, divided into 7 channels of 10 MHz each. The standard defines mechanisms that allow IEEE 802.11™ technology to be used in high speed radio environments typical of cars and trucks. In these environments, the 802.11p enhancements to the previous standards enable robust and reliable car-to-car and car-to-curb communications by addressing challenges such as extreme Doppler shifts, rapidly changing multipath conditions, and the need to quickly establish a link and exchange data in very short times (less than 100 ms). Further enhancements are defined to support other higher layer protocols that are designed for the vehicular environment, such as the set of IEEE1609™ standards for Wireless Access in Vehicular Environments (WAVE). 802.11p supports Intelligent Transportation Systems (ITS) applications such as cooperative safety, traffic and accident control, intersection collision avoidance, and emergency warning.

One variation of 802.11p is called the Dedicated Short Range Communications (DSRC), a U.S. Department of Transportation project as well as the name of the 5.9 GHz frequency band allocated for the ITS communications. More information on the 802.11p standard can be obtained from the IEEE. DSRC itself is not a mesh. It's a broadcast, so it only reaches vehicles within range. Meshing requires a lot more sophistication. There's a routing aspect to it, relaying messages to other nodes. DSRC is much simpler.

One embodiment uses high-powered, heavily encrypted Wi-Fi that establishes point-to-point connections between cars within a half-mile radius. Those connections are used to communicate vital information between vehicles, either triggering alerts to the driver or interpreted by the vehicle's computer. An intelligent car slamming on its brakes could communicate to all of the vehicles behind it that it's coming to rapid halt, giving the driver that much more warning that he too needs to hit the brakes.

But because these cars are networked—the car in front of one vehicle is connected to the car in front it and so forth—in a distributed mesh, an intelligent vehicle can know if cars miles down the road are slamming on their brakes, alerting the driver to potential traffic jams. Given enough vehicles with the technology, individual cars become nodes in a constantly changing, self-aware network that can not only monitor what's going on in the immediate vicinity, but across a citywide traffic grid.

In one embodiment, the processor receives travel routes and sensor data from adjacent vehicles, such information is then used for preparing vehicular brakes for a detected turn or an anticipated turn from adjacent vehicles. The travel routes can be transmitted over a vehicular Wi-Fi system that sends protected information to nearby vehicles equipped with Wi-Fi or Bluetooth or ZigBee nodes. In one embodiment, a mesh-network is formed with Wi-Fi transceivers, wherein each vehicle is given a temporary ID in each vehicular block, similar to a cellular block where vehicles can join or leave the vehicular block. Once the vehicle joins a group, travel routes and sensor data is transferred among vehicles in a group. Once travel routes are shared, the processor can determine potential or desired actions from the adjacent vehicles and adjust appropriately. For example, if the car in front of the vehicle is about to make a turn, the system prepares the brakes and gently tugs the driver's seat belt to give the drive notice that the car in front is about to slow down. In another example, if the processor detects that the driver is about to make a lane change to the left based on sensor data and acceleration pedal actuation, but if the processor detects that the vehicle behind in the desired lane is also speeding up, the system can warn the driver and disengage the lane change to avoid the accident. Thus, the processor receives travel routes and sensor data from adjacent vehicles and notifying the driver of a detected turn or an anticipated turn from adjacent vehicles. The processor receives travel routes and sensor data from adjacent vehicles and optimizes group vehicular speed to improve fuel efficiency. The processor receives travel routes and sensor data from adjacent vehicles and sequences red light(s) to optimize fuel efficiency. The processor notifies the driver of driving behaviors from other drivers at a predetermined location. The processor switches turn signals and brakes using a predetermined protocol to reduce insurance premium for the driver. The processor warns the driver to avoid driving in a predetermined pattern, driving during a predetermined time, driving in a predetermined area, or parking in a predetermined area to reduce insurance premium for the driver. The processor sends driver behavior data to an insurer, including at least one of: vehicle speed, vehicle accelerations, vehicle location, seatbelt use, wireless device use, turn signal use, detection of ethanol vapor, driver seating position, and time.

The various systems described above may be used by the computer to operate the vehicle and maneuver from one location to another. For example, a user may enter destination information into the navigation system, either manually or audibly. The vehicle may determine its location to a few inches based on a combination of the GPS receiver data, the sensor data, as well as the detailed map information. In response, the navigation system may generate a route between the present location of the vehicle and the destination.

When the driver is ready to relinquish some level of control to the autonomous driving computer, the user may activate the computer. The computer may be activated, for example, by pressing a button or by manipulating a lever such as gear shifter. Rather than taking control immediately, the computer may scan the surroundings and determine whether there are any obstacles or objects in the immediate vicinity which may prohibit or reduce the ability of the vehicle to avoid a collision. In this regard, the computer may require that the driver continue controlling the vehicle manually or with some level of control (such as the steering or acceleration) before entering into a fully autonomous mode.

Once the vehicle is able to maneuver safely without the assistance of the driver, the vehicle may become fully autonomous and continue to the destination. The driver may continue to assist the vehicle by controlling, for example, steering or whether the vehicle changes lanes, or the driver may take control of the vehicle immediately in the event of an emergency.

The vehicle may continuously use the sensor data to identify objects, such as traffic signals, people, other vehicles, and other objects, in order to maneuver the vehicle to the destination and reduce the likelihood of a collision. The vehicle may use the map data to determine where traffic signals or other objects should appear and take actions, for example, by signaling turns or changing lanes. Once the vehicle has arrived at the destination, the vehicle may provide audible or visual cues to the driver. For example, by displaying "You have arrived" on one or more of the electronic displays.

The vehicle may be only partially autonomous. For example, the driver may select to control one or more of the following: steering, acceleration, braking, and emergency braking.

The vehicle may also have one or more user interfaces that allow the driver to reflect the driver's driving a style. For example, the vehicle may include a dial which controls the level of risk or aggressiveness with which a driver would like the computer to use when controlling the vehicle. For example, a more aggressive driver may want to change lanes more often to pass cars, drive in the left lane on a highway, maneuver the vehicle closer to the surrounding vehicles, and drive faster than less aggressive drivers. A less aggressive driver may prefer for the vehicle to take more conservative actions, such as somewhat at or below the speed limit, avoiding congested highways, or avoiding populated areas in order to increase the level of safety. By manipulating the dial, the thresholds used by the computer to calculate whether to pass another car, drive closer to other vehicles, increase speed and the like may change. In other words, changing the dial may affect a number of different settings used by the computer during its decision making processes. A driver may also be permitted, via the user interface, to change individual settings that relate to the driver's preferences. In one embodiment, insurance rates for the driver or vehicle may be based on the style of the driving selected by the driver.

Aggressiveness settings may also be modified to reflect the type of vehicle and its passengers and cargo. For example, if an autonomous truck is transporting dangerous cargo (e.g., chemicals or flammable liquids), its aggressiveness settings may be less aggressive than a car carrying a single driver—even if the aggressive dials of both such a truck and car are set to "high." Moreover, trucks traveling across long distances over narrow, unpaved, rugged or icy terrain or vehicles may be placed in a more conservative mode in order reduce the likelihood of a collision or other incident.

In another example, the vehicle may include sport and non-sport modes which the user may select or deselect in order to change the aggressiveness of the ride. By way of example, while in "sport mode", the vehicle may navigate through turns at the maximum speed that is safe, whereas in "non-sport mode", the vehicle may navigate through turns at the maximum speed which results in g-forces that are relatively imperceptible by the passengers in the car.

The vehicle's characteristics may also be adjusted based on whether the driver or the computer is in control of the vehicle. For example, when a person is driving manually the suspension may be made fairly stiff so that the person may "feel" the road and thus drive more responsively or comfortably, while, when the computer is driving, the suspension may be made such softer so as to save energy and make for a more comfortable ride for passengers.

For purposes of illustration, a number of example implementations are described. It is to be understood, however, that the example implementations are illustrative only and are not meant to limiting. Other example implementations are possible as well.

It should be understood, of course, that the foregoing relates to exemplary embodiments of the invention and that modifications may be made without departing from the spirit and scope of the invention as set forth in the following claims.

What is claimed is:

1. A method of controlling a vehicle, comprising:
   mounting a plurality of cameras in a vehicular cabin to detect edges;
   translating the edges into motions of a driver, a human or a biological entity; and
   monitoring safety conditions for the driver, human or biological entity from the edges and motions with a processor to determine user motions to control the vehicle, the processor further controlling vehicle operation in response to the monitoring.

2. The method of claim 1, comprising sensing alcohol level by optically analyzing skin condition.

3. The method of claim 1, comprising monitoring the driver's driving pattern to confirm driver impairment.

4. The method of claim 1, comprising monitoring distance from start of braking to stopping the vehicle to determine driver impairment.

5. The method of claim 1, comprising storing in advance a best pattern to stop the vehicle in case of driver impairment and sending actuation instructions to components in the vehicle to safely stop the vehicle during driver impairment.

6. The method of claim 1, comprising selecting a maneuver based on objects near the vehicle, traffic characteristic, and weather characteristic and detected component damage; and moving the vehicle in accordance with the selected maneuver to a safe resting point.

7. The method of claim 1 comprising sensing heart rate and alcohol level by optically contacting
   a skin and detecting reflected light using an optical window on or a wearable device contacting the skin or on a spot on a driving wheel gripped by hands.

8. The method of claim 1 comprising detecting an object external to the vehicle and maneuvering in response to the object.

9. A method of controlling a vehicle, comprising:
   mounting a plurality of cameras in a vehicular cabin to detect edges;
   translating the edges into motions of a driver, a human or a biological entity;
   monitoring an impairment for the driver, human or biological entity; and
accelerating the vehicle slowly or turn more or less tightly in response to the impairment.

10. The method of claim 1, comprising autonomously and without direct human assistance navigate to a safe location, request help, and return to its original location after the driver has been assisted.

11. The method of claim 1, comprising:
    mounting a plurality of cameras in a vehicular cabin to detect edges of an object;
    sensing alcohol level with a set of breath sensors or touch-sensitive contact points from a driver of the vehicle and determining driver impairment level; and
    monitoring safety conditions for the human or biological entity.

12. The method of claim 1, wherein the biological entity comprises a child, an elderly person, a pet, or a living entity.

13. The method of claim 1, further comprising detecting a child is in a child safety seat; identifying a dangerous condition in a vehicle, and generating an alarm on the dangerous condition, wherein the alarm comprises a siren or a wireless signal to a car driver.

14. A method of controlling a vehicle, comprising:
    mounting a plurality of cameras in a vehicular cabin to detect edges;
    translating the edges into motions of a driver, a human or a biological entity;
    monitoring safety conditions for the driver, human or biological entity; and
controlling temperature of a driver and front passenger seats by monitoring an arm gesture and a finger gesture, wherein the number of fingers affect a seat temperature.

15. The method of claim 1, comprising:
    predicting a likely behavior of medical condition of the biological entity based on prior behavior data;
    preparing the vehicle to respond based at least in part on the likely behavior of the medical condition.

16. The method of claim 1, comprising:
    detecting an object external to a vehicle using one or more sensors;
    predicting a likely driver behavior in response to a likely behavior of a detected health condition based on prior behavior data;
    preparing the vehicle to respond based at least in part on the likely behavior of the detected object and the driver.

17. The method of claim 1, comprising:
    tracking a neighboring vehicle using one or more sensors;
    predicting a behavior of the neighboring vehicle based on at least the current state of the vehicle and the current state of an environment of the vehicle, wherein the at least one predicted behavior comprises the neighboring vehicle changing lanes; determining at least one confidence level, wherein the at least one confidence level represents a likelihood of the neighboring vehicle performing the at least one predicted behavior, and wherein the at least one confidence level is based on the at least one predicted behavior, the current state of the vehicle, and the current state of the environment of the vehicle;
    preparing the vehicle to respond based at least in part on the likely behavior of the neighboring vehicle and the driver; and
    notifying a driver of options based on the likely behavior.

18. The method of claim 1, comprising:
    sensing alcohol level with a set of breath sensors or touch-sensitive contact points from a driver of the vehicle;
    determining driver impairment level; and adjusting autonomous driving to maximize safety.

19. The method of claim 1, comprising sensing alcohol level by optically analyzing skin condition.

20. The method of claim 1, comprising monitoring the driver's driving pattern to confirm driver impairment.

* * * * *